US008541589B2

(12) United States Patent
Ouk et al.

(10) Patent No.: US 8,541,589 B2
(45) Date of Patent: Sep. 24, 2013

(54) THIOACETATE COMPOUNDS, COMPOSITIONS AND METHODS OF USE

(71) Applicant: Ardea Biosciences, Inc., San Diego, CA (US)

(72) Inventors: Samedy Ouk, San Diego, CA (US); Esmir Gunic, San Diego, CA (US); Jean-Michel Vernier, San Diego, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days.

(21) Appl. No.: 13/857,108

(22) Filed: Apr. 4, 2013

(65) Prior Publication Data

US 2013/0203779 A1 Aug. 8, 2013

Related U.S. Application Data

(63) Continuation of application No. 13/703,890, filed as application No. PCT/US2011/040585 on Jun. 15, 2011.

(60) Provisional application No. 61/355,491, filed on Jun. 16, 2010.

(51) Int. Cl.
*A61K 31/519* (2006.01)
*C07D 211/72* (2006.01)

(52) U.S. Cl.
USPC ........................................ 546/290; 514/262.1

(58) Field of Classification Search
None
See application file for complete search history.

(56) References Cited

U.S. PATENT DOCUMENTS

| | | | |
|---|---|---|---|
| 4,889,868 | A | 12/1989 | Huang et al. |
| 5,945,425 | A | 8/1999 | Moormann et al. |
| 6,017,925 | A | 1/2000 | Duggan et al. |
| 7,435,752 | B2 | 10/2008 | Girardet et al. |
| 7,947,721 | B2 | 5/2011 | Girardet et al. |
| 8,003,681 | B2 | 8/2011 | Girardet et al. |
| 8,084,483 | B2 | 12/2011 | Quart et al. |
| 8,173,690 | B2 | 5/2012 | Gunic et al. |
| 8,193,234 | B2 | 6/2012 | Gunic et al. |
| 8,372,807 | B2 | 2/2013 | De La Rosa et al. |
| 2007/0099970 | A1 | 5/2007 | Mackerall et al. |
| 2007/0249686 | A1 | 10/2007 | Bonnert et al. |
| 2009/0131384 | A1 | 5/2009 | Uysal et al. |
| 2010/0016337 | A1 | 1/2010 | Strobel et al. |
| 2010/0056464 | A1 | 3/2010 | Gunic et al. |
| 2010/0137323 | A1 | 6/2010 | Brown et al. |
| 2012/0122780 | A1 | 5/2012 | De La Rosa et al. |

FOREIGN PATENT DOCUMENTS

| | | |
|---|---|---|
| EP | 0587430 | 3/1994 |
| WO | WO-91-16307 | 10/1991 |
| WO | WO-95-03319 | 2/1995 |
| WO | WO-02-081437 | 10/2002 |
| WO | WO 2006/026356 | 3/2006 |
| WO | WO 2006/037982 | 4/2006 |
| WO | WO 2007/050087 | 5/2007 |
| WO | WO 2009/070740 | 6/2009 |
| WO | WO 2010/028189 | 3/2010 |
| WO | WO 2010/028190 | 3/2010 |
| WO | WO 2010/135530 | 11/2010 |
| WO | WO 2010/135536 | 11/2010 |
| WO | WO-2011-044140 | 4/2011 |
| WO | WO 2011/159840 | 12/2011 |

OTHER PUBLICATIONS

Carroll et al., Journal of Organic Chemistry, vol. 30(8), 2830-2 (1965).
Dewar, et al., J. Chem. Soc. Perkin Trans I, 1972, Issue 22, 2857-2861.
Emrick, et al., J. Org. Chem. 1960, vol. 25, 1103-1106.
Janczewski, et al., Annals of Univsersitatis Mariae Curie-Sklodowska, 21(7), 65-83, (1966), abstract only.
Janczewski, et al., Roczniki Chemii, 35, 1155 (1961), abstract only.
Thomson, R.H., et al., US Nat. Tech. Inform. Serv., AD Rep. (1971), 36 pp.
International Preliminary Report of Patentability of PCT/US2011/40585 dated Sep. 11, 2012.
International Preliminary Report of Patentability of PCT/US2011/40586 dated Oct. 29, 2012.
ISR of PCT/US2011/40585 dated Feb. 28, 2012.
ISR of PCT/US2011/40586 dated Feb. 9, 2012.
EP 11796396.7 Search Report dated Jun. 4, 2013 (completed May 23, 2013).

*Primary Examiner* — Janet Andres
*Assistant Examiner* — Heidi Reese
(74) *Attorney, Agent, or Firm* — Wilson, Sonsini, Goodrich & Rosati

(57) ABSTRACT

Described herein are compounds useful in the modulation of blood uric acid levels, formulations containing them and methods of using them. In some embodiments, the compounds described herein are used in the treatment or prevention of disorders related to aberrant levels of uric acid.

10 Claims, No Drawings

THIOACETATE COMPOUNDS, COMPOSITIONS AND METHODS OF USE

CROSS-REFERENCE

This application is a continuation patent application of co-pending U.S. application Ser. No. 13/703,890, filed Dec. 12, 2012, pursuant to 35 U.S.C. §371 as a U.S. National Phase Application of International Application Ser. No. PCT/US11/40585, filed Jun. 15, 2011, which claims priority to U.S. Provisional Application 61/355,491, filed Jun. 16, 2010, each of which are incorporated herein by reference in their entirety.

BACKGROUND OF THE INVENTION

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

SUMMARY OF THE INVENTION

In certain embodiments, provided herein are compounds, methods and compositions, e.g., for the modulation of serum uric acid levels (sUA) or the treatment of gout or hyperuricemia in individuals in need thereof. In some embodiments, such compositions comprise and such methods comprise the administration to an individual in need thereof an effective amount of a compound of formula I:

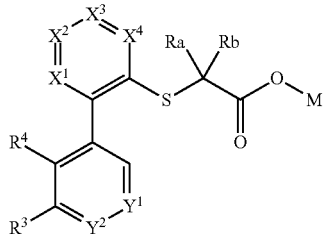

(I)

wherein:
$R^a$ and $R^b$ are selected from H, halogen, $C_1$ to $C_6$ alkyl; or $R^a$ and $R^b$, together with the carbon atom to which they are attached, form a 3-, 4-, 5- or 6-membered ring, optionally containing one or two heteroatoms selected from O, N and S;
M is H, $C_{1-3}$ alkyl or a pharmaceutically acceptable cation;
$X^1$ is N, CH, C(halogen) or C($C_1$-$C_4$ alkyl);
$X^2$ is N or CH;
$X^3$ is N, CH, C(halogen) or C($C_1$-$C_4$ alkyl);
$X^4$ is N or CH; wherein at least one of $X^1$, $X^2$, $X^3$ or $X^4$ is N;
$Y^1$ is N or $CR^1$;
$Y^2$ is N or $CR^2$;
$R^1$ is H, $CF_3$, $CH_3$, $OCH_3$, F or Cl;
$R^2$ is H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{2'}$, $CONH_2$, $CONHR^{2'}$ or $SO_2NH_2$; wherein $R^{2'}$ is H or $C_{1-3}$ alkyl;
$R^3$ is H, halogen, —CN, $C_1$ to $C_6$ alkyl, $C_1$ to $C_6$ alkoxy; and
$R^4$ is H, halogen, —CN, $C_1$ to $C_6$ alkyl, $C_1$ to $C_6$ alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring;

In specific instances:
(i) if $X^2$ and $X^4$ are both N, then $X^1$ cannot be C(halogen); or
if $X^2$ and $X^4$ are both N, then $R^4$ cannot be Cl; or
if $X^2$ and $X^4$ are both N, then $Y^2$ cannot be C—Cl;
(ii) if $X^1$ and $X^2$ are both N, then $X^3$ cannot be C—Cl; and
(iii) the compound of formula (I) is not 1-(3-(4-cyanophenyl)pyridin-4-ylthio)cyclopropanecarboxylic acid.

Provided in certain embodiments, is a compound of formula (I), wherein one of $X^1$, $X^2$, $X^3$ or $X^4$ is N. Certain specific embodiments provided herein describe a compound of formula (I-A), (I-B), (I-C) or (I-D):

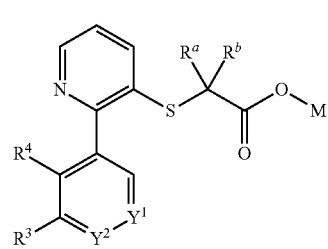

(I-A)

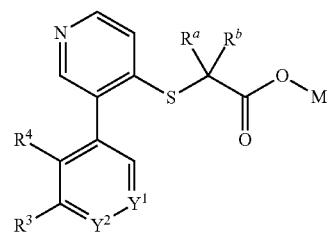

(I-B)

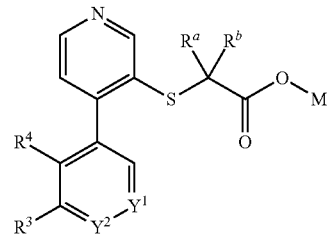

(I-C)

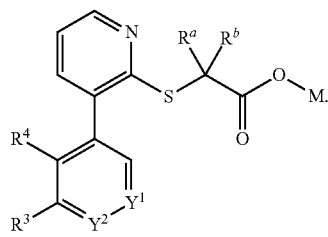

(I-D)

Provided in some embodiments, is a compound of formula (I), wherein two of $X^1$, $X^2$, $X^3$ or $X^4$ are N. Certain specific embodiments provided herein describe a compound of formula (I-E), (I-F) or (I-G):

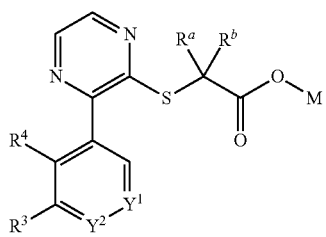
(I-E)

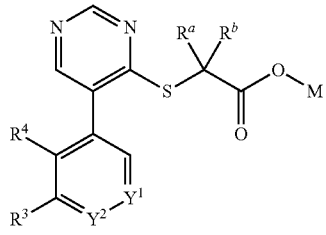
(I-F)

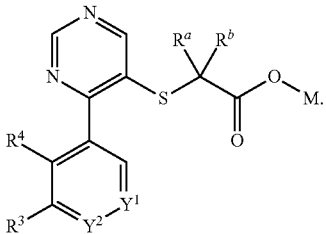
(I-G)

Other specific embodiments provided herein describe a compound of formula (I-H), (I-I) or (I-J):

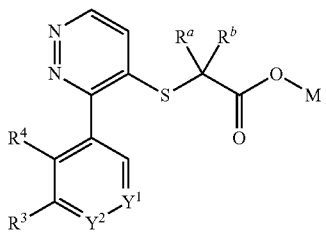
(I-H)

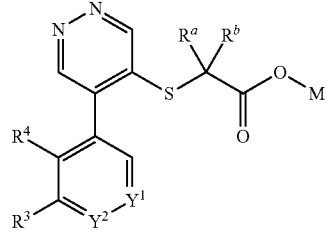
(I-I)

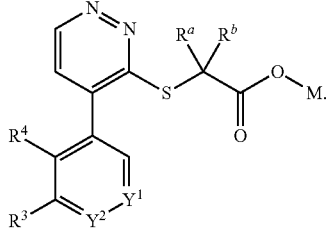
(I-J)

Provided in some embodiments herein, is a compound of formula (I), wherein $R^3$ is H, $CH_3$, $OCH_3$, $CF_3$, F or Cl; and $R^4$ is H, $CH_3$, $OCH_3$, $CF_3$, F or Cl. In certain specific embodiments, $R^3$ and $R^4$ are both H.

Some embodiments provided herein describe a compound of formula (I), wherein $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

Certain embodiments provided herein describe a compound of formula (I), wherein $R^3$ and $R^4$ together with the carbon atoms to which they are attached form an optionally substituted, 6-membered aromatic ring. Certain specific embodiments provided herein describe a compound of formula (I-K):

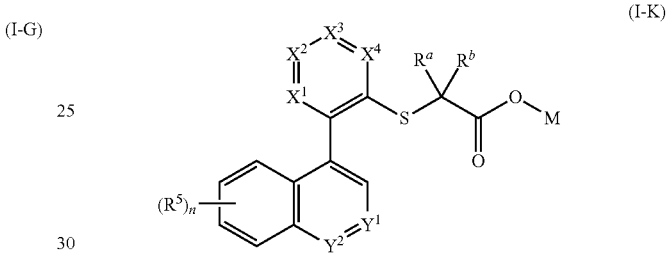
(I-K)

wherein n is 1, 2, 3 or 4; and each $R^5$ is independently selected from H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{5'}$, $CONH_2$, $CONHR^{5'}$ or $SO_2NH_2$; wherein $R^{5'}$ is H or $C_{1-3}$ alkyl.

Provided herein in certain embodiments is a compound of formula (I), wherein $R^a$ is H or $CH_3$; and $R^b$ is H or $CH_3$. In specific embodiments, $R^a$ and $R^b$ are both $CH_3$. Certain specific embodiments provided herein describe a compound of formula (I-L):

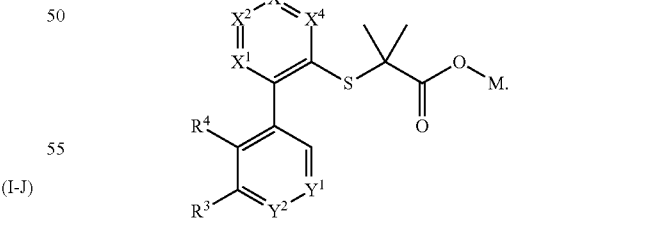
(I-L)

In further or additional embodiments, $X^1$ is CH; $X^2$ is N; $X^3$ is CH; and $X^4$ is CH. In yet further or additional embodiments, $Y^1$ is $CR^1$; and $Y^2$ is $CR^2$.

Certain specific embodiments provided herein describe a compound of formula (I-B), selected from the group consisting of:

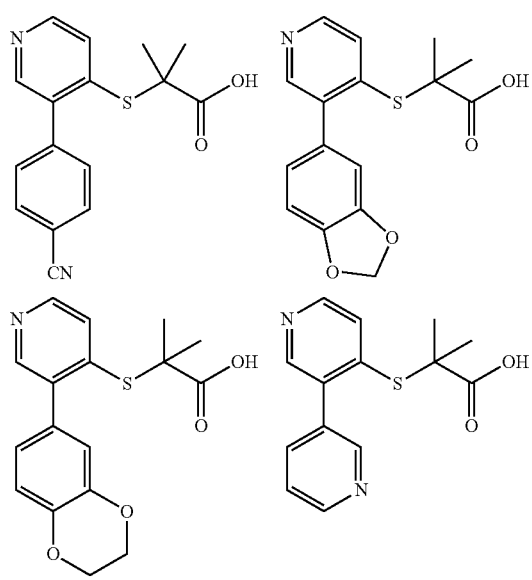
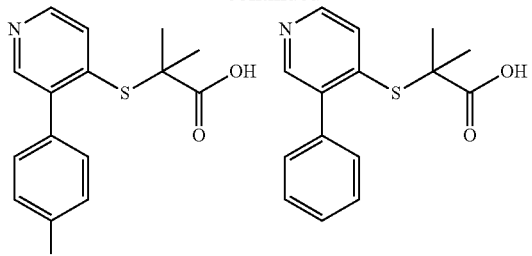
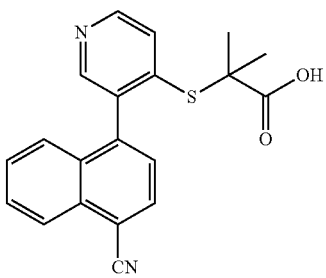
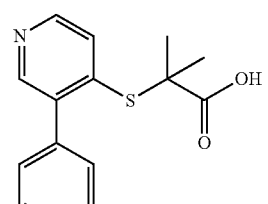
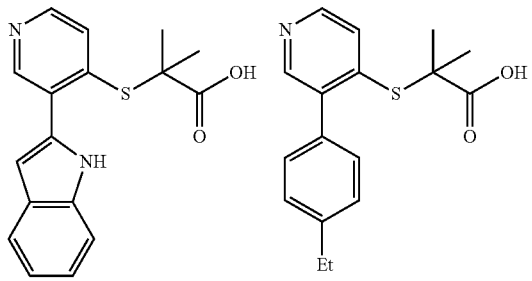
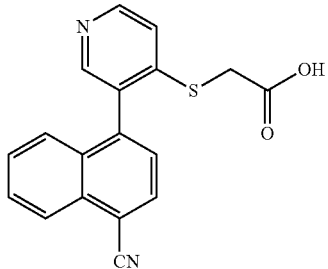
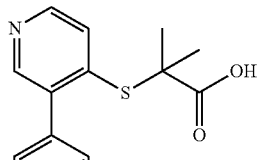
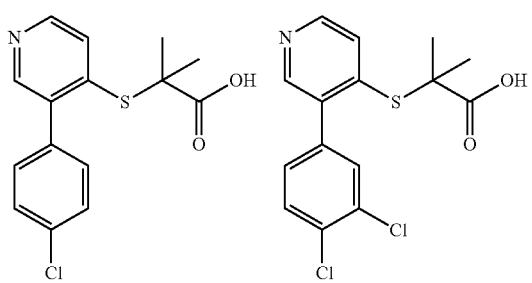
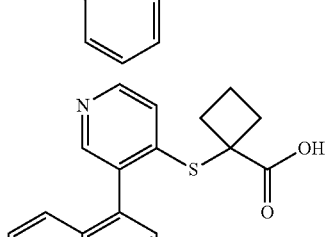
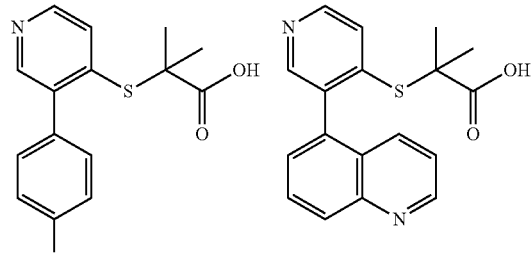
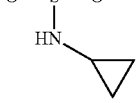

-continued
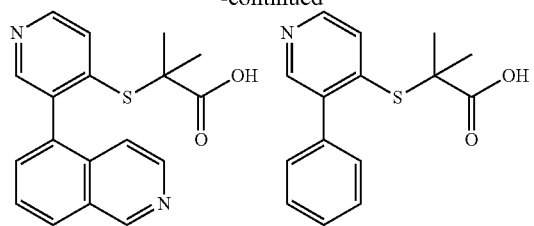
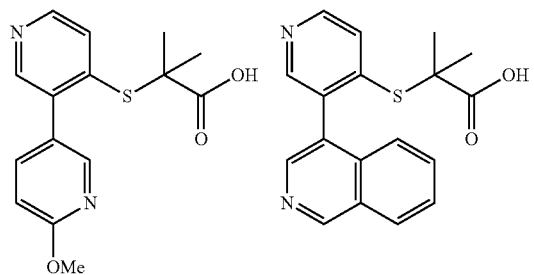
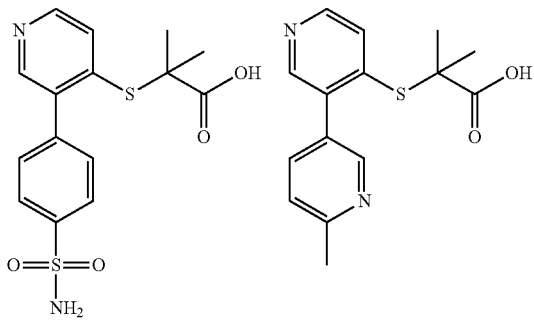
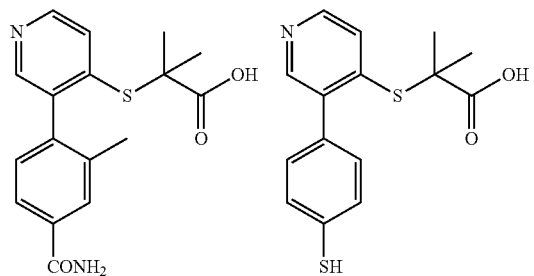
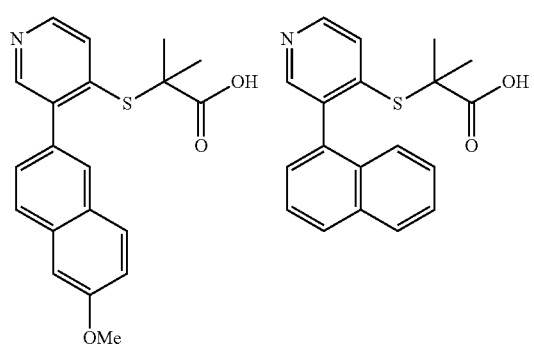
-continued
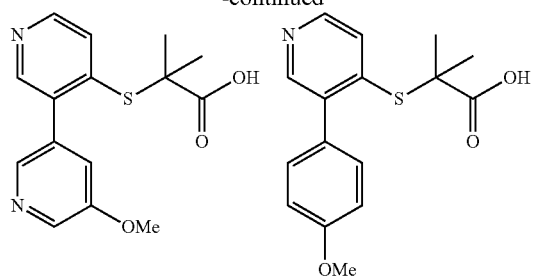
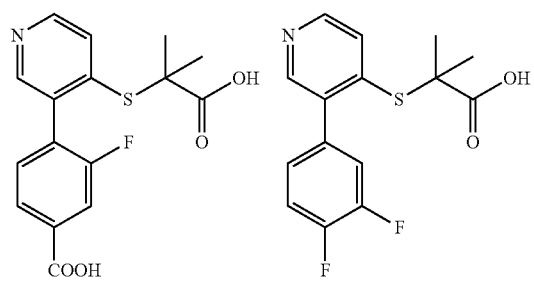
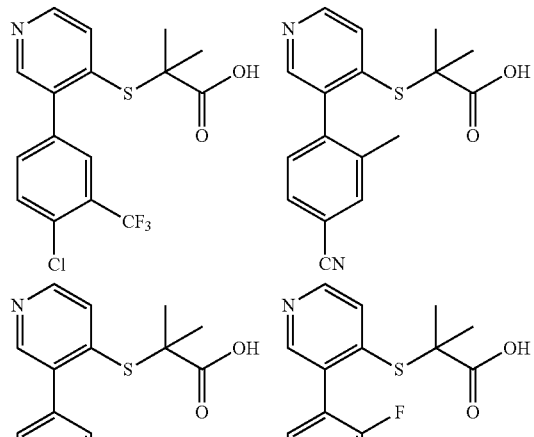
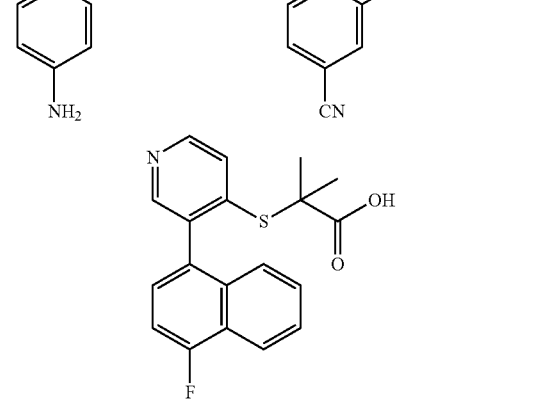
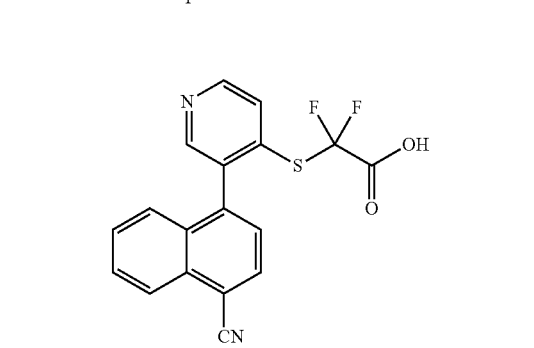

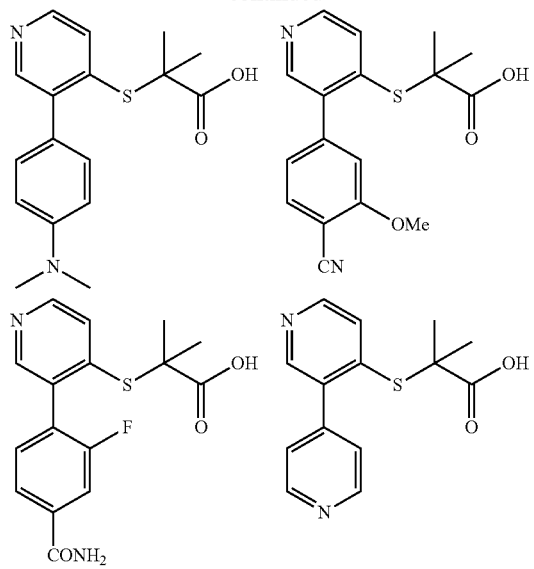
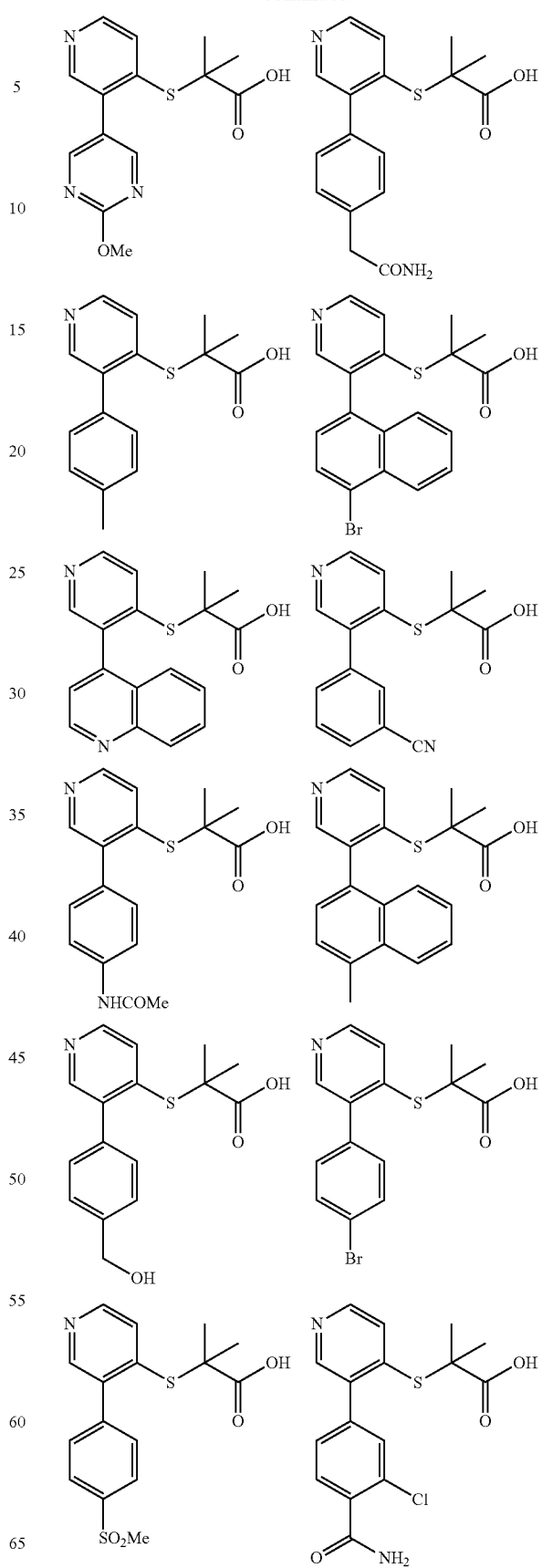

-continued

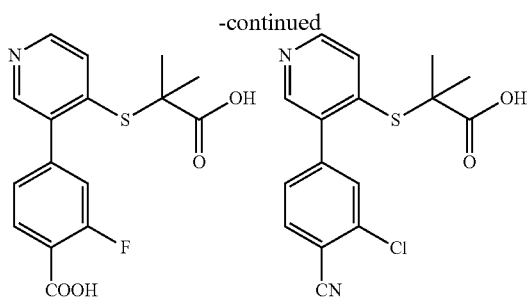

Other specific embodiments provided herein describe a compound of formula (I-M):

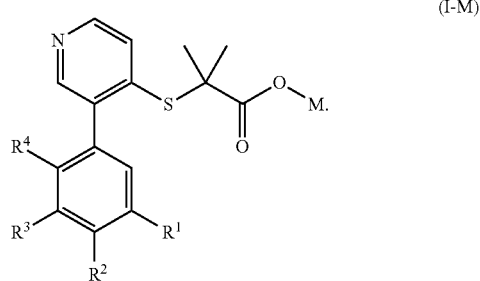

(I-M)

In certain specific embodiments, $R^1$, $R^3$ and $R^4$ are all H.

Provided herein in some embodiments is a compound of formula (I), wherein $R^a$ and $R^b$ together with the carbon atom to which they are attached form a 3-, 4-, 5- or 6-membered ring, optionally containing one or two heteroatoms selected from O, N and S. In certain embodiments, $R^a$ and $R^b$ together with the carbon atom to which they are attached form a 3-, 4-, 5- or 6-membered ring. In certain specific embodiments, $R^a$ and $R^b$ together with the carbon atom to which they are attached form a 3-membered ring.

Provided herein in certain embodiments is a compound of formula (I), wherein M is H. In some embodiments provided herein is a compound of formula (I), wherein M is $C_1$-$C_3$ alkyl. In other embodiments provided herein is a compound of formula (I), wherein M is a pharmaceutically acceptable cation. In specific embodiments, the pharmaceutically acceptable cation is $Na^+$, $Li^+$, $K^+$, $Ca^{2+}$, $Mg^{2+}$, $NH_4^+$, tetramethylammonium, tetraethylammonium, methylamino, dimethylamino, trimethylamino or triethylamino.

Also provided herein in some embodiments is a method of reducing serum uric acid levels in a human, comprising administering to the human an effective amount of a compound of formula (I). Other embodiments provided herein describe a method of treating hyperuricemia in a human with gout, comprising administering to the human an effective amount of a compound of formula (I). Some embodiments provided herein describe a method of treating hyperuricemia in a human, comprising administering to the human an effective amount of a compound of formula (I). Certain embodiments provided herein describe a method of treating gout in a human, comprising administering to the human an effective amount of a compound of formula (I).

Also provided herein in certain embodiments is a method of treating or preventing a condition characterized by abnormal tissue or organ levels of uric acid in an individual comprising administering to the individual an effective amount of a compound of formula (I). In specific embodiments, the condition is gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof. In certain specific embodiments, the condition is gout.

In some embodiments, any of the methods described further comprise administering a second agent effective for the treatment of the gout. In certain embodiments, the second agent is a URAT 1 inhibitor, a xanthine oxidase inhibitor, a xanthine dehydrogenase, a xanthine oxidoreductase inhibitor, or combinations thereof. In certain specific embodiments, the second agent is allopurinol, febuxostat, FYX-051, or combinations thereof.

DETAILED DESCRIPTION OF THE INVENTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described.

Certain Chemical Terminology

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed herein are the standard definitions. Standard techniques can be used for chemical syntheses, chemical analyses, pharmaceutical preparation, formulation, and delivery, and treatment of individuals. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —$CH_2O$— is equivalent to —$OCH_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

In some embodiments, the compounds presented herein possess one or more stereocenters. In some embodiments, the stereocenter is in the R configuration, the S configuration, or combinations thereof. In some embodiments, the compounds presented herein possess one or more double bonds. In some embodiments, the compounds presented herein possess one or more double bonds wherein each double bond exists in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are found, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "reactant," as used herein, refers to a nucleophile or electrophile used to create covalent linkages.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

In certain non-limiting examples, "optionally substituted" indicates that the group is optionally substituted with alkyl, alkenyl, alkynyl, heteroalkyl, heteroalkenyl, heteroalkynyl, haloalkyl, haloalkenyl, haloalkynyl, perhaloalkyl, halo, cycloalkyl, cycloalkenyl, heteroalicycl, aryl, heteroaryl, carbocycl, heterocycl, hydroxy, alkoxy, cyano, cyanoalkyl, carboxyl, sulfhydryl, amino, an amino acid, fused cycloalkyl, spiro cycloalkyl, fused heteroaryl, fused aryl, sulfonyl, sulfinyl, sulfonamidyl, sulfamidyl, phoshonate ester, amido, ether, alkylester, or combinations thereof. In specific instances, a group designated as "optionally substituted" indicates that the group is optionally substituted with hydrogen, hydroxy, nitro, cyano, methylthiol, thiol, azido, methyl, ethyl, propyl, iso-propyl, n-butyl, iso-butyl, sec-butyl, tert-butyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-pentyl, iso-pentyl, neo-pentyl, tent-amyl, hexyl, heptyl, octyl. ethenyl (—CH=$CH_2$), 1-propenyl (—$CH_2$CH=$CH_2$), isopropenyl [—C($CH_3$)=$CH_2$], butenyl, 1,3-butadienyl, ethynyl, 2-propynyl, 2-butyryl, 1,3-butadiynyl, fluoro, chloro, bromo, iodo, fluoromethyl, difluoromethyl, trifluoromethyl, chloromethyl, dichloromethyl, trichloromethyl, bromomethyl, dibromomethyl, tribromomethyl, 1-chloro-1-fluoro-1-iodoethyl, fluoroethyl, bromoethyl, chloroethyl, iodoethyl, fluoropropyl, bromopropyl, chloropropyl, iodopropyl, fluoroethenyl, chloroethenyl, bromoethenyl, iodoethenyl, fluoroethynyl chloroethynyl, bromoethynyl, iodoethynyl, trrifluoroethenyl, trichloroethenyl, tribromoethenyl, trifluoropropynyl, trichloropropynyl, tribromopropynyl, cyclopropyl, cyclobutyl, cyclopentyl, cyclohexyl, cycloheoptyl, spirocyclopropyl, spirocyclobutyl, spirocyclopentyl, pyridinyl, pyranyl, tetrahydrofuranyl, thiofuranyl, aziridinyl, oxiranyl, oxaziridinyl, dioxiranyl, azetidinyl, oxazyl, oxetanyl, theitanyl, pyrrolidinyl, oxolanyl, thiolanyl, oxazolidinyl, thiazolidinyl, decalinyl, bicyclo[2.2.1]heptyl, adamantly, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, cyclohexenyl, cyclopentadienyl, bicyclo[2.2.1]hept-2-ene, methoxy, ethoxy, n-propoxy, isopropoxy, n-butoxy, iso-butoxy, sec-butoxy, tert-butoxy, furanyl, thienyl, acridinyl, phenyl, benzyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl, pyridyl-N-oxide, methyl sulfonyl, ethyl sulfonyl, aminosulfonyl, trifluoromethyl sulfonyl, phosphinic acid, carboxylic acid, amido, amino, methylamine, ethylamine, dimethylamine, diethylamine, aminoethyldimethylamine, aminoethyldiethylamine, methylester, ethylester, propylester, isopropylester, butylester, or combinations thereof.

As used herein, $C_1$-$C_x$ includes $C_1$-$C_2$, $C_1$-$C_3$ ... $C_1$-$C_x$. By way of example only, "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "lower" as used herein in combination with terms such as alkyl, alkenyl or alkynyl, (i.e. "lower alkyl", "lower alkenyl" or "lower alkynyl") refers to an optionally substituted straight-chain, or optionally substituted branched-chain saturated hydrocarbon monoradical having from one to about six carbon atoms, more preferably one to three carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (—CH=CH—), the propenylene isomers (e.g., —$CH_2$CH=CH— and —C($CH_3$)=CH—) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—C≡C—), propargylene (—$CH_2$—C≡C—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)₂—, —O—P(O)₂—, —P(O)₂—O—, —S(O)—, —S(O)₂—, —SnH₂— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof A non-limiting example of a perhaloalkyl group is bromo, chloro, fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "C₃-C₆ cycloalkyl" or "C₃₋₆ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cycloheptyl, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

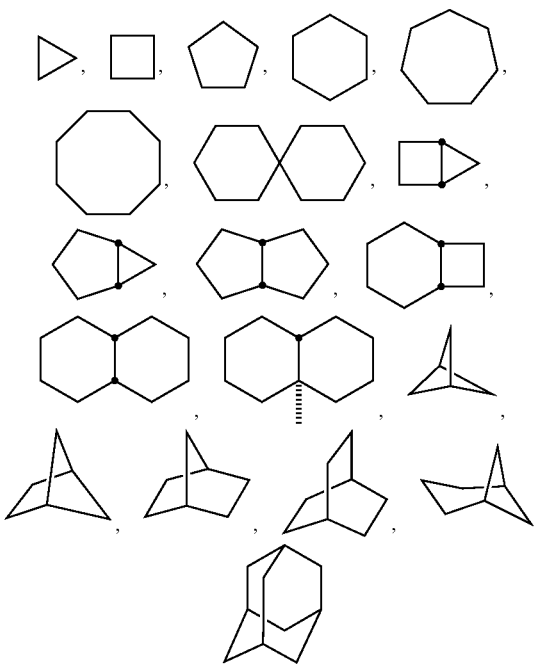

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. A fused cycloalkenyl may contain from two to four fused rings where the ring of attachment is a cycloalkenyl ring, and the other individual rings may be alicyclic, heterocyclic, aromatic, heteroaromatic or any combination thereof. Fused ring systems may be fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

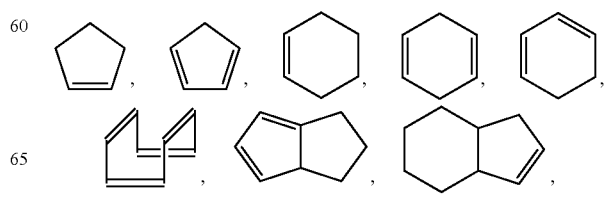

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

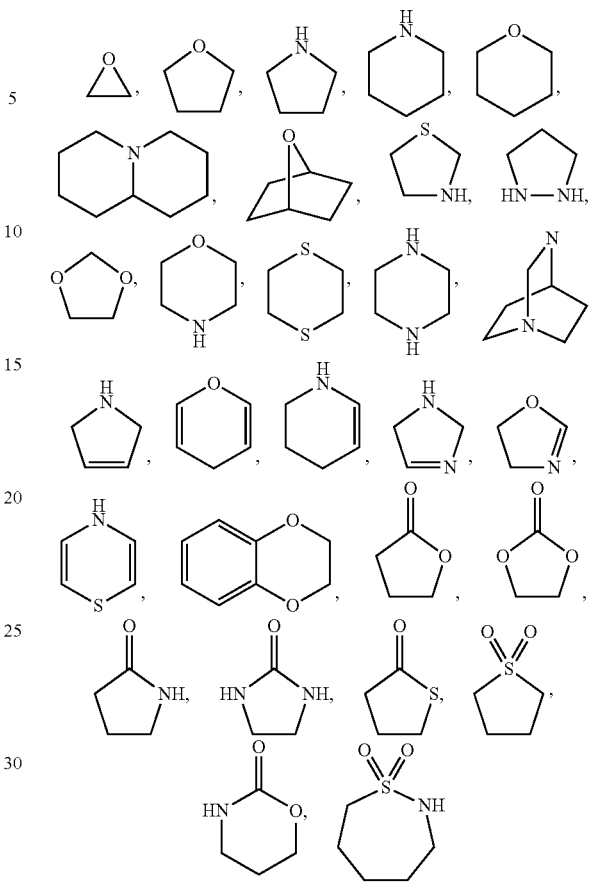

and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2 π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

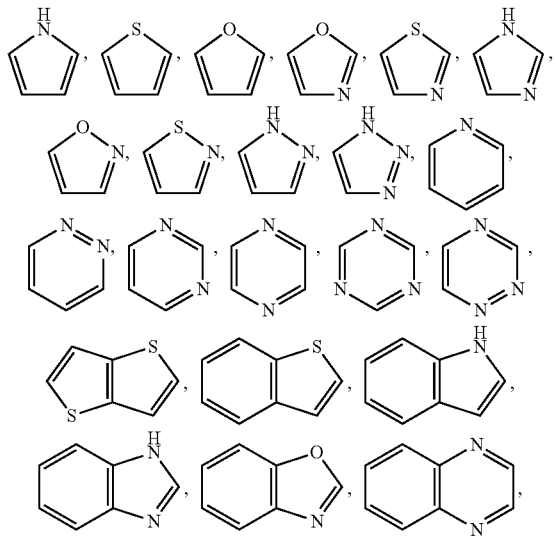

-continued

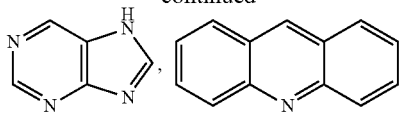

and the like.

The term "heteroarylene" as used herein, alone or in combination, refers to a diradical derived from the above-defined monoradical heteroaryl. Examples include, but are not limited to pyridinyl and pyrimidinyl.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

The term "carbocyclyl" as used herein, alone or in combination, refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —$CH_2CN$.

The term "nitro" as used herein, alone or in combination, refers to the monoradical —$NO_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

The term "amino acid" as used herein refers to a group or compound that consists of an amino group, a carboxyl group, a H atom and a distinctive R group (or side chain). "Amino acid" includes, α-amino acids, β-amino acids, δ-amino acids, and γ-amino acids. α-Amino acids consists of an amino group, a carboxyl group, a H atom and a distinctive R group which is bonded to the α-carbon atom. "Amino acid" includes natural amino acids, unnatural amino acids, amino acid analogs, amino acid mimics, and the like.

In one aspect, the term "amino acid" refers to one of the naturally occurring twenty amino acids (i.e. α-amino acids), as shown below. Amino acids consist of an amino group, a carboxyl group, an H atom and a distinctive R group (or side chain), all of which are bonded to an α-carbon atom. As a result of containing three differing groups on the α-carbon atom, amino acids contain a chiral center, and therefore may exist as either of two optically active enantiomers, the D- and the L-. Naturally occurring acids are found as their L-derivatives.

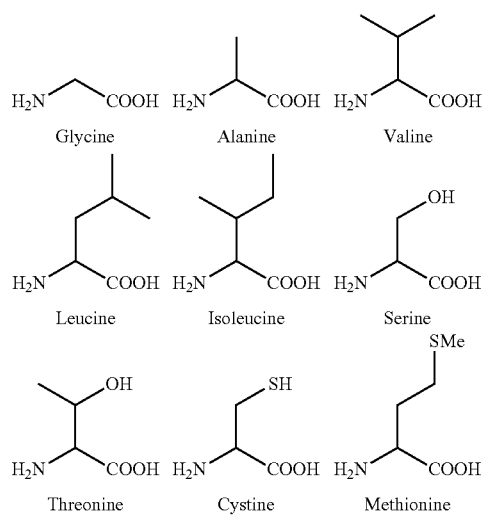

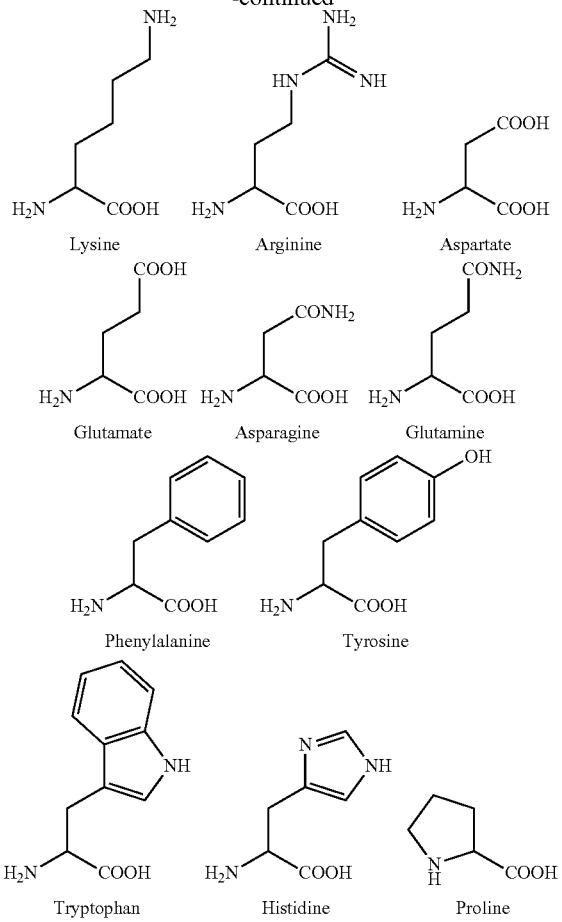

In another aspect, the amino acid is an "unnatural amino acid", "non-natural amino acid", "amino acid analog", "amino acid mimic". "Unnatural amino acid", "non-natural amino acid", "amino acid analog", "amino acid mimic" and the like, as used herein, refer to an amino acid that is not one of the 20 natural amino acids. These terms refer to amino acids wherein the fundamental amino acid molecule has been modified in some way. Such modifications include, though are not limited to side chain variations; substitutions on, or alterations to, the amino-CH-carboxyl backbone; D-enantiomers; combinations thereof and the like.

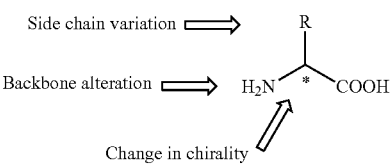

These terms also include, but are not limited to, amino acids which occur naturally but are not naturally incorporated into a growing polypeptide chain, such as, though not limited to N-acetylglucosaminyl-L-serine, N-acetylglucosaminyl-L-threonine, O-phosphotyrosine and the like. Further, these terms also include, but are not limited to, amino acids which do not occur naturally and may be obtained synthetically or may be obtained by modification of natural, naturally occurring or non-natural amino acids.

Illustrative examples of side chain variations include though are not limited to, O-t-butyl-serine, hydroxyproline, 4-chlorophenylalanine, homoserine, methionine sulfoxide, thienylalanine and the like.

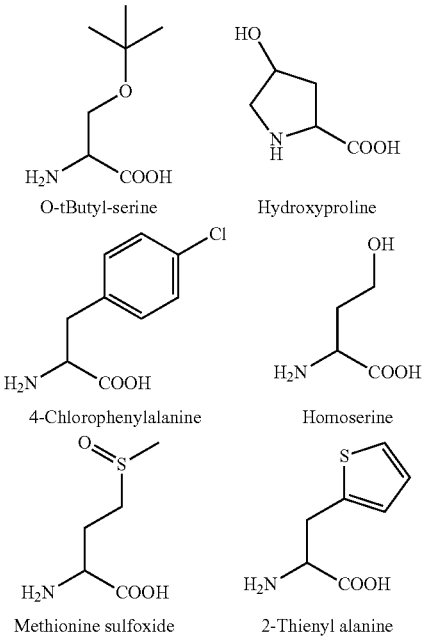

Illustrative examples of backbone alterations include though are not limited to, β-amino acids such as β-alanine, homoproline, alkylation of the amino group, substitution on the α-carbon atom, thiocarboxyls and the like.

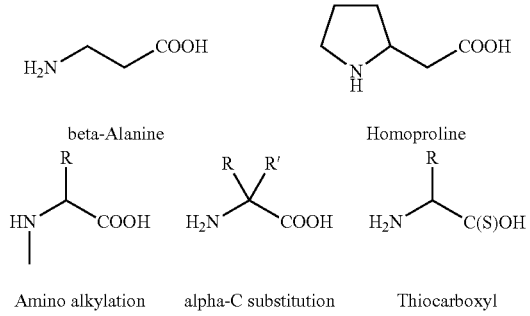

A peptide can be natural or unnatural, and consists of amino acids that are linked together. The terms "natural peptide", "natural polypeptide", "natural protein" and the like, as used herein, refer to a polymer of natural amino acid residues linked by covalent peptide bonds, and include amino acid chains of any length, including full length proteins. The terms "unnatural peptide", "peptide mimic", "peptide analog", "unnatural polypeptide", "unnatural protein" and the like, as used herein, refer to a polymer of amino acid residues of any length, including full length proteins, wherein one or more of the amino acids is an unnatural amino acid, and/or wherein one or more of the amino acids are joined by chemical means other than natural peptide bonds. Illustrative examples of linking groups that can be used as alternatives to the natural peptide bond include, but are not limited to ethylene (—CH$_2$—CH$_2$—), ethynylene (—CH=CH—), ketomethylene (—C(=O)CH$_2$— or —CH$_2$C(=O)—), aminomethylene (—CH$_2$—NH— or —NH—CH$_2$—), methylene ether (—CH$_2$—O— or —O—CH$_2$—), thioether (—CH$_2$—S— or —S—CH$_2$—), thioamide (—C(=S)NH— or —NH—C(=S)—), ester (—C(=O)O— or O—C(=O)—), tetrazole, thiazole and the like.

"Nucleoside" is a glycosylamine consisting of a nucleobase (often referred to simply base) bound to a ribose or deoxyribose sugar. A nucleoside can be a natural nucleoside or an unnatural nucleoside. The term "natural nucleoside" as used herein refers to a nucleobase bound to a ribose or deoxyribose sugar. Examples of these include cytidine, uridine, adenosine, guanosine, thymidine and inosine.

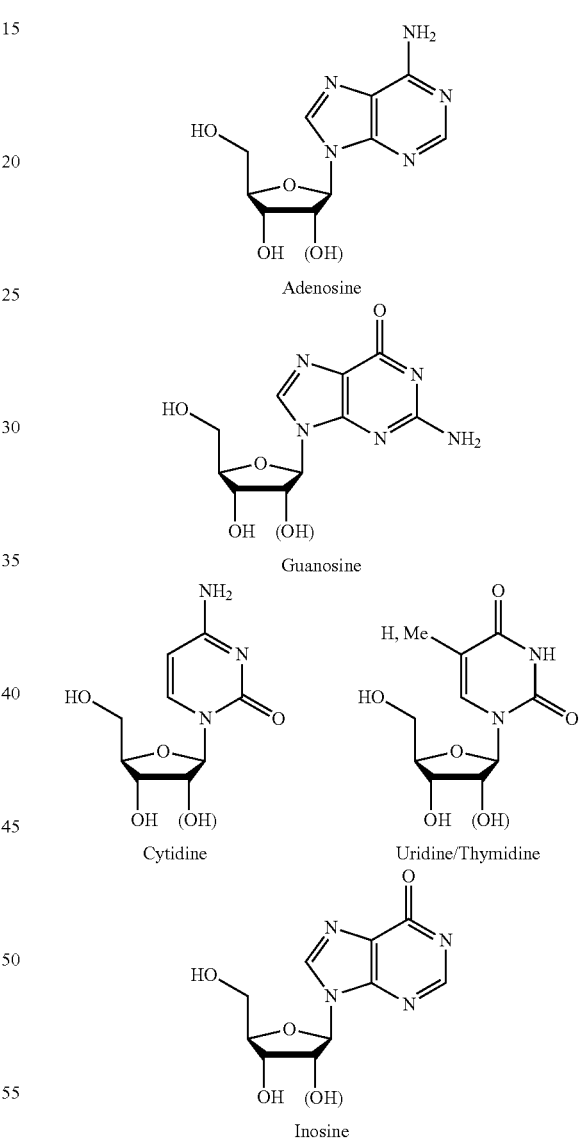

The terms "unnatural nucleoside", "nucleoside analog" and the like, as used herein, refer to a nucleoside that is not one of the 6 nucleosides. These terms refer to nucleosides wherein the fundamental nucleoside molecule has been modified in some way. Such modifications include, though are not limited to base modifications, sugar modifications, alterations of the linkages between the base and sugar, use of alternate stereochemistries; combinations thereof and the like.

The terms "nucleotide", "polynucleotide", "oligonucleotide", "nucleic acid", "nucleic acid polymer" and the like, as used herein, refer to deoxyribonucleotides, deoxyribonucleosides, ribonucleosides or ribonucleotides and polymers thereof in either single- or double-stranded form, including, but not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like).

The term "lipid" as used herein refers to any fat-soluble (lipophilic), naturally-occurring molecule, such as fats, oils, waxes, cholesterol, sterols, fat-soluble vitamins (such as vitamins A, D, E and K), monoglycerides, diglycerides, phospholipids, fatty acid, fatty acid esters, and the like. Lipids can be natural or unnatural. In one aspect the lipid is a fatty acid. Fatty acids are saturated or unsaturated. Saturated fatty acids include, but are not limited to, lauric acid, myristic acid, palmitic acid, stearic acid, arachidic acid. Unsaturated fatty acids include, but are not limited to, palmitoleic acid, oleic acid, linoleic acid, linolenic acid, arachidonic acid.

"Phospholipid" is a type of lipid that is amphipahtic. Phospholipids are a class of lipids and contain a glycerol backbone, where two of the hydroxy groups of the glycerol backbone are esterified with fatty acid (saturated, unsaturated, natural, unnatural), and the third hydroxy is used to form a phosphate ester with phosphoric acid. The phosphate moiety of the resulting phosphatidic acid is further esterified with ethanolamine, choline or serine. Phospholipids are either natural or unnatural. Natural phospholipids include, but are not limited to, plasmalogen, cardiolipin, dipalmitoylphosphatidylcholine, glycerophospholipid, glycerophosphoric acid, lecithin, lysophosphatidic acid, phosphatidylcholine, phosphatidylethanolamine, phosphatidylinositol, phosphatidylinositol (3,4)-bisphosphate, phosphatidylinositol (3,4,5)-trisphosphate, phosphatidylinositol (3,5)-bisphosphate, phosphatidylinositol (4,5)-bisphosphate, phosphatidylinositol 3-phosphate, phosphatidylinositol 4-phosphate, phosphatidylinositol phosphate, phosphatidylmyo-inositol mannosides, phosphatidylserine, platelet-activating factor, sphingomyelin, sphingosyl phosphatide. "Unnatural phospholipids" contain a diglyceride, a phosphate group, and a simple organic molecule such as choline but are prepared by nature.

"Glycoside" as used herein refers to a group comprising any hydrophilic sugar (e.g. sucrose, maltose, glucose, glucuronic acid, and the like). A glycoside is any sugar group bonded through a glycosidic linkage. Glycosides include natural glycosides and unnatural glycosides. Glycosides include asymmetric carbon(s) and exist in L-form or D-form. Natural glycosides preferentially exist in the D-form. Glycosides include monosaccharides, disaccharides, and polysaccharides. Examples of monosaccharides include, but are not limited to, trioses (e.g. glyceraldehyde, dihydroxyacetone), tetroses (e.g. erythrose, threose, erythrulose), pentoses (e.g. arabinose, lyxose, ribose, deoxyribose, xylose, ribulose, xylulose), hexoses (allose, altrose, galactose, glucose, gulose, idose, mannose, talose, fructose, psicose, sorbose, tagatose), heptoses (mannoheptulose, sedoheptulose); octoses (e.g. octolose, 2-keto-3-deoxy-manno-octonate), nonoses (e.g. sialose). Disaccharide include, but are not limited to, sucrose, lactose, maltose, trehalose, cellobiose, kojibiose, nigerose, isomaltose, β,β-trehalose, sophorose, laminaribiose, gentiobiose, turanose, maltulose, palatinose, gentiobiulose, mannobiose, melibiose, melibiulose, rutinose, rutinulose, xylobiose. Polysaccharides include glycans. Aza-sugars are also included within the term "glycoside".

The term "polyethylene glycol" refers to linear or branched polymeric polyether polyols.

Certain Pharmaceutical Terminology

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat," "treating" or "treatment," and other grammatical equivalents as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In preferred embodiments, the compounds and compositions described herein are administered orally.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount may differ from one individual to another. An appropriate "effective" amount in any individual case may be determined using techniques, such as a dose escalation study.

The term "acceptable" as used herein, with respect to a formulation, composition or ingredient, means having no persistent detrimental effect on the general health of the individual being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "prodrug" as used herein, refers to a drug precursor that, following administration to an individual and subsequent absorption, is converted to an active, or a more active species via some process, such as conversion by a metabolic pathway. Thus, the term encompasses any derivative of a compound, which, upon administration to a recipient, is capable of providing, either directly or indirectly, a compound of this invention or a pharmaceutically active metabolite or residue thereof. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. Particularly favored derivatives or prodrugs are those that increase the bioavailability of the compounds of this invention when such compounds are administered to an individual (e.g. by allowing an orally administered compound to be more readily absorbed into the blood) or which enhance delivery of the parent compound to a biological compartment (e.g. the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, excipients and the like.

The term "carrier" as used herein, refers to relatively nontoxic chemical compounds or agents that facilitate the incorporation of a compound into cells or tissues.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to an individual simultaneously in the form of a single entity or dosage. The term "non-fixed combination" means that at least one of the compounds described herein, and at least one co-agent, are administered to an individual as separate entities either simultaneously, concurrently or sequentially with variable intervening time limits, wherein such administration provides effective levels of the two or more compounds in the body of the individual. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single individual, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Compounds

Described herein are compounds of formula (I), metabolites, pharmaceutically acceptable salts, solvates, polymorphs, esters, tautomers or prodrugs thereof.

One embodiment provides a compound of formula (I):

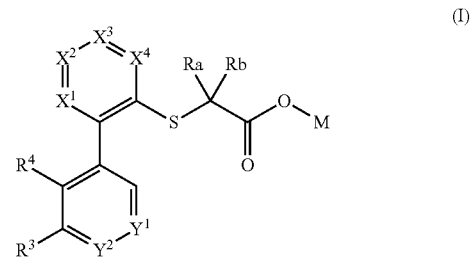

wherein:
$R^a$ and $R^b$ are selected from H, halogen, C1 to C6 alkyl; or $R^a$ and $R^b$, together with the carbon atom to which they are attached, form a 3-, 4-, 5- or 6-membered ring, optionally containing one or two heteroatoms selected from O, N and S;

M is H, $C_{1-3}$ alkyl or a pharmaceutically acceptable cation;

$X^1$ is N, CH, C(halogen) or C(C1-C4 alkyl);

$X^2$ is N or CH;

$X^3$ is N, CH, C(halogen) or C(C1-C4 alkyl);

$X^4$ is N or CH; wherein at least one of $X^1$, $X^2$, $X^3$ or $X^4$ is N;

$Y^1$ is N or $CR^1$;

$Y^2$ is N or $CR^2$;

$R^1$ is H, $CF_3$, $CH_3$, $OCH_3$, F or Cl;

$R^2$ is H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{2'}$, $CONH_2$, $CONHR^{2'}$ or $SO_2NH_2$; wherein $R^{2'}$ is H or $C_{1-3}$ alkyl;

$R^3$ is H, halogen, —CN, C1 to C6 alkyl, C1 to C6 alkoxy; and $R^4$ is H, halogen, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In certain embodiments, provided herein is a compound of formula (I), wherein if $X^2$ and $X^4$ are both N, then $X^1$ is not C(halogen).

In further or alternative embodiments, provided herein is a compound of formula (I), wherein $X^2$ and $X^4$ are both N, and $X^1$ is N, CH, or C(C1-C4 alkyl). In further or alternative embodiments, provided herein is a compound of formula (I), wherein $X^2$ is N, $X^4$ is CH, and $X^1$ is N, CH, C(halogen) or C(C1-C4 alkyl). In still further or alternative embodiments, provided herein is a compound of formula (I), wherein $X^2$ is CH, $X^4$ is N, and $X^1$ is N, CH, C(halogen) or C(C1-C4 alkyl). In certain embodiments, $X^2$ and $X^4$ are both CH, and $X^1$ is N, CH, C(halogen) or C(C1-C4 alkyl).

In further or alternative embodiments, provided herein is a compound of formula (I), wherein $X^2$ and $X^4$ are both N, and $X^1$ is N. In some embodiments, $X^2$ and $X^4$ are both N, and $X^1$ is CH. In other embodiments, $X^2$ and $X^4$ are both N, and $X^1$ is C(C1-C4 alkyl). In still further or alternative embodiments, $X^2$ is CH or N and $X^1$ is N, CH, C(halogen) or C(C1-C4 alkyl). In still further or alternative embodiments, provided herein is a compound of formula (I), wherein $X^4$ is CH or N, and $X^1$ is N, CH, C(halogen) or C(C1-C4 alkyl).

In further or alternative embodiments, $X^2$ and $X^4$ are both CH, and $X^1$ is N. In some embodiments, $X^2$ and $X^4$ are both CH, and $X^1$ is CH. In certain embodiments, $X^2$ and $X^4$ are both CH, and $X^1$ is C(halogen). In other embodiments, $X^2$ and $X^4$ are both CH, and $X^1$ is C(C1-C4 alkyl).

In further or alternative embodiments, $X^2$ is CH, $X^4$ is N, and $X^1$ is N. In some embodiments, $X^2$ is CH, $X^4$ is N, and $X^1$ is CH. In certain embodiments, $X^2$ is CH, $X^4$ is N, and $X^1$ is C(halogen). In other embodiments, $X^2$ is CH, $X^4$ is N, and $X^1$ is C(C1-C4 alkyl).

In further or alternative embodiments, $X^2$ is N, $X^4$ is CH, and $X^1$ is N. In some embodiments, $X^2$ is N, $X^4$ is CH, and $X^1$ is CH. In certain embodiments, $X^2$ is N, $X^4$ is CH, and $X^1$ is C(halogen). In other embodiments, $X^2$ is N, $X^4$ is CH, and $X^1$ is C(C1-C4 alkyl).

In further or alternative embodiments, $X^2$ is N and $X^1$ is N. In some embodiments, $X^2$ is N and $X^1$ is CH. In certain embodiments, $X^2$ is N and $X^1$ is C(halogen). In other embodiments, $X^2$ is N and $X^1$ is C(C1-C4 alkyl). In further or alternative embodiments, $X^2$ is CH and $X^1$ is N. In some embodiments, $X^2$ is CH and $X^1$ is CH. In certain embodiments, $X^2$ is CH and $X^1$ is C(halogen). In other embodiments, $X^2$ is CH and $X^1$ is C(C1-C4 alkyl).

In further or alternative embodiments, $X^4$ is N and $X^1$ is N. In some embodiments, $X^4$ is N and $X^1$ is CH. In certain embodiments, $X^4$ is N and $X^1$ is C(halogen). In other embodiments, $X^4$ is N and $X^1$ is C(C1-C4 alkyl). In further or alternative embodiments, $X^4$ is CH and $X^1$ is N. In some embodiments, $X^4$ is CH and $X^1$ is CH. In certain embodiments, $X^4$ is CH and $X^1$ is C(halogen). In other embodiments, $X^4$ is CH and $X^1$ is C(C1-C4 alkyl).

In certain embodiments, provided herein is a compound of formula (I), wherein if $X^2$ and $X^4$ are both N, then $R^4$ is not Cl.

In further or alternative embodiments, provided herein is a compound of formula (I), wherein $X^2$ and $X^4$ are both N, and $R^4$ is H, halogen, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring. In further or alternative embodiments, provided herein is a compound of formula (I), wherein $X^2$ and $X^4$ are both CH, and $R^4$ is H, halogen, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring. In some embodiments, $X^2$ is CH, $X^4$ is N, and $R^4$ is H, halogen, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring. In other embodiments, $X^2$ is N, $X^4$ is CH, and $R^4$ is H, halogen, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In further or alternative embodiments, provided herein is a compound of formula (I), wherein $X^2$ and $X^4$ are both N, and $R^4$ is H, fluoro, iodo, bromo, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring. In certain embodiments, $X^2$ and $X^4$ are both CH, and $R^4$ is H, fluoro, chloro, iodo, bromo, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring. In some embodiments, $X^2$ is CH, $X^4$ is N, and $R^4$ is H, fluoro, chloro, iodo, bromo, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring. In other embodiments, $X^2$ is N, $X^4$ is CH, and $R^4$ is H, fluoro, chloro, iodo, bromo, —CN, C1 to C6 alkyl, C1 to C6 alkoxy; or $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In further or alternative embodiments, provided herein is a compound of formula (I), wherein $X^2$ and $X^4$ are both N, and $R^4$ is H. In some embodiments, $X^2$ and $X^4$ are both N, and $R^4$ is fluoro. In other embodiments, $X^2$ and $X^4$ are both N, and $R^4$ is iodo. In certain, $X^2$ and $X^4$ are both N, and $R^4$ is bromo. In some embodiments, $X^2$ and $X^4$ are both N, and $R^4$ is —CN. In certain specific embodiments, $X^2$ and $X^4$ are both N, and $R^4$ is C1 to C6 alkyl. In some instances, $X^2$ and $X^4$ are both N, and $R^4$ is C1 to C6 alkoxy. In other embodiments, $X^2$ and $X^4$ are both N, and $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In further or alternative embodiments, provided herein is a compound of formula (I), wherein $X^2$ and $X^4$ are both CH, and $R^4$ is H. In some embodiments, $X^2$ and $X^4$ are both CH, and $R^4$ is fluoro. In some embodiments, $X^2$ and $X^4$ are both CH, and $R^4$ is chloro. In other embodiments, $X^2$ and $X^4$ are both CH, and $R^4$ is iodo. In certain, $X^2$ and $X^4$ are both CH, and $R^4$ is bromo. In some embodiments, $X^2$ and $X^4$ are both CH, and $R^4$ is —CN. In certain specific embodiments, $X^2$ and $X^4$ are both CH, and $R^4$ is C1 to C6 alkyl. In some instances, $X^2$ and $X^4$ are both CH, and $R^4$ is C1 to C6 alkoxy. In other embodiments, $X^2$ and $X^4$ are both CH, and $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In further or alternative embodiments, provided herein is a compound of formula (I), wherein $X^2$ is CH, $X^4$ is N, and $R^4$ is H. In some embodiments, $X^2$ is CH, $X^4$ is N, and $R^4$ is fluoro. In some embodiments, $X^2$ is CH, $X^4$ is N, and $R^4$ is chloro. In other embodiments, $X^2$ is CH, $X^4$ is N, and $R^4$ is iodo. In certain, $X^2$ is CH, $X^4$ is N, and $R^4$ is bromo. In some embodiments, $X^2$ is CH, $X^4$ is N, and $R^4$ is —CN. In certain specific embodiments, $X^2$ is CH, $X^4$ is N, and $R^4$ is C1 to C6 alkyl. In some instances, $X^2$ is CH, $X^4$ is N, and $R^4$ is C1 to C6 alkoxy. In other embodiments, $X^2$ is CH, $X^4$ is N, and $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In further or alternative embodiments, provided herein is a compound of formula (I), wherein $X^2$ is N, $X^4$ is CH, and $R^4$ is H. In some embodiments, $X^2$ is N, $X^4$ is CH, and $R^4$ is fluoro. In some embodiments, $X^2$ is N, $X^4$ is CH, and $R^4$ is chloro. In other embodiments, $X^2$ is N, $X^4$ is CH, and $R^4$ is iodo. In certain, $X^2$ is N, $X^4$ is CH, and $R^4$ is bromo. In some embodiments, $X^2$ is N, $X^4$ is CH, and $R^4$ is —CN. In certain specific embodiments, $X^2$ is N, $X^4$ is CH, and $R^4$ is C1 to C6 alkyl. In some instances, $X^2$ is N, $X^4$ is CH, and $R^4$ is C1 to C6 alkoxy. In other embodiments, $X^2$ is N, $X^4$ is CH, and $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

In certain embodiments, provided herein is a compound of formula (I), wherein if $X^2$ and $X^4$ are both N, then $Y^2$ is not C—Cl.

In further or alternative embodiments, provided herein is a compound of formula (I), wherein $X^2$ and $X^4$ are both N, and $Y^2$ is N or $CR^2$, wherein $R^2$ is H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, F, CN, COOH, $COOR^{2'}$, $CONH_2$, $CONHR^{2'}$ or $SO_2NH_2$; wherein $R^{2'}$ is H or $C_{1-3}$ alkyl. In further or alternative embodiments, provided herein is a compound of formula (I), wherein $X^2$ and $X^4$ are both CH, and $Y^2$ is N or $CR^2$, wherein $R^2$ is H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{2'}$, $CONH_2$, $CONHR^{2'}$ or $SO_2NH_2$; wherein $R^{2'}$ is H or $C_{1-3}$ alkyl. In some embodiments, $X^2$ is N, $X^4$ is CH, and $Y^2$ is N or $CR^2$, wherein $R^2$ is H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{2'}$, $CONH_2$, $CONHR^{2'}$ or $SO_2NH_2$; wherein $R^{2'}$ is H or $C_{1-3}$ alkyl. In other embodiments, $X^2$ is CH, $X^4$ is N, and $Y^2$ is N or $CR^2$, wherein $R^2$ is H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{2'}$, $CONH_2$, $CONHR^{2'}$ or $SO_2NH_2$; wherein $R^{2'}$ is H or $C_{1-3}$ alkyl.

In further or alternative embodiments, provided herein is a compound of formula (I), wherein $X^2$ and $X^4$ are both N, and $Y^2$ is N. In some embodiments, $X^2$ and $X^4$ are both N, and $Y^2$ is $CR^2$, wherein $R^2$ is H. In some embodiments, $X^2$ and $X^4$ are both N, and $Y^2$ is $CR^2$, wherein $R^2$ is methyl. In some embodiments, $X^2$ and $X^4$ are both N, and $Y^2$ is $CR^2$, wherein $R^2$ is ethyl. In other embodiments, $X^2$ and $X^4$ are both N, and $Y^2$ is $CR^2$, wherein $R^2$ is propyl. In certain embodiments, $X^2$ and $X^4$ are both N, and $Y^2$ is $CR^2$, wherein $R^2$ is isopropyl. In some embodiments, $X^2$ and $X^4$ are both N, and $Y^2$ is $CR^2$, wherein $R^2$ is tert-butyl. In some embodiments, $X^2$ and $X^4$ are both N, and $Y^2$ is $CR^2$, wherein $R^2$ is cyclopropyl. In other embodiments, $X^2$ and $X^4$ are both N, and $Y^2$ is $CR^2$, wherein $R^2$ is cyclobutyl. In some embodiments, $X^2$ and $X^4$ are both N, and $Y^2$ is $CR^2$, wherein $R^2$ is $CF_3$. In specific embodiments, $X^2$ and $X^4$ are both N, and $Y^2$ is $CR^2$, wherein $R^2$ is OH. In certain embodiments, $X^2$ and $X^4$ are both N, and $Y^2$ is $CR^2$, wherein $R^2$ is $OCH_3$. In some embodiments, $X^2$ and $X^4$ are both N, and $Y^2$ is $CR^2$, wherein $R^2$ is ethoxy. In other embodiments, $X^2$ and $X^4$ are both N, and $Y^2$ is $CR^2$, wherein $R^2$ is SH. In some embodiments, $X^2$ and $X^4$ are both N, and $Y^2$ is $CR^2$, wherein $R^2$ is $SCH_3$. In some embodiments, $X^2$ and $X^4$ are both N, and $Y^2$ is $CR^2$, wherein $R^2$ is $SCH_2CH_3$. In some embodiments, $X^2$ and $X^4$ are both N, and $Y^2$ is $CR^2$, wherein $R^2$ is $CH_2OH$. In certain embodiments, $X^2$ and $X^4$ are both N, and $Y^2$ is $CR^2$, wherein $R^2$ is $C(CH_3)_2OH$. In further or additional embodiments, $X^2$ and $X^4$ are both N, and $Y^2$ is $CR^2$, wherein $R^2$ is F. In some embodiments, $X^2$ and $X^4$ are both N, and $Y^2$ is $CR^2$, wherein $R^2$ is CN. In some embodiments, $X^2$ and $X^4$ are both N, and $Y^2$ is $CR^2$, wherein $R^2$ is COOH. In certain specific embodiments, $X^2$ and $X^4$ are both N, and $Y^2$ is $CR^2$, wherein $R^2$ is $COOR^{2'}$, wherein $R^{2'}$ is H or $C_{1-3}$ alkyl. In some embodiments, $X^2$ and $X^4$ are both N, and $Y^2$ is $CR^2$, wherein $R^2$ is $CONH_2$. In other embodiments, $X^2$ and $X^4$ are both N, and $Y^2$ is $CR^2$, wherein $R^2$ is $CONHR^{2'}$, wherein $R^{2'}$ is H or $C_{1-3}$ alkyl. In certain embodiments, $X^2$ and $X^4$ are both N, and $Y^2$ is $CR^2$, wherein $R^2$ is $SO_2NH_2$.

In further or alternative embodiments, provided herein is a compound of formula (I), wherein $X^2$ and $X^4$ are both CH, and $Y^2$ is N. In some embodiments, $X^2$ and $X^4$ are both CH, and $Y^2$ is $CR^2$, wherein $R^2$ is H. In some embodiments, $X^2$ and $X^4$ are both CH, and $Y^2$ is $CR^2$, wherein $R^2$ is methyl. In other embodiments, $X^2$ and $X^4$ are both CH, and $Y^2$ is $CR^2$, wherein $R^2$ is ethyl. In some embodiments, $X^2$ and $X^4$ are both CH, and $Y^2$ is $CR^2$, wherein $R^2$ is propyl. In certain embodiments, $X^2$ and $X^4$ are both CH, and $Y^2$ is $CR^2$, wherein $R^2$ is isopropyl. In some embodiments, $X^2$ and $X^4$ are both CH, and $Y^2$ is $CR^2$, wherein $R^2$ is tert-butyl. In other embodiments, $X^2$ and $X^4$ are both CH, and $Y^2$ is $CR^2$, wherein $R^2$ is cyclopropyl. In certain embodiments, $X^2$ and $X^4$ are both CH, and $Y^2$ is $CR^2$, wherein $R^2$ is cyclobutyl. In some embodiments, $X^2$ and $X^4$ are both CH, and $Y^2$ is $CR^2$, wherein $R^2$ is $CF_3$. In other embodiments, $X^2$ and $X^4$ are both CH, and $Y^2$ is $CR^2$, wherein $R^2$ is OH. In some embodiments, $X^2$ and $X^4$ are both CH, and $Y^2$ is $CR^2$, wherein $R^2$ is $OCH_3$. In some embodiments, $X^2$ and $X^4$ are both CH, and $Y^2$ is $CR^2$, wherein $R^2$ is ethoxy. In other embodiments, $X^2$ and $X^4$ are both CH, and $Y^2$ is $CR^2$, wherein $R^2$ is SH. In some embodiments, $X^2$ and $X^4$ are both CH, and $Y^2$ is $CR^2$, wherein $R^2$ is $SCH_3$. In certain embodiments, $X^2$ and $X^4$ are both CH, and $Y^2$ is $CR^2$, wherein $R^2$ is $SCH_2CH_3$. In some embodiments, $X^2$ and $X^4$ are both CH, and $Y^2$ is $CR^2$, wherein $R^2$ is $CH_2OH$. In certain embodiments, $X^2$ and $X^4$ are both CH, and $Y^2$ is $CR^2$, wherein $R^2$ is $C(CH_3)_2OH$. In some instances, $X^2$ and $X^4$ are both CH, and $Y^2$ is $CR^2$, wherein $R^2$ is F. In certain embodiments, $X^2$ and $X^4$ are both CH, and $Y^2$ is $CR^2$, wherein $R^2$ is Cl. In some embodiments, $X^2$ and $X^4$ are both CH, and $Y^2$ is $CR^2$, wherein $R^2$ is CN. In other embodiments, $X^2$ and $X^4$ are both CH, and $Y^2$ is $CR^2$, wherein $R^2$ is COOH. In some embodiments, $X^2$ and $X^4$ are both CH, and $Y^2$ is $CR^2$, wherein $R^2$ is $COOR^{2'}$, wherein $R^{2'}$ is H or $C_{1-3}$ alkyl. In certain embodiments, $X^2$ and $X^4$ are both CH, and $Y^2$ is $CR^2$, wherein $R^2$ is $CONH_2$. In some embodiments, $X^2$ and $X^4$ are both CH, and $Y^2$ is $CR^2$, wherein $R^2$ is $CONHR^{2'}$, wherein $R^{2'}$ is H or $C_{1-3}$ alkyl. In other embodiments, $X^2$ and $X^4$ are both CH, and $Y^2$ is $CR^2$, wherein $R^2$ is $SO_2NH_2$.

In further or alternative embodiments, provided herein is a compound of formula (I), wherein $X^2$ is CH, $X^4$ is N, and $Y^2$ is N. In some embodiments, $X^2$ is CH, $X^4$ is N, and $Y^2$ is $CR^2$, wherein $R^2$ is H. In some embodiments, $X^2$ is CH, $X^4$ is N, and $Y^2$ is $CR^2$, wherein $R^2$ is methyl. In other embodiments, $X^2$ is CH, $X^4$ is N, and $Y^2$ is $CR^2$, wherein $R^2$ is ethyl. In some embodiments, $X^2$ is CH, $X^4$ is N, and $Y^2$ is $CR^2$, wherein $R^2$ is propyl. In certain embodiments, $X^2$ is CH, $X^4$ is N, and $Y^2$ is $CR^2$, wherein $R^2$ is isopropyl. In some embodiments, $X^2$ is CH, $X^4$ is N, and $Y^2$ is $CR^2$, wherein $R^2$ is tert-butyl. In other embodiments, $X^2$ is CH, $X^4$ is N, and $Y^2$ is $CR^2$, wherein $R^2$ is cyclopropyl. In certain embodiments, $X^2$ is CH, $X^4$ is N, and $Y^2$ is $CR^2$, wherein $R^2$ is cyclobutyl. In some embodiments, $X^2$ is CH, $X^4$ is N, and $Y^2$ is $CR^2$, wherein $R^2$ is $CF_3$. In other embodiments, $X^2$ is CH, $X^4$ is N, and $Y^2$ is $CR^2$, wherein $R^2$ is OH. In some embodiments, $X^2$ is CH, $X^4$ is N, and $Y^2$ is $CR^2$, wherein $R^2$ is $OCH_3$. In some embodiments, $X^2$ is CH, $X^4$ is N, and $Y^2$ is $CR^2$, wherein $R^2$ is ethoxy. In other embodiments, $X^2$ is CH, $X^4$ is N, and $Y^2$ is $CR^2$, wherein $R^2$ is SH. In some embodiments, $X^2$ is CH, $X^4$ is N, wherein $R^2$ is $SCH_3$. In certain embodiments, $X^2$ is CH, $X^4$ is N, and $Y^2$ is $CR^2$, wherein $R^2$ is $SCH_2CH_3$. In some embodiments, $X^2$ is CH, $X^4$ is N, and $Y^2$ is $CR^2$, wherein $R^2$ is $CH_2OH$. In certain embodiments, $X^2$ is CH, $X^4$ is N, and $Y^2$ is $CR^2$, wherein $R^2$ is $C(CH_3)_2OH$. In some instances, $X^2$ is CH, $X^4$ is N, and $Y^2$ is $CR^2$, wherein $R^2$ is F. In certain embodiments, $X^2$ is CH, $X^4$ is N, and $Y^2$ is $CR^2$, wherein $R^2$ is Cl. In some embodiments, $X^2$ is CH, $X^4$ is N, and $Y^2$ is $CR^2$, wherein $R^2$ is CN. In other embodiments, $X^2$ is CH, $X^4$ is N, and $Y^2$ is $CR^2$, wherein $R^2$ is COOH. In some embodiments, $X^2$ is CH, $X^4$ is N, and $Y^2$ is $CR^2$, wherein $R^2$ is $COOR^{2'}$, wherein $R^{2'}$ is H or $C_{1-3}$ alkyl. In certain embodiments $X^2$ is CH, $X^4$ is N, and $Y^2$ is $CR^2$, wherein $R^2$ is $CONH_2$. In some embodiments, $X^2$ is CH, $X^4$ is N, and $Y^2$ is $CR^2$, wherein $R^2$ is $CONHR^{2'}$, wherein $R^{2'}$ is H or $C_{1-3}$ alkyl. In other embodiments, $X^2$ is CH, $X^4$ is N, and $Y^2$ is $CR^2$, wherein $R^2$ is $SO_2NH_2$.

In further or alternative embodiments, provided herein is a compound of formula (I), wherein $X^2$ is N, $X^4$ is CH, and $Y^2$ is N. In some embodiments, $X^2$ is N, $X^4$ is CH, and $Y^2$ is $CR^2$, wherein $R^2$ is H. In some embodiments, $X^2$ is N, $X^4$ is CH, and $Y^2$ is $CR^2$, wherein $R^2$ is methyl. In other embodiments, $X^2$ is N, $X^4$ is CH, and $Y^2$ is $CR^2$, wherein $R^2$ is ethyl. In some embodiments, $X^2$ is N, $X^4$ is CH, and $Y^2$ is $CR^2$, wherein $R^2$ is propyl. In certain embodiments, $X^2$ is N, $X^4$ is CH, and $Y^2$ is $CR^2$, wherein $R^2$ is isopropyl. In some embodiments, $X^2$ is N, $X^4$ is CH, and $Y^2$ is $CR^2$, wherein $R^2$ is tert-butyl. In other embodiments, $X^2$ is N, $X^4$ is CH, and $Y^2$ is $CR^2$, wherein $R^2$ is cyclopropyl. In certain embodiments, $X^2$ is N, $X^4$ is CH, and $Y^2$ is $CR^2$, wherein $R^2$ is cyclobutyl. In some embodiments, $X^2$ is N, $X^4$ is CH, and $Y^2$ is $CR^2$, wherein $R^2$ is $CF_3$. In other embodiments, $X^2$ is N, $X^4$ is CH, and $Y^2$ is $CR^2$, wherein $R^2$ is OH. In some embodiments, $X^2$ is N, $X^4$ is CH, and $Y^2$ is $CR^2$, wherein $R^2$ is $OCH_3$. In some embodiments, $X^2$ is N, $X^4$ is CH, and $Y^2$ is $CR^2$, wherein $R^2$ is ethoxy. In other embodiments, $X^2$ is N, $X^4$ is CH, and $Y^2$ is $CR^2$, wherein $R^2$ is SH. In some embodiments, $X^2$ is N, $X^4$ is CH, wherein $R^2$ is $SCH_3$. In certain embodiments, $X^2$ is N, $X^4$ is CH, and $Y^2$ is $CR^2$, wherein $R^2$ is $SCH_2CH_3$. In some embodiments, $X^2$ is N, $X^4$ is CH, and $Y^2$ is $CR^2$, wherein $R^2$ is $CH_2OH$. In certain embodiments, $X^2$ is N, $X^4$ is CH, and $Y^2$ is $CR^2$, wherein $R^2$ is $C(CH_3)_2OH$. In some instances, $X^2$ is N, $X^4$ is CH, and $Y^2$ is $CR^2$, wherein $R^2$ is F. In certain embodiments, $X^2$ is N, $X^4$ is CH, and $Y^2$ is $CR^2$, wherein $R^2$ is Cl. In some embodiments, $X^2$ is N, $X^4$ is CH, and $Y^2$ is $CR^2$, wherein $R^2$ is CN. In other embodiments, $X^2$ is N, $X^4$ is CH, and $Y^2$ is $CR^2$, wherein $R^2$ is COOH. In some embodiments, $X^2$ is N, $X^4$ is CH, and $Y^2$ is $CR^2$, wherein $R^2$ is $COOR^{2'}$, wherein $R^{2'}$ is H or $C_{1-3}$ alkyl. In certain embodiments $X^2$ is N, $X^4$ is CH, and $Y^2$ is $CR^2$, wherein $R^2$ is $CONH_2$. In some embodiments, $X^2$ is N, $X^4$ is CH, and $Y^2$ is $CR^2$, wherein $R^2$ is $CONHR^{2'}$, wherein $R^{2'}$ is H or $C_{1-3}$ alkyl. In other embodiments, $X^2$ is N, $X^4$ is CH, and $Y^2$ is $CR^2$, wherein $R^2$ is $SO_2NH_2$.

In certain embodiments, provided herein is a compound of formula (I), wherein if $X^1$ and $X^2$ are both N, then $X^3$ is not C—Cl.

In further or alternative embodiments, provided herein is a compound of formula (I), wherein $X^1$ and $X^2$ are both N, and $X^3$ is N, CH, C—F, or C(C1-C4 alkyl). In further or alternative embodiments, provided herein is a compound of formula (I), wherein $X^1$ is N, $X^2$ is CH, and $X^3$ is N, CH, C(halogen) or C(C1-C4 alkyl). In still further or alternative embodiments, provided herein is a compound of formula (I), wherein $X^1$ is CH, $X^2$ is N, and $X^3$ is N, CH, C(halogen) or C(C1-C4 alkyl). In certain embodiments, $X^1$ and $X^2$ are both CH, and $X^3$ is N, CH, C(halogen) or C(C1-C4 alkyl).

In further or alternative embodiments, provided herein is a compound of formula (I), wherein $X^1$ and $X^2$ are both N, and $X^3$ is N. In some embodiments, $X^1$ and $X^2$ are both N, and $X^3$ is CH. In some embodiments, $X^1$ and $X^2$ are both N, and $X^3$ is C—F. In some embodiments, $X^1$ and $X^2$ are both N, and $X^3$ is C—Br. In some embodiments, $X^1$ and $X^2$ are both N, and $X^3$ is C—I. In other embodiments, $X^1$ and $X^2$ are both N, and $X^3$ is C(C1-C4 alkyl). In still further or alternative embodiments, $X^1$ is CH or N and $X^3$ is N, CH, C(halogen) or C(C1-C4 alkyl). In still further or alternative embodiments, provided herein is a compound of formula (I), wherein $X^2$ is CH or N, and $X^3$ is N, CH, C(halogen) or C(C1-C4 alkyl).

In further or alternative embodiments, $X^1$ and $X^2$ are both CH, and $X^3$ is N. In some embodiments, $X^1$ and $X^2$ are both CH, and $X^3$ is CH. In certain embodiments, $X^1$ and $X^2$ are both CH, and $X^3$ is C(halogen). In certain embodiments, $X^1$ and $X^2$ are both CH, and $X^3$ is C—F. In certain embodiments, $X^1$ and $X^2$ are both CH, and $X^3$ is C—Cl. In certain embodiments, $X^1$ and $X^2$ are both CH, and $X^3$ is C—Br. In certain embodiments, $X^1$ and $X^2$ are both CH, and $X^3$ is C—I. In other embodiments, $X^1$ and $X^2$ are both CH, and $X^3$ is C(C1-C4 alkyl).

In further or alternative embodiments, $X^1$ is CH, $X^2$ is N, and $X^3$ is N. In some embodiments, $X^1$ is CH, $X^2$ is N, and $X^3$ is CH. In certain embodiments, $X^1$ is CH, $X^2$ is N, and $X^3$ is C(halogen). In certain embodiments, $X^1$ is CH, $X^2$ is N, and $X^3$ is C—F. In certain embodiments, $X^1$ is CH, $X^2$ is N, and $X^3$ is C—Cl. In certain embodiments, $X^1$ is CH, $X^2$ is N, and $X^3$ is C—Br. In certain embodiments, $X^1$ is CH, $X^2$ is N, and $X^3$ is C—I. In other embodiments, $X^1$ is CH, $X^2$ is N, and $X^3$ is C(C1-C4 alkyl).

In further or alternative embodiments, $X^1$ is N, $X^2$ is CH, and $X^3$ is N. In some embodiments, $X^1$ is N, $X^2$ is CH, and $X^3$ is CH. In certain embodiments, $X^1$ is N, $X^2$ is CH, and $X^3$ is C(halogen). In certain embodiments, $X^1$ is N, $X^2$ is CH, and $X^3$ is C—F. In certain embodiments, $X^1$ is N, $X^2$ is CH, and $X^3$ is C—Cl. In certain embodiments, $X^1$ is N, $X^2$ is CH, and $X^3$ is C—Br. In certain embodiments, $X^1$ is N, $X^2$ is CH, and $X^3$ is C—I. In other embodiments, $X^1$ is N, $X^2$ is CH, and $X^3$ is C(C1-C4 alkyl).

In further or alternative embodiments, $X^1$ is N and $X^3$ is N. In some embodiments, $X^1$ is N and $X^3$ is CH. In certain embodiments, $X^1$ is N and $X^3$ is C(halogen). In certain embodiments, $X^1$ is N and $X^3$ is C—F. In certain embodiments, $X^1$ is N and $X^3$ is C—Cl. In certain embodiments, $X^1$ is N and $X^3$ is C—Br. In certain embodiments, $X^1$ is N and $X^3$ is C—I. In other embodiments, $X^1$ is N and $X^3$ is C(C1-C4 alkyl).

In further or alternative embodiments, $X^1$ is CH and $X^3$ is N. In some embodiments, $X^1$ is CH and $X^3$ is CH. In certain embodiments, $X^1$ is CH and $X^3$ is C(halogen). In certain embodiments, $X^1$ is CH and $X^3$ is C—F. In certain embodiments, $X^1$ is CH and $X^3$ is C—Cl. In certain embodiments, $X^1$ is CH and $X^3$ is C—Br. In certain embodiments, $X^1$ is CH and $X^3$ is C—I. In other embodiments, $X^1$ is CH and $X^3$ is C(C1-C4 alkyl).

In further or alternative embodiments, $X^1$ is C(halogen) and $X^3$ is N. In some embodiments, $X^1$ is C(halogen) and $X^3$ is CH. In certain embodiments, $X^1$ is C(halogen) and $X^3$ is C(halogen). In certain embodiments, $X^1$ is C(halogen) and $X^3$ is C—F. In certain embodiments, $X^1$ is C(halogen) and $X^3$ is C—Cl. In certain embodiments, $X^1$ is C(halogen) and $X^3$ is C—Br. In certain embodiments, $X^1$ is C(halogen) and $X^3$ is C—I. In other embodiments, $X^1$ is C(halogen) and $X^3$ is C(C1-C4 alkyl).

In further or alternative embodiments, $X^1$ is C(C1-C4 alkyl) and $X^3$ is N. In some embodiments, $X^1$ is C(C1-C4 alkyl) and $X^3$ is CH. In certain embodiments, $X^1$ is C(C1-C4 alkyl) and $X^3$ is C(halogen). In certain embodiments, $X^1$ is C(C1-C4 alkyl) and $X^3$ is C—F. In certain embodiments, $X^1$ is C(C1-C4 alkyl) and $X^3$ is C—Cl. In certain embodiments, $X^1$ is C($C_1$-$C_4$ alkyl) and $X^3$ is C—Br. In certain embodiments, $X^1$ is C(C1-C4 alkyl) and $X^3$ is C—I. In other embodiments, $X^1$ is C(C1-C4 alkyl) and $X^3$ is C(C1-C4 alkyl).

In further or alternative embodiments, $X^2$ is CH and $X^3$ is N. In some embodiments, $X^2$ is CH and $X^3$ is CH. In certain embodiments, $X^2$ is CH and $X^3$ is C(halogen). In certain embodiments, $X^2$ is CH and $X^3$ is C—F. In certain embodiments, $X^2$ is CH and $X^3$ is C—Cl. In certain embodiments, $X^2$ is CH and $X^3$ is C—Br. In certain embodiments, $X^2$ is CH and $X^3$ is C—I. In other embodiments, $X^2$ is CH and $X^3$ is C(C1-C4 alkyl).

In further or alternative embodiments, $X^2$ is N and $X^3$ is N. In some embodiments, $X^2$ is N and $X^3$ is CH. In certain embodiments, $X^2$ is N and $X^3$ is C(halogen). In certain embodiments, $X^2$ is N and $X^3$ is C—F. In certain embodiments, $X^2$ is N and $X^3$ is C—Cl. In certain embodiments, $X^2$ is N and $X^3$ is C—Br. In certain embodiments, $X^2$ is N and $X^3$ is C—I. In other embodiments, $X^2$ is N and $X^3$ is C(C1-C4 alkyl).

In certain embodiments, the compound of formula (I) is not 1-(3-(4-cyanophenyl)pyridin-4-ylthio)cyclopropanecarboxylic acid.

Another embodiment provides a compound of formula (I), wherein one of $X^1$, $X^2$, $X^3$ or $X^4$ is N.

Another embodiment provides a compound of formula (I) having the structure of formula (I-A), (I-B), (I-C) or (I-D):

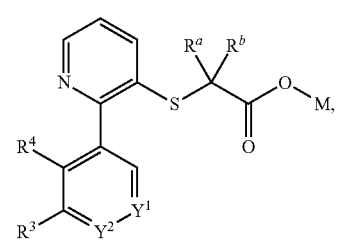

(I-A)

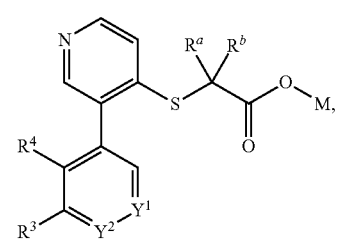

(I-B)

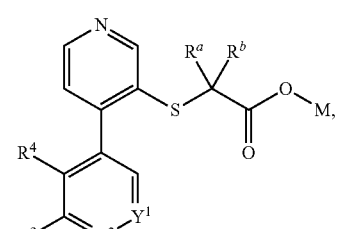

(I-C)

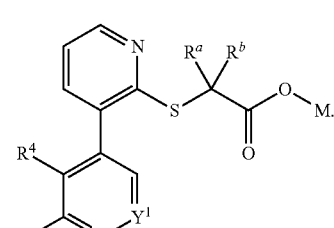

(I-D)

Another embodiment provides a compound of formula (I) wherein two of $X^1$, $X^2$, $X^3$ or $X^4$ are N.

Another embodiment provides a compound of formula (I) having the structure of formula (I-E), (I-F) or (I-G):

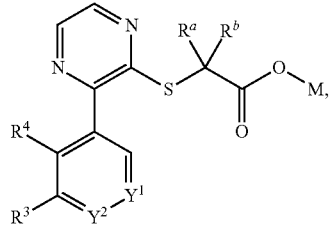
(I-E)

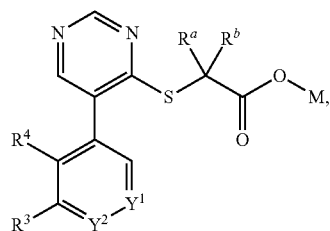
(I-F)

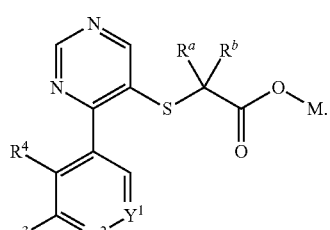
(I-G)

Another embodiment provides a compound of formula (I) having the structure of formula (I-H), (I-I) or (I-J):

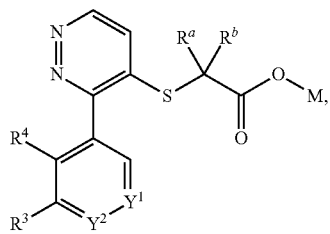
(I-H)

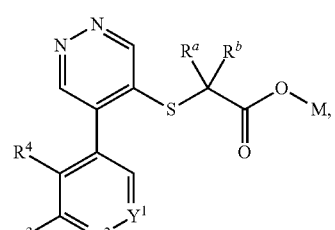
(I-I)

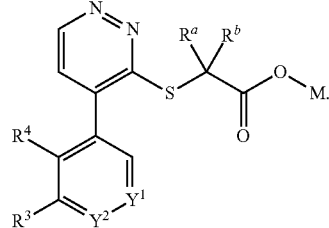
(I-J)

Another embodiment provides a compound of formula (I) wherein $R^3$ is H, $CH_3$, $OCH_3$, $CF_3$, F or Cl; and $R^4$ is H, $CH_3$, $OCH_3$, $CF_3$, F or Cl.

Another embodiment provides a compound of formula (I) wherein $R^3$ and $R^4$ are both H.

Another embodiment provides a compound of formula (I) wherein $R^3$ and $R^4$ together with the carbon atoms to which they are attached form an optionally substituted 5- or 6-membered ring, optionally containing one or two heteroatoms selected from O, N and S, wherein said 5- or 6-membered ring maybe a saturated, an unsaturated or an aromatic ring.

Another embodiment provides a compound of formula (I) wherein $R^3$ and $R^4$ together with the carbon atoms to which they are attached form an optionally substituted, 6-membered aromatic ring.

Another embodiment provides a compound of formula (I) having the structure of formula (I-K):

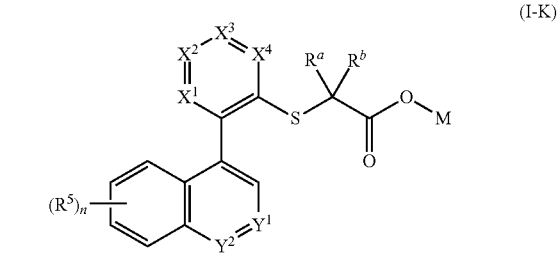
(I-K)

wherein n is 1, 2, 3 or 4; and
each $R^5$ is independently selected from H, methyl, ethyl, propyl, isopropyl, tert-butyl, cyclopropyl, cyclobutyl, $CF_3$, OH, $OCH_3$, ethoxy, SH, $SCH_3$, $SCH_2CH_3$, $CH_2OH$, $C(CH_3)_2OH$, Cl, F, CN, COOH, $COOR^{5'}$, $CONH_2$, $CONHR^{5'}$ or $SO_2NH_2$; wherein $R^5$ is H or $C_{1-3}$ alkyl.

Another embodiment provides a compound of formula (I) wherein $R^a$ is H or $CH_3$; and $R^b$ is H or $CH_3$.

Another embodiment provides a compound of formula (I) wherein $R^a$ and $R^b$ are both $CH_3$.

Another embodiment provides a compound of formula (I) having the structure of formula (I-L):

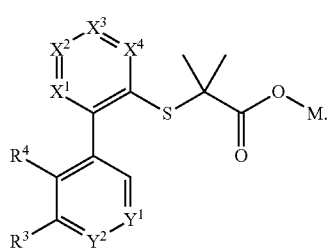
(I-L)

Another embodiment provides a compound of formula (I-L) wherein $X^1$ is CH; $X^2$ is N; $X^3$ is CH; and $X^4$ is CH.
Another embodiment provides a compound of formula (I-L) wherein $Y^1$ is $CR^1$; and $Y^2$ is $CR^2$.
Another embodiment provides a compound of formula (I-L) selected from:
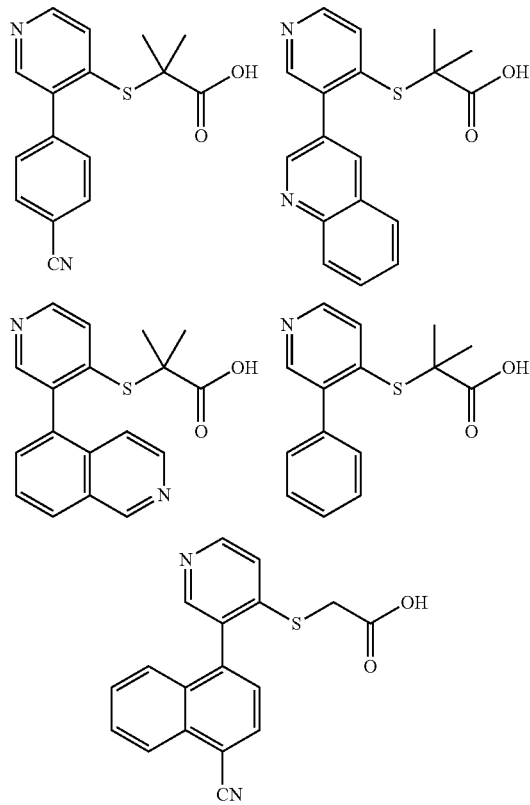
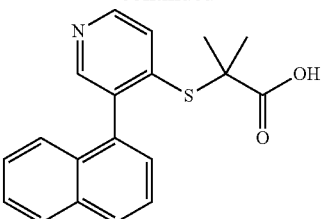
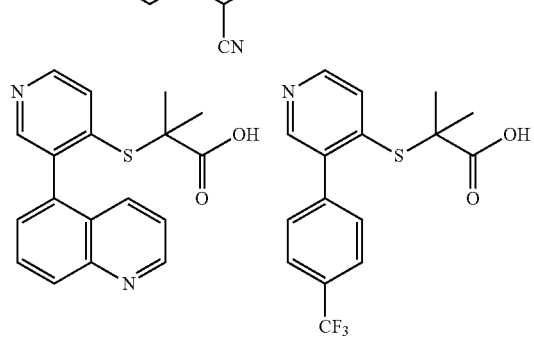
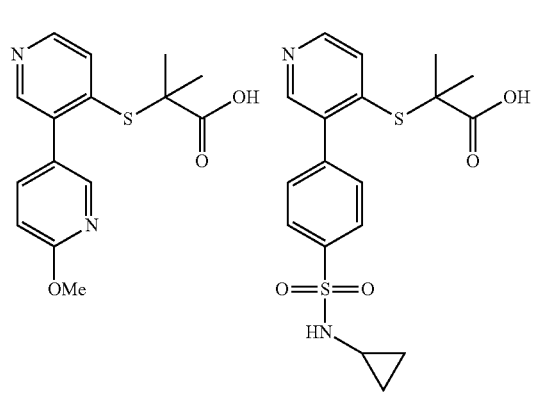
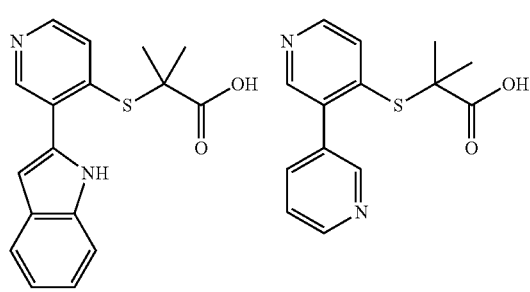
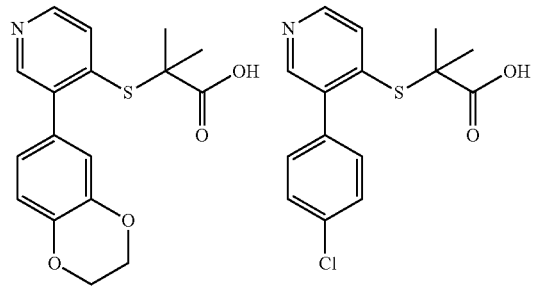
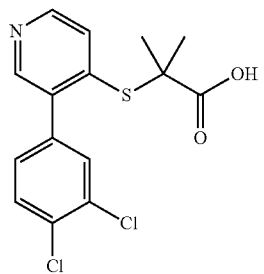
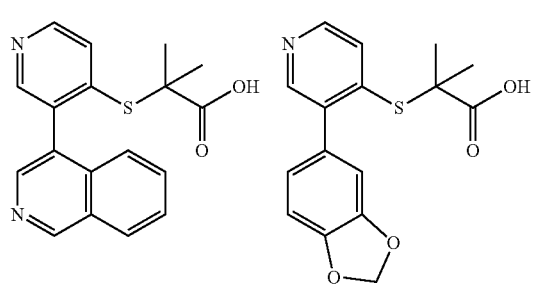

-continued
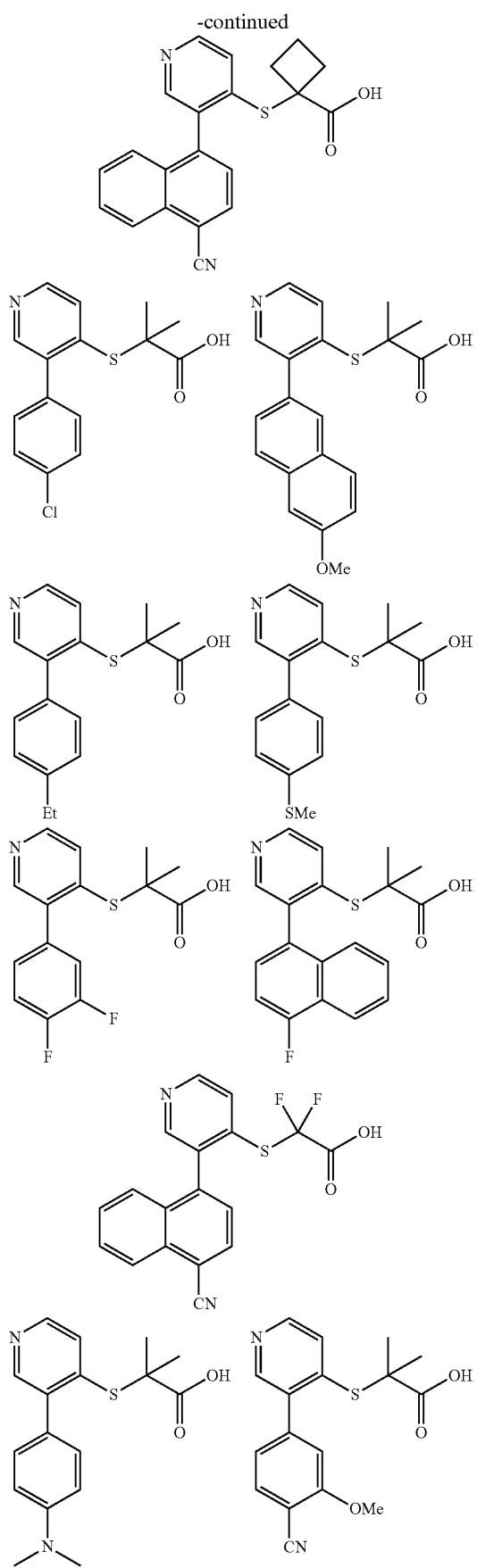
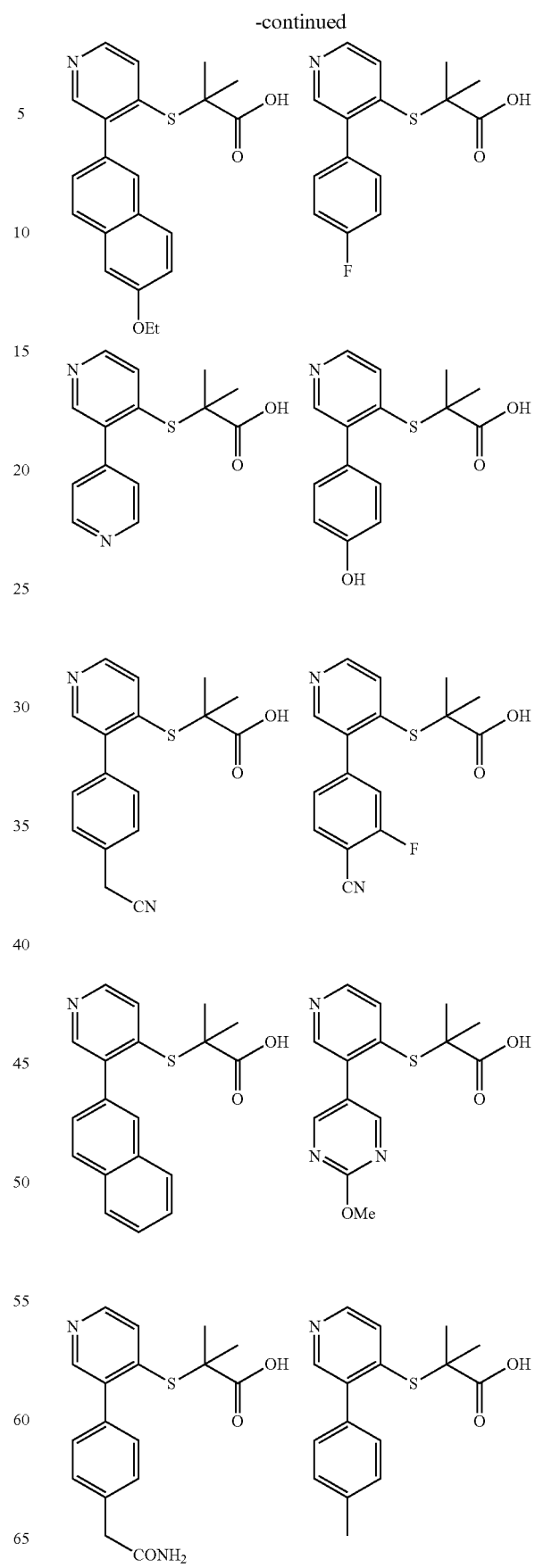

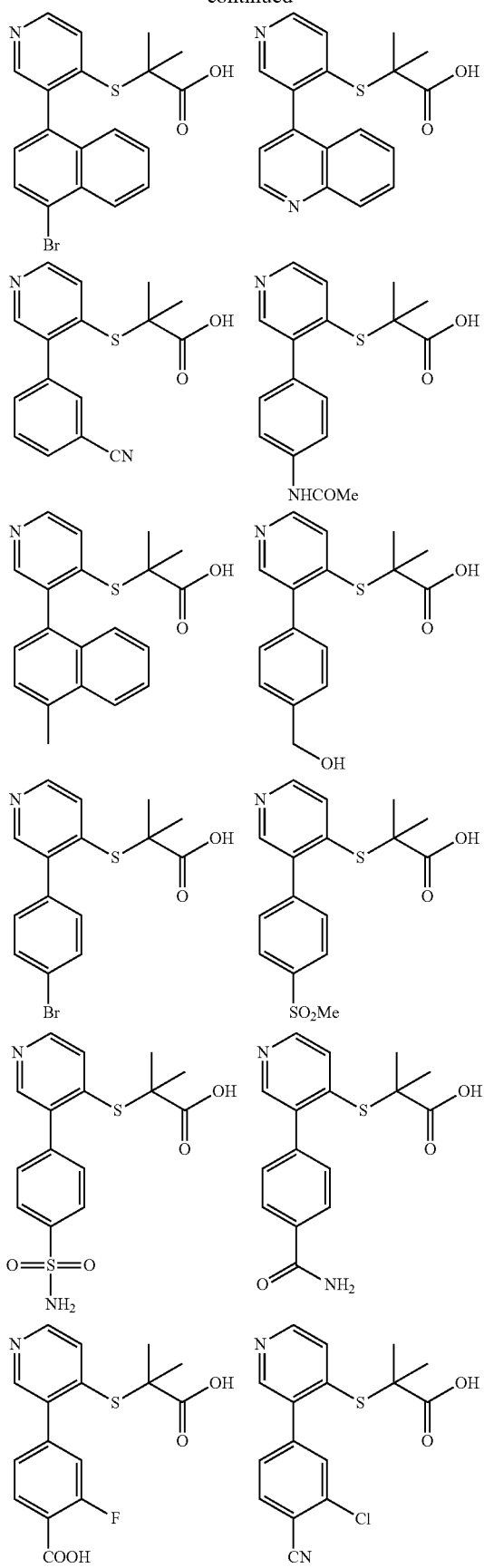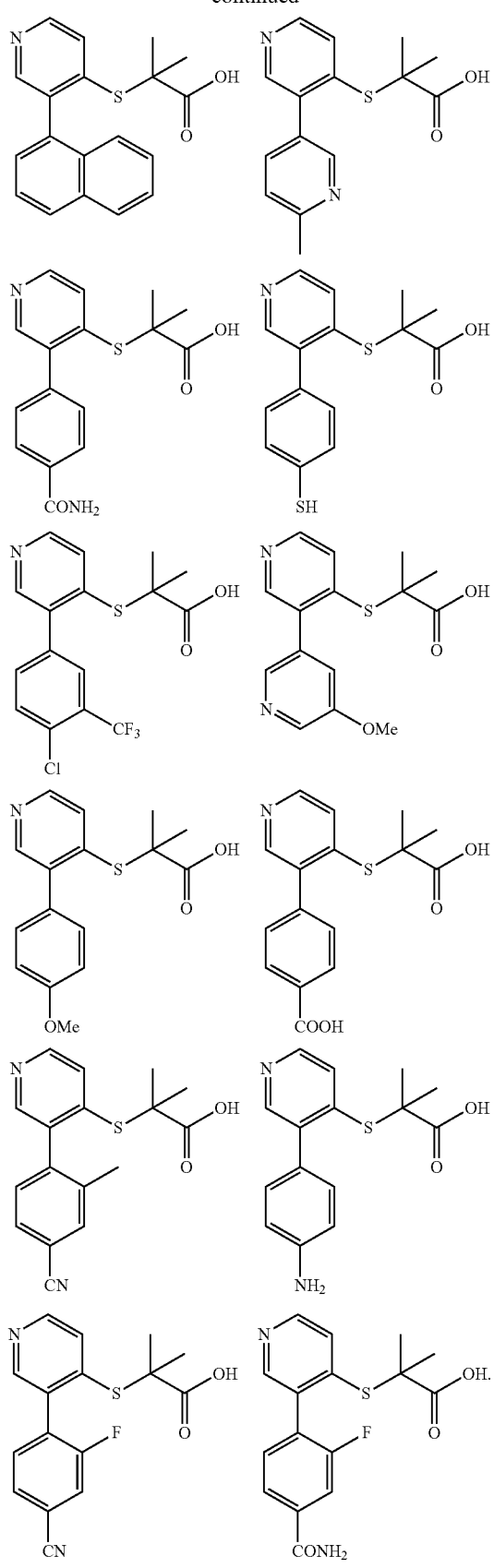

Another embodiment provides a compound of formula (I) having the structure of formula (I-M):

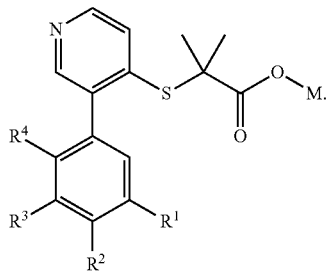

(I-M)

Another embodiment provides a compound of formula (I-M) wherein $R^1$, $R^3$ and $R^4$ are all H.

Another embodiment provides a compound of formula (I) wherein $R^a$ and $R^b$ together with the carbon atom to which they are attached form a 3-, 4-, 5- or 6-membered ring, optionally containing one or two heteroatoms selected from O, N and S.

Another embodiment provides a compound of formula (I) wherein $R^a$ and $R^b$ together with the carbon atom to which they are attached form a 3-, 4-, 5- or 6-membered ring.

Another embodiment provides a compound of formula (I) wherein $R^a$ and $R^b$ together with the carbon atom to which they are attached form a 3-membered ring.

Another embodiment provides a compound of formula (I) wherein M is H.

Another embodiment provides a compound of formula (I) wherein M is $C_1$-$C_3$ alkyl.

Another embodiment provides a compound of formula (I) wherein M is a pharmaceutically acceptable cation.

Another embodiment provides a compound of formula (I) wherein the pharmaceutically acceptable cation is $Na^+$, $Li^+$, $K^+$, $Ca^{2+}$, $Mg^{2+}$, $NH_4^+$, tetramethylammonium, tetraethylammonium, methylamino, dimethylamino, trimethylamino or triethylamino.

Synthetic Procedures

In another aspect, methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. In some embodiments, compounds described herein are synthesized by any suitable method.

In some embodiments, the starting materials used for the synthesis of the compounds as described herein are obtained from commercial sources, such as Aldrich Chemical Co. (Milwaukee, Wis.), Sigma Chemical Co. (St. Louis, Mo.). In some embodiments, the starting materials used for the synthesis of the compounds as described herein are synthesized using techniques and materials described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference for such disclosure). In some embodiments, the following synthetic methods are utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

Examples of Covalent Linkages and Precursors Thereof

| Covalent Linkage | Electrophile | Nucleophile |
| --- | --- | --- |
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Aziridines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Use of Protecting Groups

In some embodiments of the reactions described herein, it is necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and, in some embodiments, are used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments, carboxylic acid and hydroxy reactive moieties are also blocked with hydrolytically removable protective groups such as the benzyl group, while amine groups capable of hydrogen bonding with acids are blocked with base labile groups such as Fmoc. In some embodiments, carboxylic acid reactive moieties are protected by conversion to simple ester compounds as exemplified herein, or they are blocked with oxidatively-removable protective groups such as 2,4-dimethoxybenzyl, while co-existing amino groups are blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd-catalyzed reaction in the presence of acid labile t-butyl carbamate or base-labile acetate amine protecting groups. In some embodiments, the compounds disclosed herein, or intermediate forms thereof, are attached to a resin. As long as the residue is attached to the resin, that functional group is blocked and cannot react. Once released from the resin, the functional group is available to react.

In some embodiments, protecting or blocking groups are selected from:

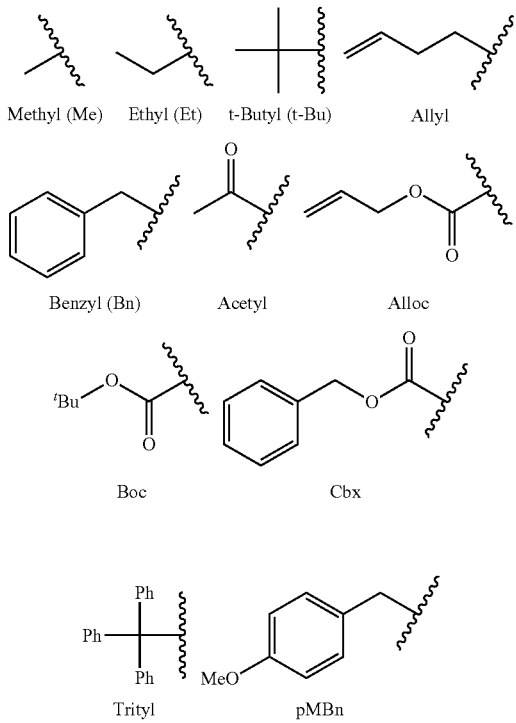

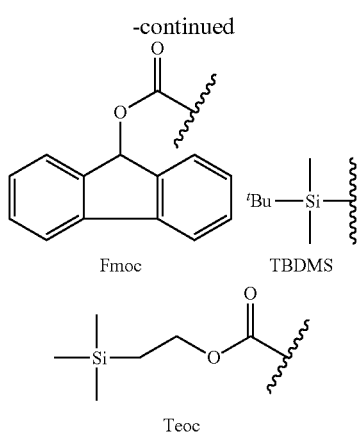

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Preparing Compounds of Formula I

Described herein are processes for the preparation of compounds of formula I. In some embodiments, synthesis of the compounds of the invention are performed following the procedures described below. Generally, the thioacetic acid sidechain is attached through nucleophilic substitution reactions and the biaryl bond is constructed by Pd (0) mediated coupling of a boronic acid to an aryl bromide. The resulting biaryl compound can be processed into the desired compounds of formula (I) via standard techniques. Schemes I-A-a thru Scheme I-H-a illustrate some of the synthetic approaches contemplated but are not to be considered limiting in the scope of synthetic methods useful for the preparation of compounds of formula I.

Scheme I-A-a:

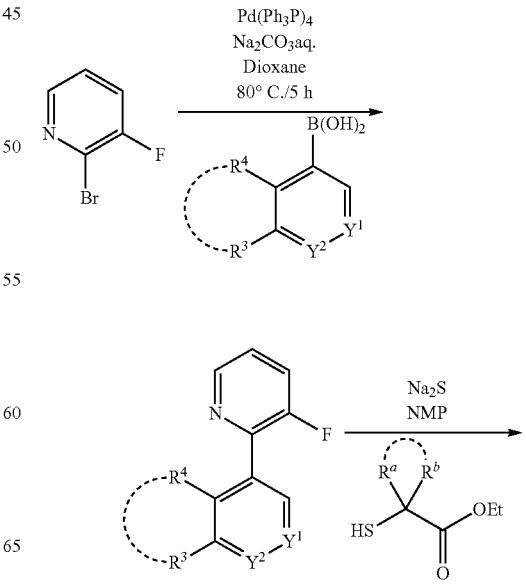

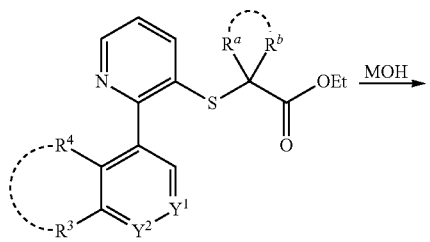
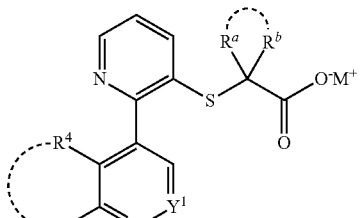
Scheme I-A-b:
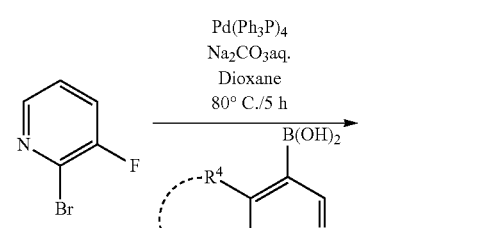
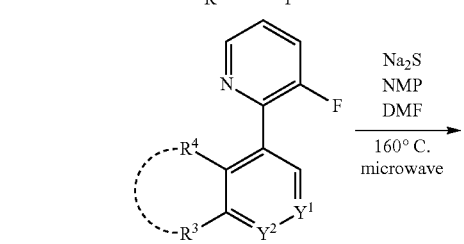
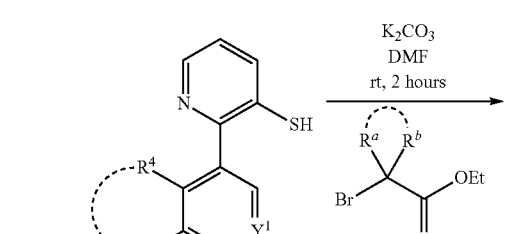
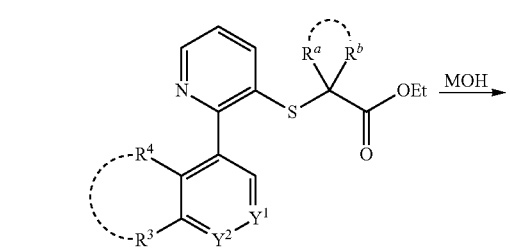
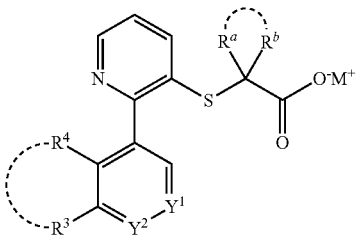
Similar techniques can be employed for the synthesis of the pyridine derivatives shown below.
Scheme I-B-a:

Scheme I-B-b:
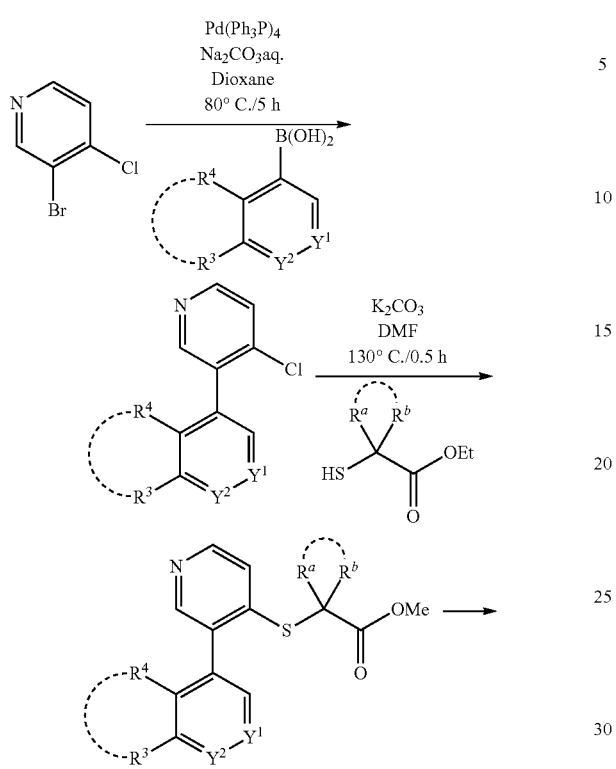
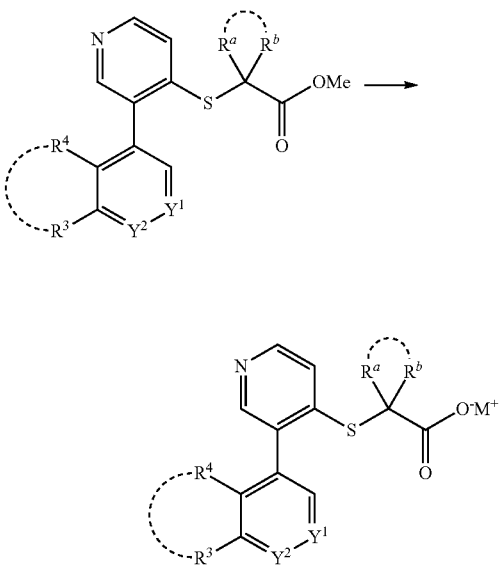
Scheme I-C:
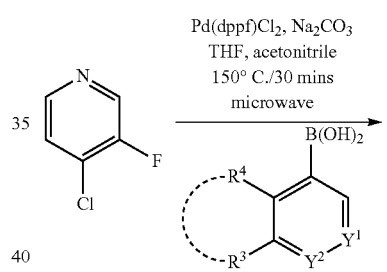
Scheme I-B-c:
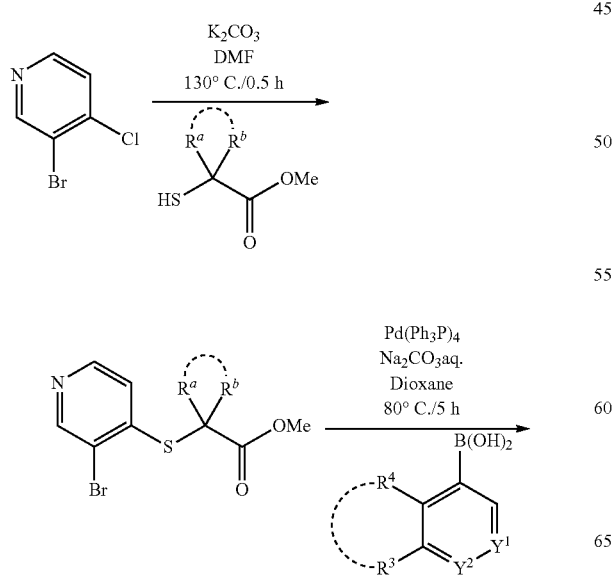
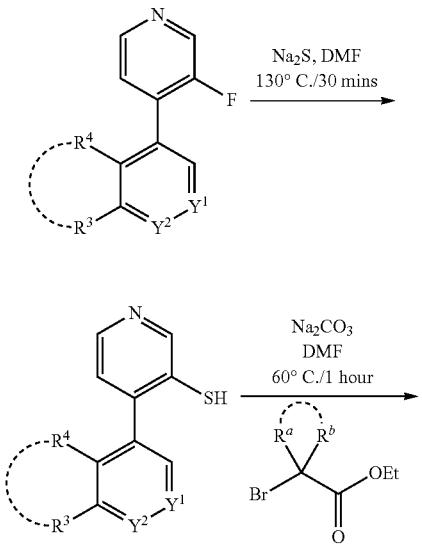

-continued
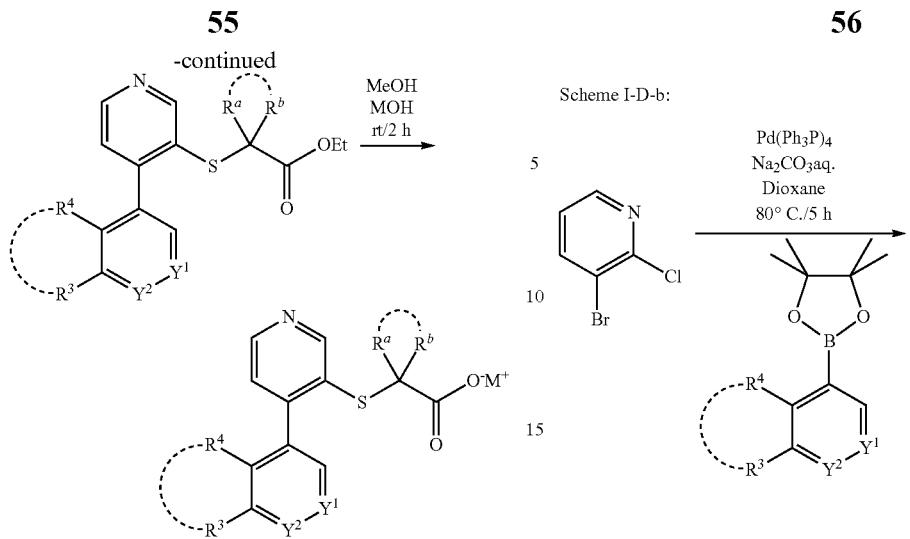
Scheme I-D-b:
Scheme 1-D-a:
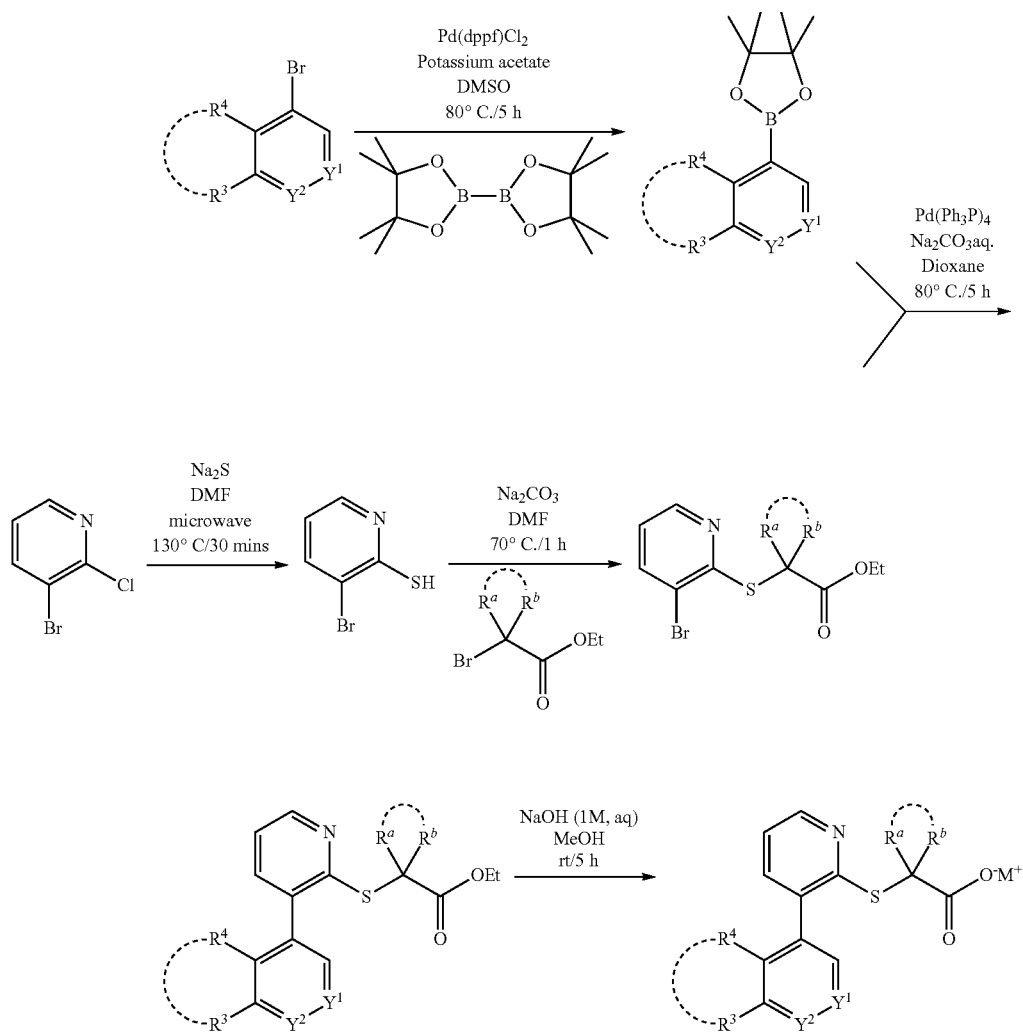

-continued
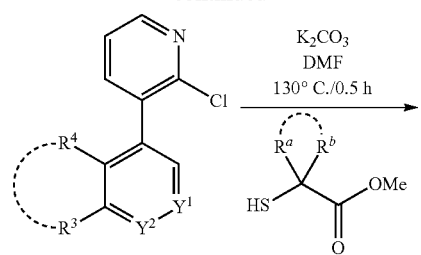
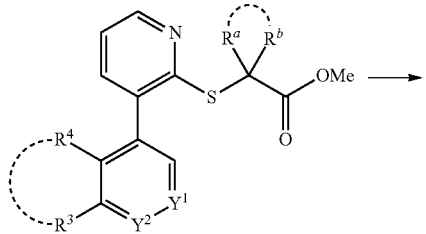
Scheme I-D-c:
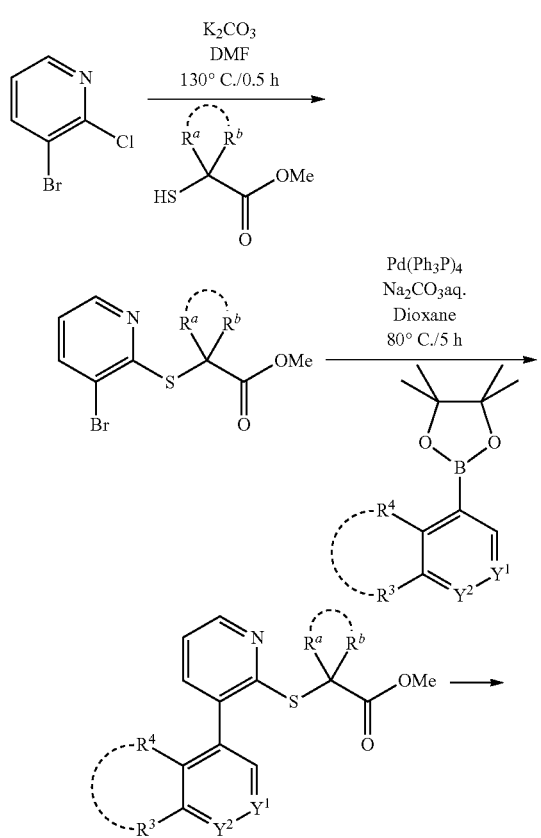
-continued
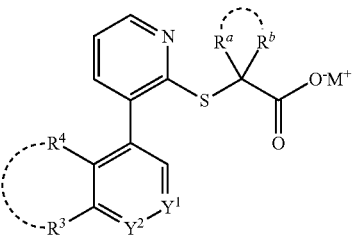
Scheme I-E-a:
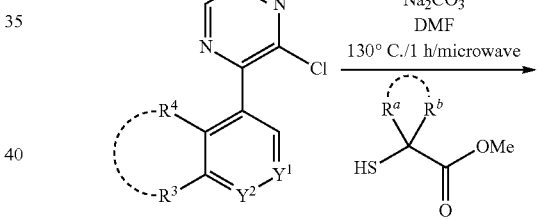
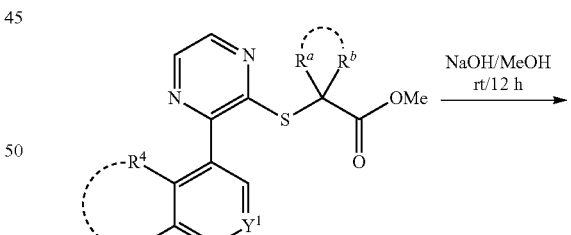
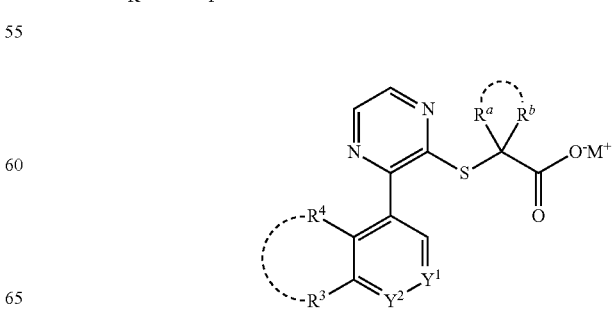

Scheme I-E-b:
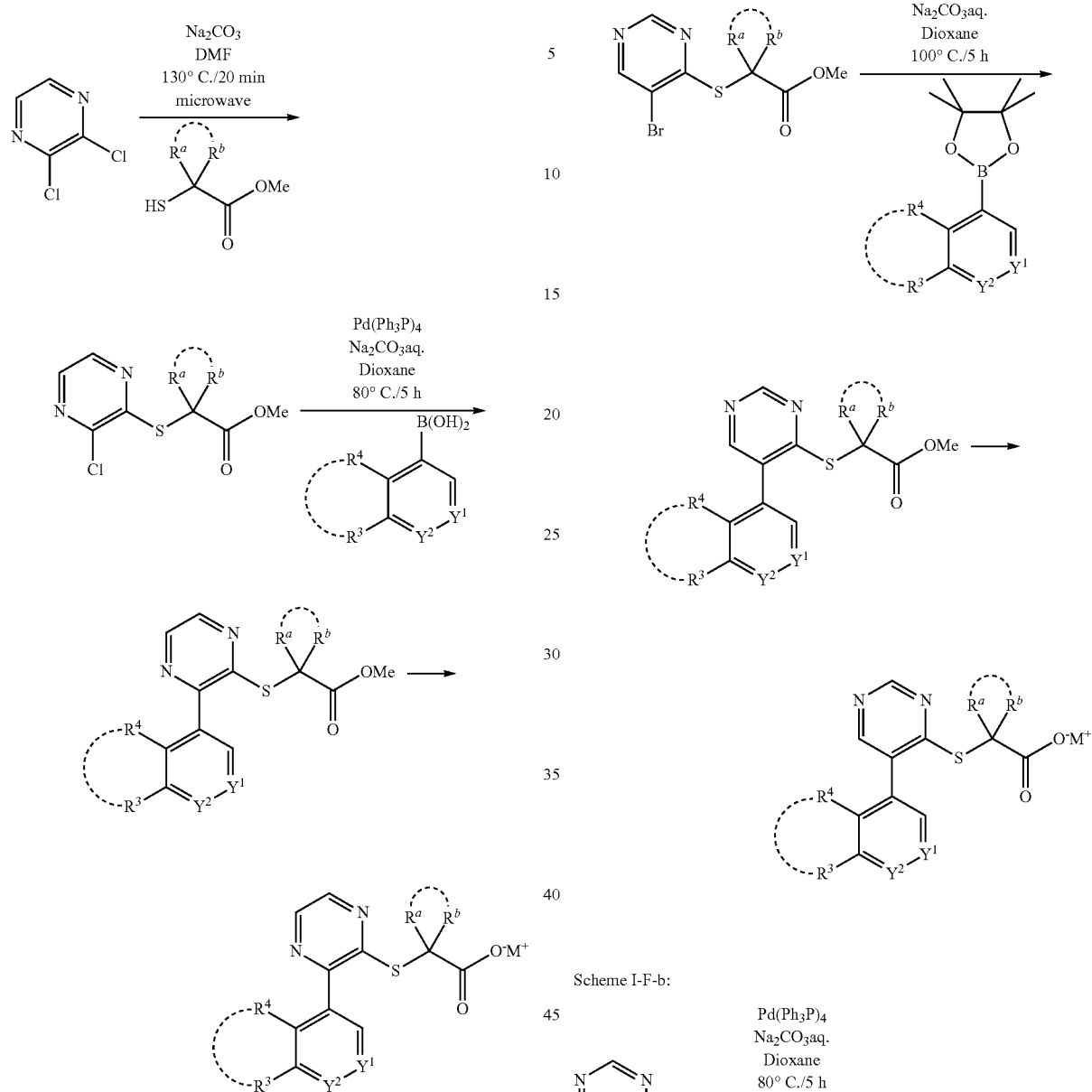
Scheme I-F-a:
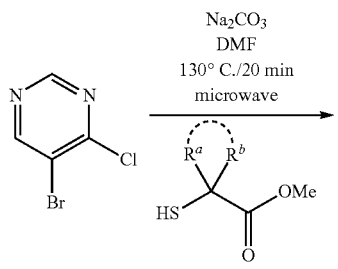
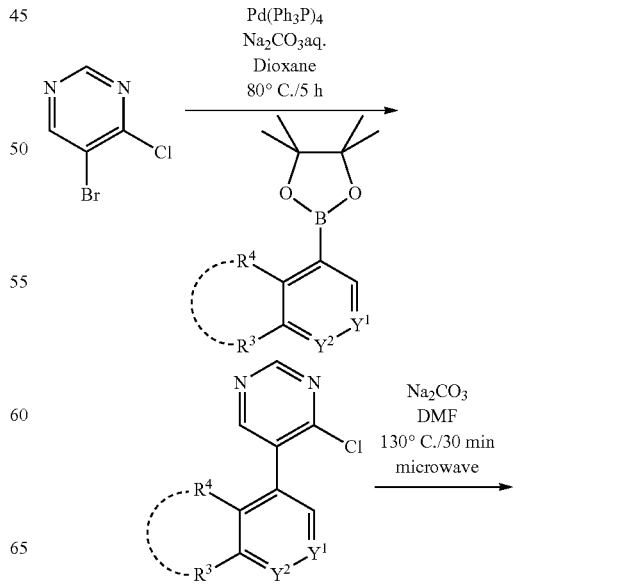
Scheme I-F-b:

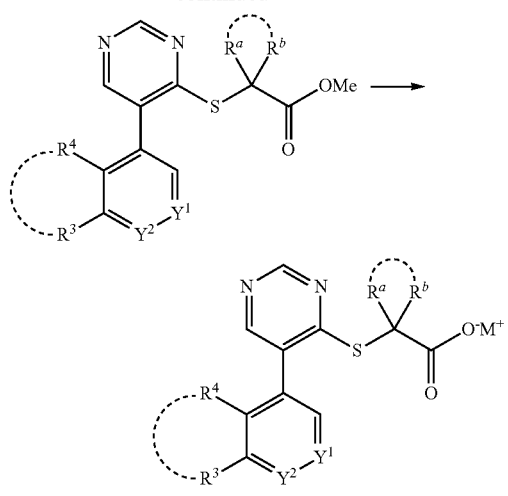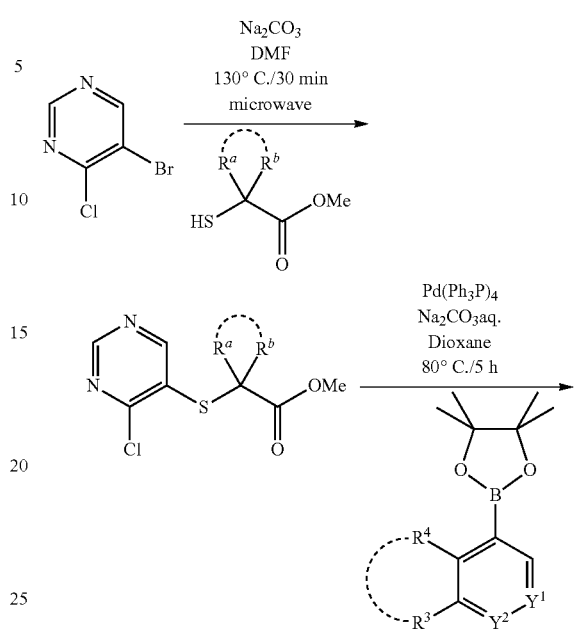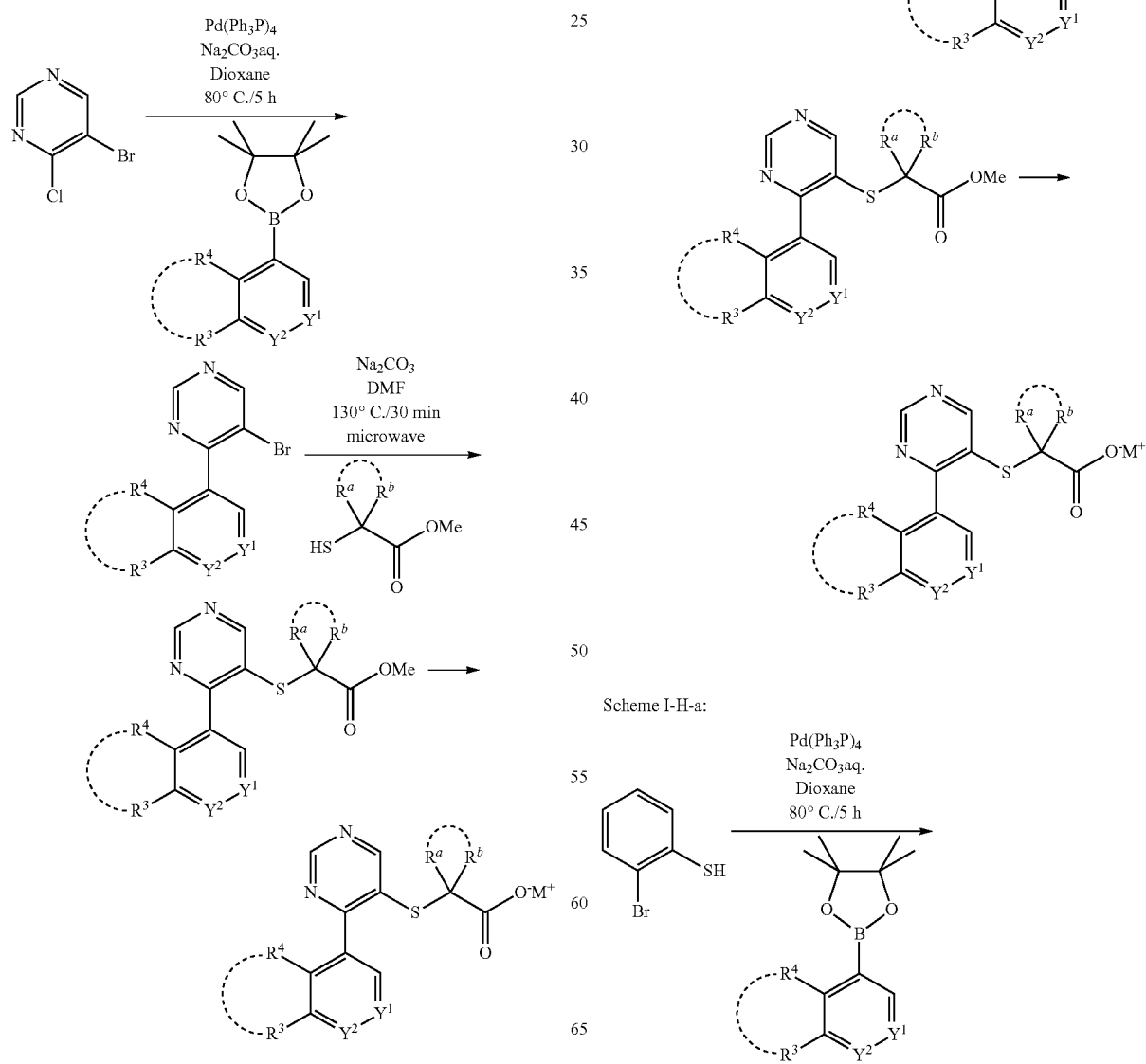

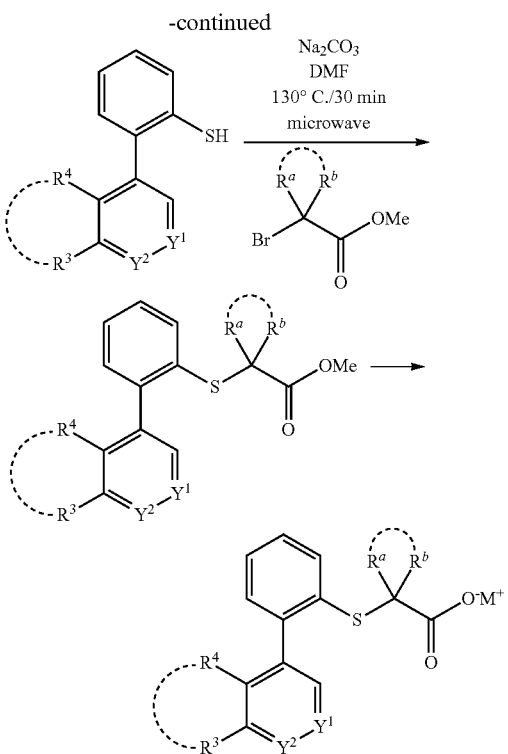

Further Forms of Compounds of the Compounds Disclosed Herein

Isomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization. The compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxy-alkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

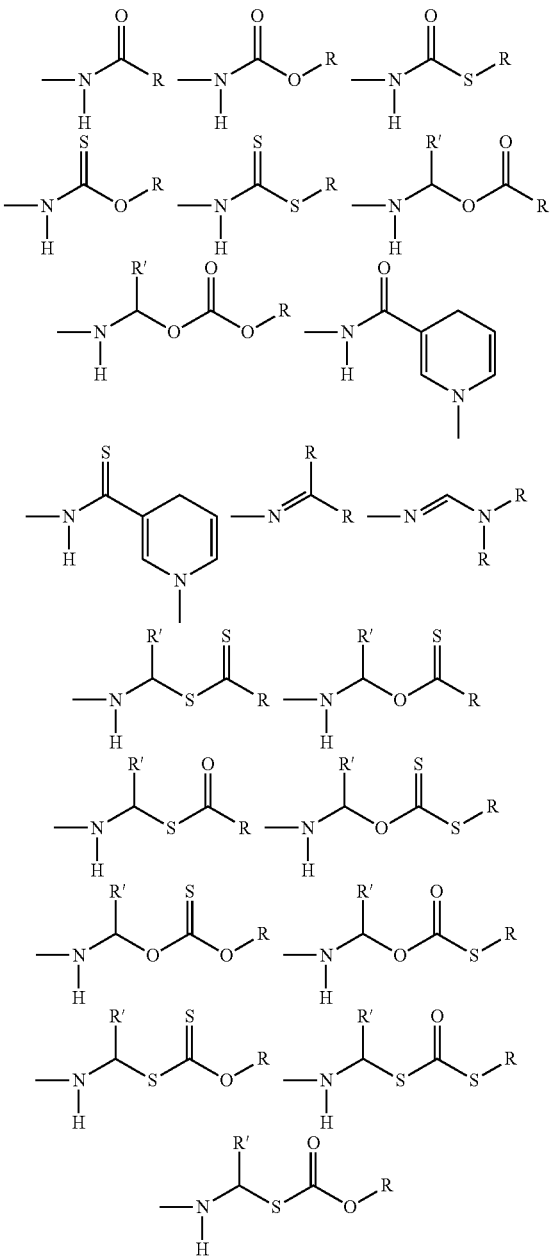

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Pharmaceutical Compositions

Described herein are pharmaceutical compositions. In some embodiments, the pharmaceutical compositions comprise an effective amount of a compound of formula I, or a metabolite, pharmaceutically acceptable salt, ester, prodrug, solvate, hydrate or derivative thereof. In some embodiments, the pharmaceutical compositions comprise an effective amount of a compound formula I, or a metabolite, pharmaceutically acceptable salt, ester, prodrug, solvate, hydrate or derivative thereof and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human.

Modes of Administration

In some embodiments, the compounds and compositions described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. The administration can also be by direct injection at the site of a diseased tissue or organ.

In some embodiments, formulations suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical preparations are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

The compounds or compositions described herein can be delivered in a vesicle, such as a liposome. The compounds and pharmaceutical compositions described herein can also be delivered in a controlled release system, or a controlled release system can be placed in proximity of the therapeutic target. In one embodiment, a pump may be used.

The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use are optionally prepared according to known method, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into an individual's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the active ingredient with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention can be used. As used herein, topical application can include mouth washes and gargles.

Pharmaceutical compositions may be administered in intranasal form via topical use of suitable intranasal vehicles and delivery devices, or via transdermal routes, using transdermal skin patches. To be administered in the form of a transdermal delivery system, the dosage administration will, of course, be continuous rather than intermittent throughout the dosage regimen.

The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition may include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Doses

The amount of pharmaceutical composition administered will firstly be dependent on the mammal being treated. In the instances where pharmaceutical compositions are administered to a human individual, the daily dosage will normally be determined by the prescribing physician with the dosage generally varying according to the age, sex, diet, weight, general health and response of the individual, the severity of the individual's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. The quantity of active compound in a unit dose of preparation may be varied or adjusted from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Combination Therapies

The compounds described herein or a pharmaceutically acceptable salt, solvate, polymorph, ester, tautomer or prodrug thereof may be administered as a sole therapy. The compounds described herein or a pharmaceutically acceptable salt, solvate, polymorph, ester, tautomer or prodrug thereof may also be administered in combination with another therapy or therapies.

For example, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent (which also includes a therapeutic regimen) that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies may include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or therapeutic agents or the individual may experience a synergistic benefit.

In the instances where the compounds described herein are administered in combination with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain good blood levels thereof, while the other therapeutic agent may be administered intravenously. Thus the compounds described herein may be administered concurrently (e.g., simultaneously, essentially simultaneously or within the same treatment protocol), sequentially or dosed separately to other therapeutic agents. The initial administration can be made according to established protocols known in the art, and then, based upon the observed effects, the dosage, modes of administration and times of administration can be modified by the skilled clinician.

The particular choice of compound and other therapeutic agent will depend upon the diagnosis of the attending physicians and their judgment of the condition of the individual and the appropriate treatment protocol. In some embodiments, the additional agent is a URAT 1 inhibitor, a xanthine oxidase inhibitor, a xanthine dehydrogenase, a xanthine oxidoreductase inhibitor, a purine nucleoside phosphorylase (PNP) inhibitor, a uric acid transporter inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In certain instances, URAT 1 is an ion exchanger that mediates urate transportation. In certain instances, URAT I mediates urate transportation in the proximal tubule. In certain instances, URAT I exchanges urate in a proximal tubule for lactate and nicotinate. In certain instances, xanthine oxidase oxidizes hypoxanthine to xanthine, and further to uric acid. In certain instances, xanthine dehydrogenase catalyzes the conversion of xanthine, $NAD^+$, and $H_2O$ into urate, NADH, and $H^+$. In some embodiments, the additional agent is allopurinol, febuxostat (2-(3-cyano-4-isobutoxyphenyl)-4-methyl-1,3-thiazole-5-carboxylic acid), FYX-051 (4-(5-pyridin-4-yl-1H-[1,2,4]triazol-3-yl)pyridine-2-carbonitrile), probenecid, sulfinpyrazone, benzbromarone, acetaminophen, steroids, nonsteroidal anti-inflammatory drugs (NSAIDs), adrenocorticotropic hormone (ACTH), colchicine, a glucorticoid, an adrogen, a cox-2 inhibitor, a PPAR agonist, naproxen, sevelamer, sibutmaine, troglitazone, proglitazone, another uric acid lowering agent, losartan, fibric acid, benziodarone, salisylate, anlodipine, vitamin C, or combinations thereof

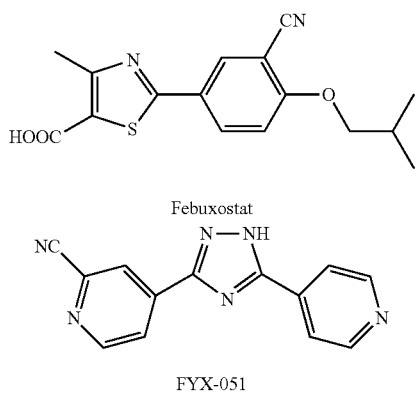

Febuxostat

FYX-051

Diseases

Described herein are methods of treating a disease in an individual suffering from said disease comprising administering to said individual an effective amount of a composition comprising a compound disclosed herein or a pharmaceutically acceptable salt, solvate, polymorph, ester, tautomer or prodrug thereof.

Also described herein are methods of preventing or delaying onset of a disease in an individual at risk for developing said disease comprising administering to said individual an effective amount to prevent or delay onset of said disease, of a composition comprising a compound disclosed herein or a pharmaceutically acceptable salt, solvate, polymorph, ester, tautomer or prodrug thereof.

Further described herein are methods for the prophylaxis or treatment of any disease or disorder in which aberrant levels of uric acid plays a role including, without limitation: hyperuricemia, gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof in a human or other mammal. The methods disclosed herein extend to such a use and to the use of the compounds for the manufacture of a medicament for treating such diseases or disorders. Further, the methods disclosed herein extend to the administration to a human an effective amount of a compound disclosed herein for treating any such disease or disorder.

Individuals that can be treated with the compounds described herein, or a pharmaceutically acceptable salt, ester, prodrug, solvate, hydrate or derivative of said compounds, according to the methods of this invention include, for example, individuals that have been diagnosed as having gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof.

In some embodiments, an individual having an aberrant uric acid level is administered an amount of at least one compound disclosed herein sufficient to modulate the aberrant uric acid level (e.g., to a medically-acceptable level). In some embodiments, an individual treated with the compounds disclosed herein displays aberrant uric acid levels wherein the uric acid levels in blood exceed a medically-accepted range (i.e., hyperuricemia). In some embodiments, an individual treated with the compounds disclosed herein displays aberrant uric acid levels wherein uric acid levels in the blood exceed 360 μmmol/L (6 mg/dL) for a female individual or 400 μmmol/L (6.8 mg/dL) for a male individual. In some embodiments, an individual treated with the compounds disclosed herein displays aberrant uric acid levels wherein uric acid levels in urine exceed a medically-accepted range (i.e., hyperuricosuria). In some embodiments, an individual treated with the compounds disclosed herein displays aberrant uric acid levels wherein uric acid levels in urine exceed 800 mg/day (in a male individual) and greater than 750 mg/day (in a female individual).

In some embodiments, an individual treated with the compounds disclosed herein (1) displays aberrant uric acid levels, and (2) suffers from a cardiovascular disorder. In some embodiments, an individual treated with the compounds disclosed herein (1) displays aberrant uric acid levels, and (2) suffers from an aneurysm; angina; atherosclerosis; a stroke; cerebrovascular disease; congestive heart failure; coronary artery disease; and/or a myocardial infarction. In some embodiments, an individual treated with the compounds disclosed herein (1) displays aberrant uric acid levels, and (2) displays (a) c-reactive protein (CRP) levels above about 3.0 mg/L; (b) homocysteine levels above about 15.9 mmol/L; (c) LDL levels above about 160 mg/dL; (d) HDL levels below about 40 mg/dL; and/or (e) serum creatinine levels above about 1.5 mg/dL.

In some embodiments, an individual treated with the compounds disclosed herein (1) displays aberrant uric acid levels, and (2) suffers from diabetes. In some embodiments, an individual treated with the compounds disclosed herein (1) displays aberrant uric acid levels, and (2) suffers from Type I diabetes. In some embodiments, an individual treated with the compounds disclosed herein (1) displays aberrant uric acid levels, and (2) suffers from Type II diabetes. In some embodiments, an individual treated with the compounds disclosed herein (1) displays aberrant uric acid levels, and (2) suffers from a loss of beta cells of the islets of Langerhans in the pancreas. In some embodiments, an individual treated with the compounds disclosed herein (1) displays aberrant uric acid levels, and (2) suffers from insulin resistance and/or reduced insulin sensitivity. In some embodiments, an individual treated with the compounds disclosed herein (1) displays aberrant uric acid levels, and (2) displays (a) a fasting plasma glucose level $\geqq 126$ mg/dL; (b) a plasma glucose level $\geqq 200$ mg/dL two hours after a glucose tolerance test; and/or (c) symptoms of hyperglycemia and casual plasma glucose levels $\geqq 200$ mg/dL (11.1 mmol/l).

In some embodiments, an individual treated with the compounds disclosed herein (1) displays aberrant uric acid levels, and (2) suffers from metabolic syndrome. In some embodiments, an individual treated with the compounds disclosed herein (1) displays aberrant uric acid levels, and (2) suffers from (a) diabetes mellitus, impaired glucose tolerance, impaired fasting glucose and/or insulin resistance, (b) at least two of (i) blood pressure: $\geqq 140/90$ mmHg; (ii) dyslipidaemia: triglycerides (TG): $\geqq 1.695$ mmol/L and high-density lipoprotein cholesterol (HDL-C) $\leqq 0.9$ mmol/L (male), $\leqq 1.0$ mmol/L (female); (iii) central obesity:waist:hip ratio >0.90 (male); >0.85 (female), and/or body mass index >30 kg/m2; and (iv) microalbuminuria: urinary albumin excretion ratio $\geqq 20$ mg/min or albumin:creatinine ratio $\geqq 30$ mg/g. In some embodiments, an individual treated with the compounds disclosed herein (1) displays aberrant uric acid levels, and (2) suffers from insulin resistance (i.e., the top 25% of the fasting insulin values among non-diabetic individuals) and (b) at least two of (i) central obesity: waist circumference $\geqq 94$ cm (male), $\geqq 80$ cm (female); (ii) dyslipidaemia: TG $\geqq 2.0$ mmol/L and/or HDL-C <1.0 mmol/L or treated for dyslipidaemia; (iii) hypertension: blood pressure $\geqq 140/90$ mmHg or antihypertensive medication; and (iv) fasting plasma glucose $\geqq 6.1$ mmol/L. In some embodiments, an individual treated with the compounds disclosed herein (1) displays aberrant uric acid levels, and (2) displays at least three of (a) elevated waist circumference: Men $\geqq 40$ inches (men) and $\geqq 35$ inches (women); (b) elevated triglycerides: $\geqq 150$ mg/dL; (c) reduced HDL: <40 mg/dL (men) and <50 mg/dL (women); (d) elevated blood pressure: $\geqq 130/85$ mm Hg or use of medication for hypertension; and (e) elevated fasting glucose: $\geqq 100$ mg/dL (5.6 mmol/L) or use of medication for hyperglycemia.

In some embodiments, an individual treated with the compounds disclosed herein (1) displays aberrant uric acid levels, and (2) suffers from kidney disease or kidney failure. In some embodiments, an individual treated with the compounds disclosed herein (1) displays aberrant uric acid levels, and (2) displays oliguria (decreased urine production. In some embodiments, an individual treated with the compounds disclosed herein (1) displays aberrant uric acid levels, and (2) produces less than 400 mL per day of urine (adults), produces less than 0.5 mL/kg/h of urine (children), or produces less than 1 mL/kg/h of urine (infants).

Uric Acid

In certain instances, purines (adenine, guanine), derived from food or tissue turnover (cellular nucleotides undergo continuous turnover), are catabolized in humans to their final oxidation product, uric acid. In certain instances, guanine is oxidized to xanthine, which is turn is further oxidized to uric acid by the action of xanthine oxidase; adenosine is converted to inosine which is further oxidized to hypoxanthine. In certain instances, xanthine oxidase oxidizes hypoxanthine to xanthine, and further to uric acid. In certain instances, as part of the reverse process, the enzyme hypoxanthine-guanine phosphoribosyltransferase (HGPRT) salvages guanine and hypoxanthine.

segment. In certain instances, the bidirectional transport results in drugs that inhibit uric acid transport decreasing, rather than increasing, the excretion of uric acid, compromising their therapeutic usefulness. In certain instances, normal uric acid levels in human adults (5.1+/−0.93 mg/dL) are close to the limits of urate solubility (~7 mg/dL at 37° C.), which creates a delicate physiologic urate balance. In certain

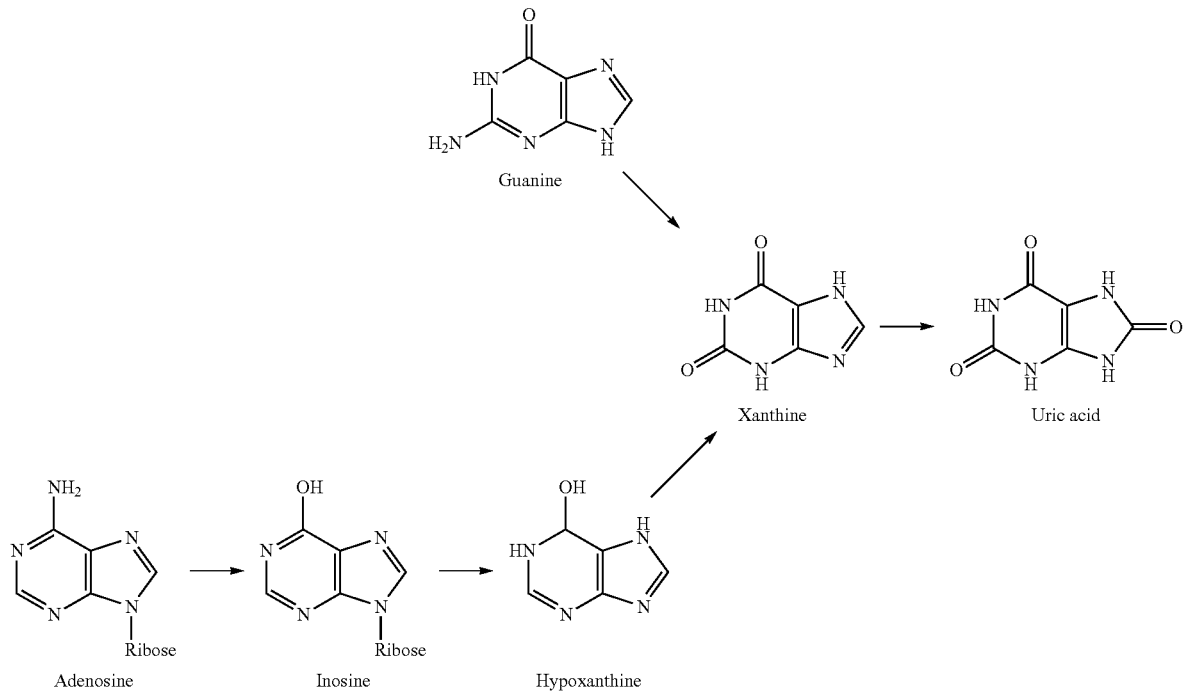

In certain instances, the keto form of uric acid is in equilibrium with the enol form which loses a proton at physiological pH to form urate. In certain instances, (e.g., under serum conditions (pH 7.40, 37° C.)), about 98% of uric acid is ionized as the monosodium urate salt. In certain instances, urate is a strong reducing agent and potent antioxidant. In humans, about half the antioxidant capacity of plasma comes from uric acid.

instances, the normal uric acid range for females is approximately 1 mg/dL below the male range.

Hyperuricemia

In certain instances, hyperuricemia is characterized by higher than normal blood levels of uric acid, sustained over long periods of time. In certain instances, increased blood urate levels may be due to enhanced uric acid production

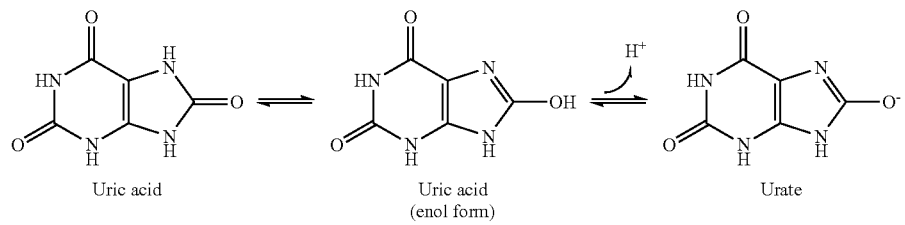

In certain instances, most uric acid dissolves in blood and passes to the kidneys, where it is excreted by glomerular filtration and tubular secretion. In certain instances, a substantial fraction of uric acid is reabsorbed by the renal tubules. One of the peculiar characteristics of the uric acid transport system is that, although the net activity of tubular function is reabsorption of uric acid, the molecule is both secreted and reabsorbed during its passage through the nephron. In certain instances, reabsorption dominates in the S1 and S3 segments of the proximal tubule and secretion dominates in the S2

(~10-20%) and/or reduced renal excretion (~80-90%) of uric acid. In certain instances, causes of hyperuricemia may include:
Obesity/weight gain
Excessive alcohol use
Excessive dietary purine intake (foods such as shellfish, fish roe, scallops, peas lentils, beans and red meat, particularly offal—brains, kidneys, tripe, liver)
Certain medications, including low-dose aspirin, diuretics, niacin, cyclosporine, pyrazinamide, ethambutol, some high blood pressure drugs and some cancer chemotherapeutics, immunosuppressive and cytotoxic agents Specific disease states, particularly those associated with a high cell turnover rate (such as malignancy, leukemia, lymphoma or psoriasis), and also including high blood pressure, hemoglobin disorders, hemolytic anemia, sickle cell anemia, various nephropathies, myeloproliferative and lymphoproliferative disorders, hyperparathyroidism, renal disease, conditions associated with insulin resistance and diabetes mellitus, and in transplant recipients, and possibly heart disease Inherited enzyme defects Abnormal kidney function (e.g. increased ATP turn over, reduced glomerular urate filtration)

Exposure to lead (plumbism or "saturnine gout")

In certain instances, hyperuricemia may be asymptomatic, though is associated with the following conditions:

Gout

Gouty arthritis

Uric acid stones in the urinary tract (urolithiasis)

Deposits of uric acid in the soft tissue (tophi)

Deposits of uric acid in the kidneys (uric acid nephropathy)

Impaired kidney function, possibly leading to chronic and acute renal failure

Gout

Prevalence

The incidence of gout has increased over the past two decades and, in the United States, affects as much as 2.7% of the population aged 20 years and older, totaling over 5.1 million American adults. Gout is more common in men than women, (3.8% or 3.4 million men vs. 1.6% or 1.7 million women), typically affecting men in their 40's and 50's (although gout attacks can occur after puberty which sees an increase in uric acid levels). An increase in prevalence of gout from 2.9 to 5.2 per 1000 in the time period 1990 to 1999 was observed, with most of the increase occurring in those over the age of 65. Gout attacks are more common in women after menopause. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Leading Causes

In most cases, gout is associated with hyperuricemia. In certain instances, individuals suffering from gout excrete approximately 40% less uric acid than nongouty individuals for any given plasma urate concentrations. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood disorders (e.g. polycythemia, myeloid metaplasia, etc).

Symptoms

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and may last longer, especially if the disorder is not controlled. In certain instances, episodes damage the affected joint(s) resulting in stiffness, swelling, limited motion and/or persistent mild to moderate pain.

Treatment

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the Gout Attack.

In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, icepacks, elevation and/or protection of the affected area/s. In certain instances, the aforementioned treatments do not prevent recurrent attacks and they do not affect the underlying disorders of abnormal uric acid metabolism.

ii) Preventing Future Attacks.

In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

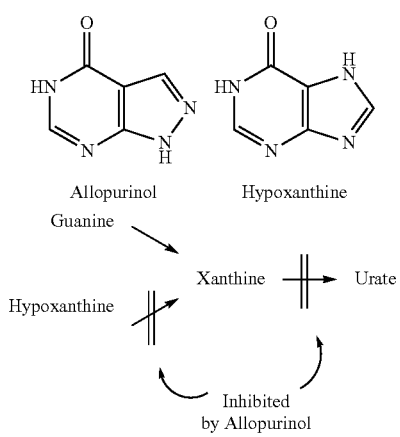

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for disorders of uric acid metabolism has not evolved significantly in the following two decades since the introduction of allopurinol.

In certain instances, Uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Plumbism or "Saturnine Gout"

In certain instances, excessive exposure to lead (lead poisoning or plumbism) results in "saturnine gout," a lead-induced hyperuricemia due to lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

Lesch-Nyhan Syndrome

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disorder leads to severe gout, poor muscle control, and moderate mental retardation, which appear in the first year of life. In certain instances, the disorder also results in self-mutilating behaviors (e.g., lip and finger biting, head banging) beginning in the second year of life. In certain instances, the disorder also results in gout-like swelling in the joints and severe kidney problems. In certain instances, the disorder leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

Hyperuricemia and Other Diseases

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congenative heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of the compounds described herein to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congenative heart failure, stroke, tumor lysis syndrome, endothelial dysfunction, oxidative stress, elevated renin levels, elevated endothelin levels, and/or elevated C-reactive protein levels.

One embodiment provides a method of treating or preventing a condition characterized by abnormal tissue or organ levels of uric acid in an individual comprising administering to the individual an effective amount of a compound of formula (I). Another embodiment provides the method wherein the condition is gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof. Another embodiment provides the method wherein the condition is gout.

Another embodiment provides the method further comprising administering a second agent effective for the treatment of the gout. Another embodiment provides the method wherein the second agent is a URAT 1 inhibitor, a xanthine oxidase inhibitor, a xanthine dehydrogenase, a xanthine oxidoreductase inhibitor, or combinations thereof. Another embodiment provides the method wherein the second agent is allopurinol, febuxostat, FYX-051, or combinations thereof.

In some embodiments, the compounds described herein are administered to an individual suffering from a disease or condition requiring treatment with a compound that is a diuretic. In some embodiments, the compounds described herein are administered to an individual suffering from a disease or condition requiring treatment with a compound that is a diuretic, wherein the diuretic causes renal retention of urate. In some embodiments, the disease or condition is congestive heart failure or essential hypertension.

In some embodiments, administration of the compounds described herein to an individual are useful for improving motility or improving quality of life.

In some embodiments, administration of the compounds described herein to an individual is useful for treating or decreasing the side effects of cancer treatment.

In some embodiments, administration of the compounds described herein to an individual is useful for decreasing kidney toxicity of cis-platin.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals, exotic animals and farm animals, including mammals, rodents, and the like. More preferred animals include horses, dogs, and cats.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

I. Chemical Syntheses

Example 1

Preparation of Compounds of Formula (I-A)

Compounds of formula (I-A) may be prepared according to the general schemes shown below:

Scheme I-A-a:

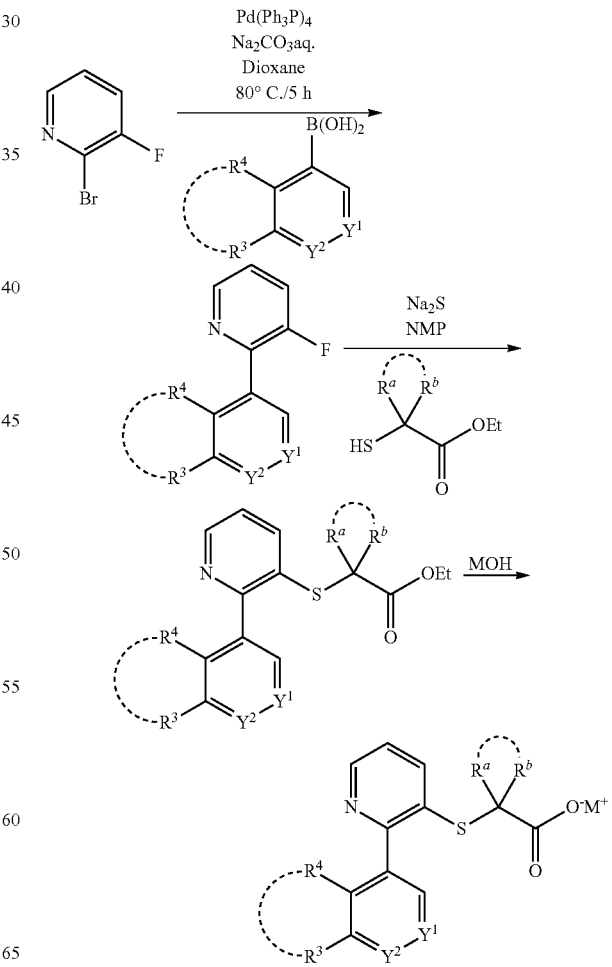

87
Scheme I-A-b:
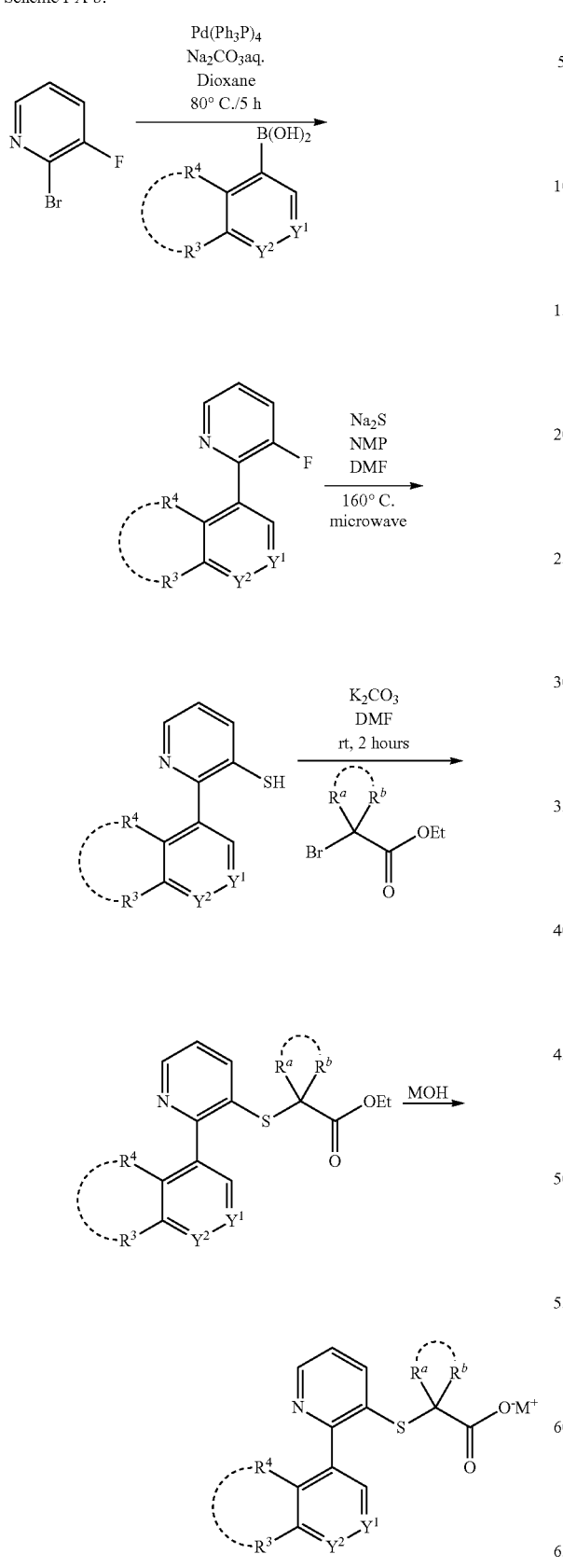
88
Example 1A
2-(3-(4-Cyanophenyl)pyridin-3-ylthio)-2-methylpropanoic acid
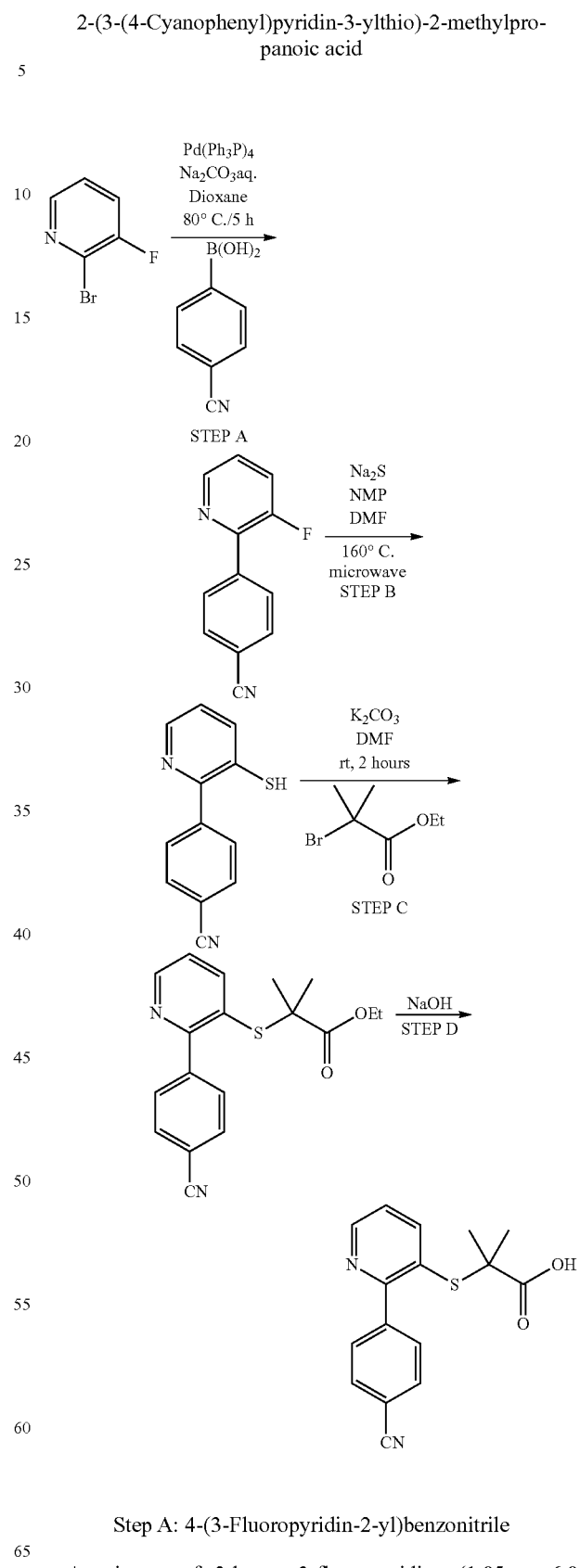
Step A: 4-(3-Fluoropyridin-2-yl)benzonitrile
A mixture of 2-bromo-3-fluoropyridine (1.05 g, 6.0 mmol), 4-cyanophenylboronic acid (0.882 g, 6.0

Pd(PPh$_3$)$_4$ (0.138 g, 0.12 mmol), and aqueous sodium carbonate solution (2M, 6 mL), in dioxane (6 mL) was degassed for 15 minutes. The mixture was sealed, heated to 80° C. for 12 hours, washed with water and extracted with ethyl acetate. The organic layer was dried over magnesium sulfate, concentrated and purified by chromatography to yield 4-(3-fluoropyridin-2-yl)benzonitrile (1.16 g, 89%).

Step B: 4-(3-Mercaptopyridin-2-yl)benzonitrile

A mixture of 4-(3-fluoropyridin-2-yl)benzonitrile (0.198 g, 1.0 mmol), Na$_2$S (0.39 g, 5 mmol), N-methylmorpholine (0.5 mL) and DMF (2 mL) was heated to 160° C. under microwave irradiation for 30 minutes. After the reaction was completed, the mixture was washed with water and extracted with ethyl acetate. The organic layer was dried over MgSO$_4$, concentrated and purified by chromatography to yield 4-(3-mercaptopyridin-2-yl)benzonitrile (0.18 g, 85%).

Step C: Ethyl 2-(2-(4-cyanophenyl)pyridin-3-ylthio)-2-methylpropanoate

A mixture of 4-(3-mercaptopyridin-2-yl)benzonitrile (0.18 g, 0.85 mmol), ethyl 2-bromo-2-methylpropanoate (0.195 g, 1 mmol), and K$_2$CO$_3$ (0.138 g, 1.0 mmol) in DMF (2 mL) was stirred at room temperature for 2 hours. After the reaction was completed, the reaction mixture was washed with water and extracted with ethyl acetate. The organic layer was dried over MgSO$_4$, concentrated and purified by chromatography to yield ethyl 2-(2-(4-cyanophenyl)pyridin-3-ylthio)-2-methylpropanoate (0.137 g, 49%).

Step D: 2-(2-(4-Cyanophenyl)pyridin-3-ylthio)-2-methylpropanoic acid

A mixture of ethyl 2-(2-(4-cyanophenyl)pyridin-3-ylthio)-2-methylpropanoate (0.137 g, 0.42 mmol), aqueous sodium hydroxide solution (1M, 1 mL) and methanol (2 mL) was stirred at 60° C. for 12 hours. The reaction mixture was concentrated to remove methanol, acidified and filtered to obtain 2-(2-(4-cyanophenyl)pyridin-3-ylthio)-2-methylpropanoic acid as a white powder (0.121 g, 96%).

$^1$H NMR (400 MHz, DMSO-d$_6$, 25° C.) 12.72 (bs, COOH), 8.71 ((d, J=3.2 Hz, 1H), 8.04 (d, J=6.4 Hz, 1H), 7.93 (d, J=8.4 Hz, 2H), 7.77 (d, J=8.4 Hz, 2H), 8.04 (dd, J=6.4, 3.2 Hz, 1H), 1.22 (s, 6H).

m/z (M+1) 298.99

Examples 1B-1V

The compounds in the table below are prepared according to the procedures described in example 1A.

| Example | Structure |
|---|---|
| 1B | (2-phenylpyridin-3-ylthio)-2-methylpropanoic acid |
| 1C | (2-(3,4-dichlorophenyl)pyridin-3-ylthio)-2-methylpropanoic acid |
| 1D | (2-(4-ethylphenyl)pyridin-3-ylthio)-2-methylpropanoic acid |
| 1E | (2-(naphthalen-1-yl)pyridin-3-ylthio)-2-methylpropanoic acid |
| 1F | (2-(naphthalen-2-yl)pyridin-3-ylthio)-2-methylpropanoic acid |
| 1G | (2-(4-methylnaphthalen-1-yl)pyridin-3-ylthio)-2-methylpropanoic acid |
| 1H | (2-(pyridin-2-yl)pyridin-3-ylthio)-2-methylpropanoic acid |

| Example | Structure |
|---|---|
| 1I | 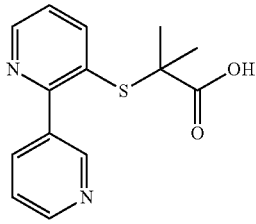 [SMILES: CC(C)(Sc1cccnc1-c1cccnc1)C(=O)O] |
| 1J | 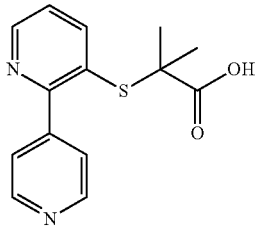 |
| 1K | 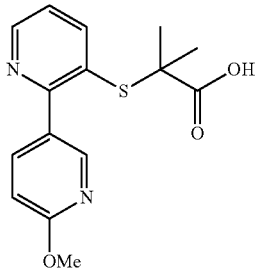 [SMILES: COc1ccc(-c2ncccc2SC(C)(C)C(=O)O)cn1] |
| 1L | 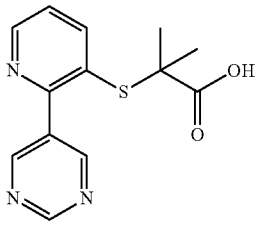 |
| 1M | 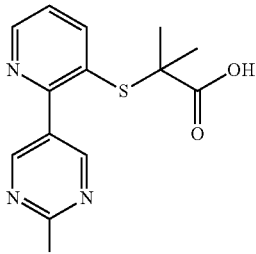 |
| 1N | 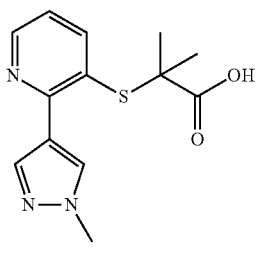 [SMILES: Cn1cc(-c2ncccc2SC(C)(C)C(=O)O)cn1] |
| Example | Structure |
|---|---|
| 1O | 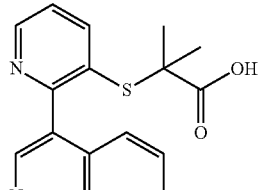 |
| 1P | 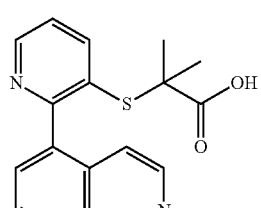 |
| 1Q | 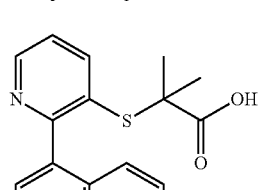 |
| 1R | 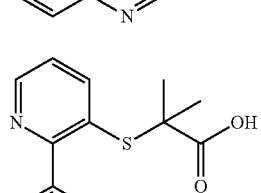 |
| 1S | 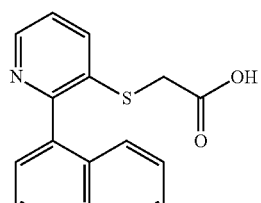 |
| 1T | 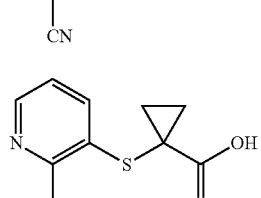 |

93
-continued
| Example | Structure |
|---------|-----------|
| 1U | 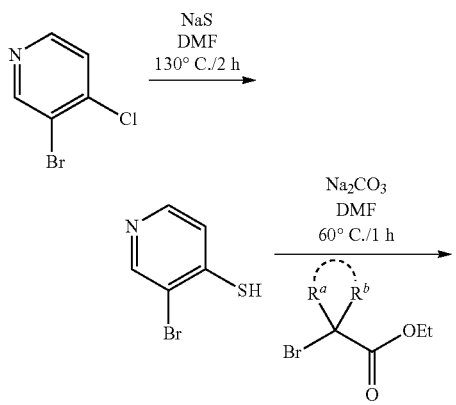 |
| 1V | 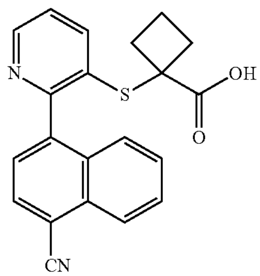 [SMILES: N#Cc1ccc(-c2ncccc2SC2(C(=O)O)CCC2)c2ccccc12] |
| 1W | 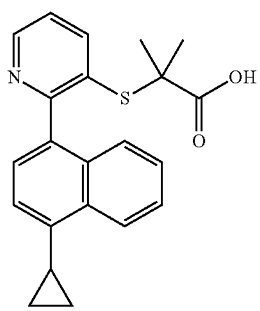 [SMILES: CC(C)(Sc1cccnc1-c1ccc(C2CC2)c2ccccc12)C(=O)O] |
Example 2
Preparation of Compounds of Formula (I-B)
Compounds of formula (I-B) may be prepared according to the general schemes shown below:
Scheme I-B-a:
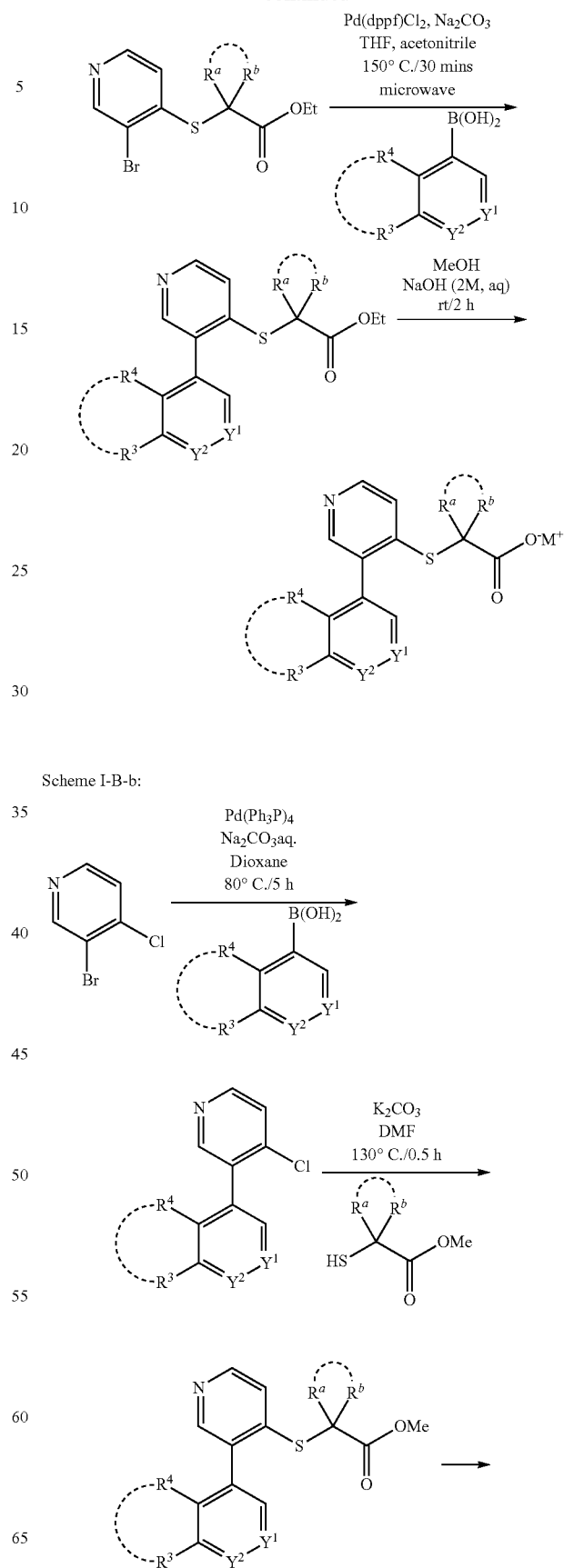
Scheme I-B-b:

-continued

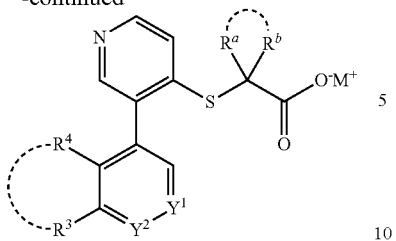

Scheme I-B-c:

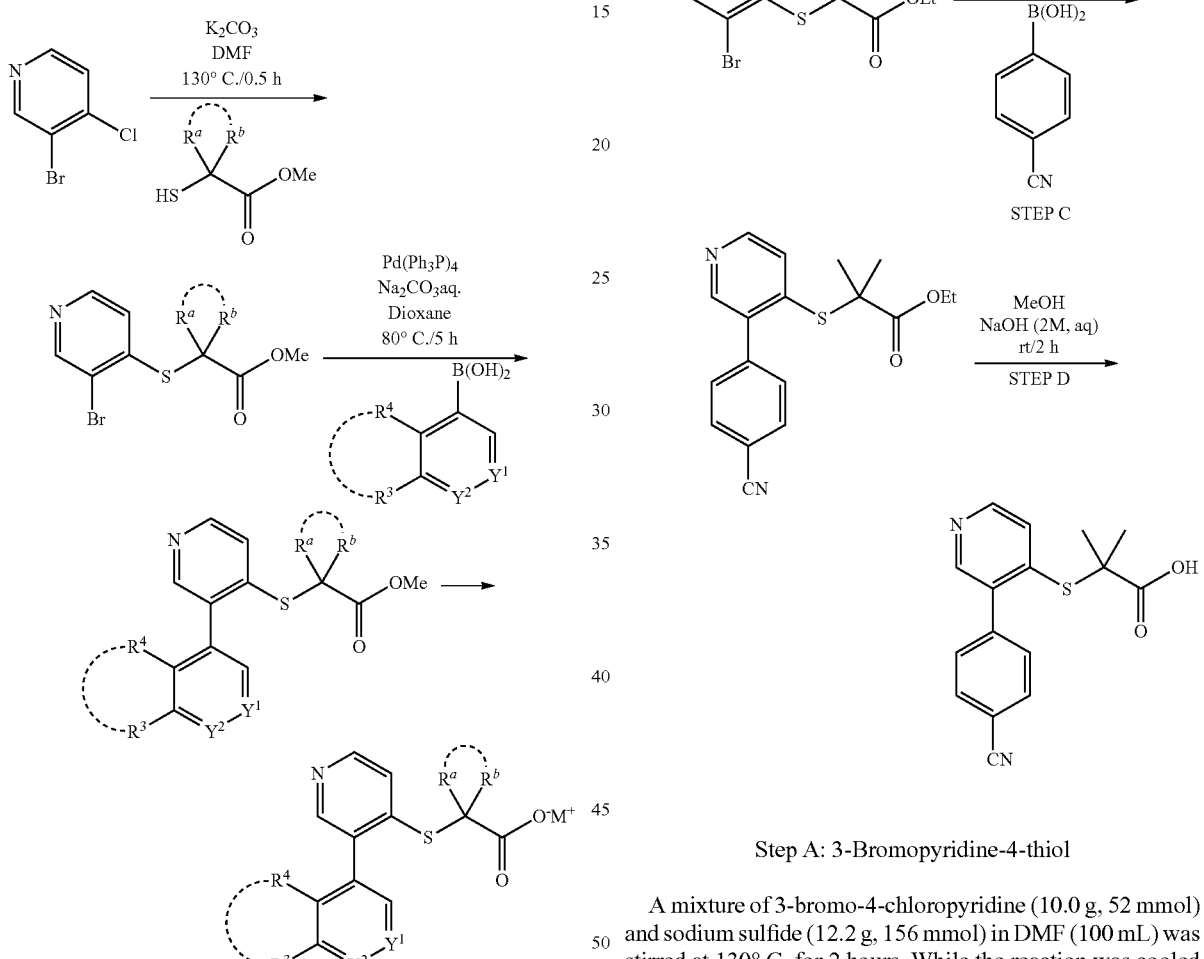

Example 2A 2-(3-(4-Cyanophenyl)pyridin-4-ylthio)-2-methylpropanoic acid

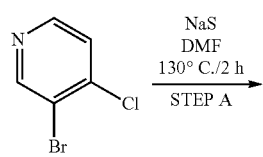

-continued

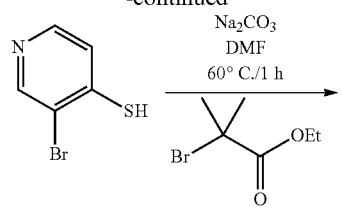

Step A: 3-Bromopyridine-4-thiol

A mixture of 3-bromo-4-chloropyridine (10.0 g, 52 mmol) and sodium sulfide (12.2 g, 156 mmol) in DMF (100 mL) was stirred at 130° C. for 2 hours. While the reaction was cooled in an ice water bath, aqueous HCl (6N, 45 mL) was added drop wise with rigorous stirring. The resulting yellow paste was concentrated using rotary evaporation on a water bath (80° C.) to dryness. The resulting yellow solid was extracted with methanol (4×50 mL), and the combined extracts concentrated to give a yellow solid (9.5 g, 96%).

Step B: Ethyl 2-(3-bromopyridin-4-ylthio)-2-methylpropanoate

A mixture of 3-bromopyridine-4-thiol (step A, 4.75 g, 25 mmol), ethyl 2-bromoisobutyrate (9.75 g, 50 mmol), and sodium carbonate (7.95 g, 75 mmol) in DMF (50 mL) was stirred at 60° C. for 1 hour. The reaction mixture was partitioned between water (100 mL) and ethyl acetate (100 mL). The organic layer was washed with water (2×100 mL) and saturated sodium chloride (100 mL). The aqueous washes were back extracted with ethyl acetate (2×100 mL). The combined organic layers were dried over sodium sulfate, concentrated, and purified by normal phase chromatography (a gradient of 0-25% ethyl acetate in hexane) to yield ethyl 2-(3-bromopyridin-4-ylthio)-2-methylpropanoate as a pale yellow oil (6.6 g, 88%).

Step C: Ethyl 2-(3-(4-cyanophenyl)pyridin-4-ylthio)-2-methylpropanoate

To a mixture of 4-cyanophenylboronic acid (49 mg, 0.33 mmol) and Pd(dppf)Cl$_2$ (9 mg, 5% mole) were added a solution of freshly purified ethyl 2-(3-bromopyridin-4-ylthio)-2-methylpropanoate from (step B, 67 mg, 0.22 mmol) in THF (1 mL), acetonitrile (0.5 mL), and sodium carbonate (1M aqueous, 0.5 mL). The resulting mixture was degassed by nitrogen bubbling for 1 minute, and then heated to 150° C. for 30 minutes under microwave irradiation. The mixture was loaded on to a 5 g ISCO loading cartridge and eluded with a gradient of 0-100% ethyl acetate in hexane on a 12 g ISCO column to yield ethyl 2-(3-(4-cyanophenyl)pyridin-4-ylthio)-2-methylpropanoate (0.049 g, 70%).

Step D: 2-(3-(4-cyanophenyl)pyridin-4-ylthio)-2-methylpropanoic acid

To ethyl 2-(3-(4-cyanophenyl)pyridin-4-ylthio)-2-methylpropanoate (step C, 49 mg, 0.15 mmol) was added methanol (0.8 mL), and sodium hydroxide (2 M aqueous, 0.8 mL). The resulting mixture was stirred at ambient temperature for 2 hours. The volume was reduced (~0.8 mL) by rotary evaporation. To the residue was added HCl (6 N aqueous) with stirring until pH reached 6, resulting in the formation of a white precipitate, which was isolated by filtration. The solid was washed with water (6×1 mL), air dried for 1 hour and dried under vacuum (P$_2$O$_5$) overnight to yield a white powder (28 mg, 64%).

$^1$H NMR (400 MHz, DMSO-d$_6$) δ ppm 1.46 (s, 6H) 7.44 (d, J=5.39 Hz, 1H) 7.60-7.70 (m, 2H) 7.98 (d, J=8.29 Hz, 2H) 8.44 (s, 1H) 8.56 (d, J=5.18 Hz, 1H) 13.14 (br. s., 1H).

MS (m/z), M+1, 299.

Examples 2B-2JJJ

The compounds in the table below were prepared according to the procedure described in example 2A.

| Example | Structure | $^1$H NMR δ ppm (400 MHz, DMSO-d$_6$) | MS (m/z) M + 1 |
|---|---|---|---|
| 2B | 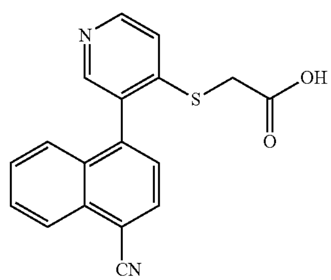 [SMILES: N#Cc1ccc(-c2cnccc2SCC(=O)O)c2ccccc12] | $^1$H NMR (400 MHz, DMSO-d$_6$, 25° C.) 8.77 (d, J = 3.6 Hz, 1H), 8.61 (s, 1H), 8.37 (d, J = 7.2 Hz, 1H), 8.27 (d, J = 7.2 Hz, 1H), 7.91 (dd, J = 7.2, 7.2 Hz, 1H), 7.68-7.80 (m, 3H), 7.61 (d, J = 7.2 Hz, 1H), 4.10 (s, 2H). | 321.07 |
| 2C | 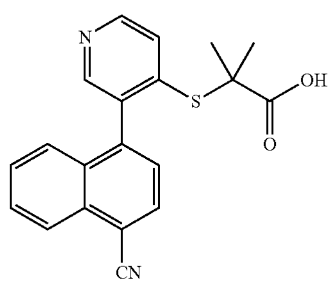 | $^1$H NMR (400 MHz, DMSO-d$_6$, 25° C.) 13.22 (bs, 1H), 8.61 (s, 1H), 8.34-8.39 (m, 2H), 8.02 (dd, J = 7.2, 7.2 Hz, 1H), 7.74-7.79 (m, 2H), 7.60 (dd, J = 7.6, 7.6 Hz, 1H), 7.44-7.53 (m, 2H), 1.61 (s, 3H), 1.54 (s, 3H). | 349.14 |
| 2D | 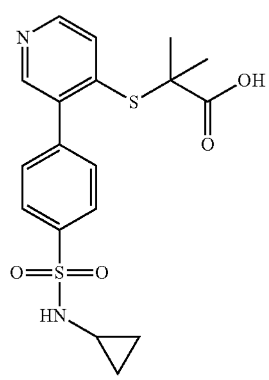 [SMILES: CC(C)(Sc1ccncc1-c1ccc(S(=O)(=O)NC2CC2)cc1)C(=O)O] | 0.37-0.49 (m, 2 H) 0.49-0.60 (m, 2 H) 1.50 (s, 6 H) 2.12-2.27 (m, 1 H) 7.50 (d, J = 5.39 Hz, 1 H) 7.68 (d, J = 8.09 Hz, 2 H) 7.93 (d, J = 8.29 Hz, 2 H) 8.08 (br. s., 1 H) 8.51 (s, 1 H) 8.60 (d, J = 5.39 Hz, 1 H) | 393 |

-continued

| Example | Structure | ¹H NMR δ ppm (400 MHz, DMSO-d₆) | MS (m/z) M + 1 |
|---|---|---|---|
| 2E | 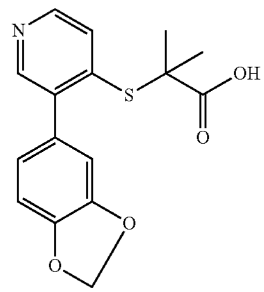 [SMILES: CC(C)(Sc1ccncc1-c1ccc2c(c1)OCO2)C(=O)O] | 1.58 (s, 6 H) 4.32 (s, 3 H) 6.82-6.87 (m, 1 H) 6.89 (d, J = 2.07 Hz, 1 H) 6.91-6.96 (m, 1 H) 7.38-7.41 (m, 1 H) 7.41-7.42 (m, 1 H) 7.54 (d, J = 5.39 Hz, 1 H) 8.22 (s, 1 H) 8.31 (d, J = 5.39 Hz, 1 H) | 318 |
| 2F | 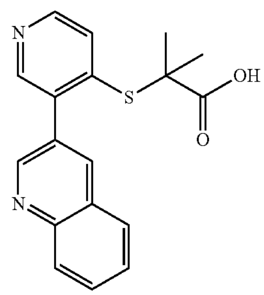 [SMILES: CC(C)(Sc1ccncc1-c1cnc2ccccc2c1)C(=O)O] | 1.46 (s, 6 H) 7.51 (d, J = 5.39 Hz, 1 H) 7.66-7.77 (m, 1 H) 7.87 (ddd, J = 8.34, 6.89, 1.55 Hz, 1 H) 8.11 (t, J = 8.60 Hz, 2 H) 8.46 (d, J = 2.07 Hz, 1 H) 8.55-8.65 (m, 2 H) 8.94 (d, J = 2.28 Hz, 1 H) 13.16 (s, 1 H) | 325 |
| 2G | 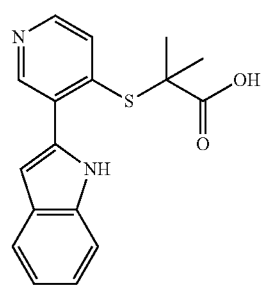 [SMILES: CC(C)(Sc1ccncc1-c1cc2ccccc2[nH]1)C(=O)O] | 1.56 (s, 6 H) 7.21 (dd, J = 8.81, 2.38 Hz, 1 H) 7.31 (d, J = 2.49 Hz, 1 H) 7.48 (dd, J = 8.40, 1.76 Hz, 1 H) 7.60 (d, J = 5.39 Hz, 1 H) 7.80 (s, 1 H) 7.85 (t, J = 8.29 Hz, 2 H) 8.37 (s, 1 H) 8.38 (d, J = 5.39 Hz, 1 H) | 313 |
| 2H | 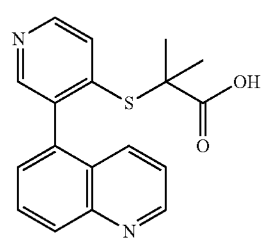 [SMILES: CC(C)(Sc1ccncc1-c1cccc2ncccc12)C(=O)O] | 1.40 (d, J = 8.50 Hz, 6 H) 7.49-7.55 (m, 2 H) 7.58 (d, J = 5.39 Hz, 1 H) 7.72 (d, J = 7.88 Hz, 1 H) 7.88 (dd, J = 8.50, 7.26 Hz, 1 H) 8.14 (d, J = 8.50 Hz, 1 H) 8.36 (s, 1 H) 8.58 (d, J = 5.39 Hz, 1 H) 8.97 (dd, J = 4.15, 1.66 Hz, 1 H) | 325 |
| 2I | 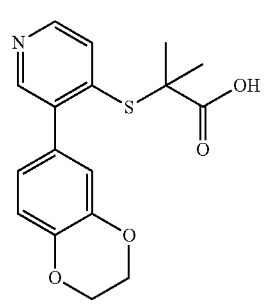 [SMILES: CC(C)(Sc1ccncc1-c1ccc2c(c1)OCCO2)C(=O)O] | 1.58 (s, 6 H) 4.29-4.35 (m, 3 H) 6.81-6.87 (m, 1 H) 6.89 (d, J = 2.07 Hz, 1 H) 6.91-6.97 (m, 1 H) 7.54 (d, J = 5.39 Hz, 1 H) 8.22 (s, 1 H) 8.31 (d, J = 5.39 Hz, 1 H) | 332 |

-continued

| Example | Structure | ¹H NMR δ ppm (400 MHz, DMSO-d₆) | MS (m/z) M + 1 |
|---------|-----------|----------------------------------|----------------|
| 2J | 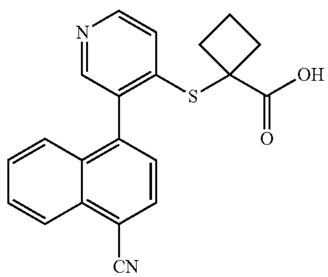 [SMILES: N#Cc1ccc(-c2cnccc2SC2(C(=O)O)CCC2)c2ccccc12] | ¹H NMR (400 MHz, DMSO-d₆, 25° C.) 13.30 (bs, 1H), 8.74 (d, J = 6.0 Hz, 1H), 8.58 (s, 1H), 8.37 (d, J = 7.6 Hz, 1H), 8.28 (d, J = 7.6 Hz, 1H), 7.92 (dd, J = 7.6, 7.6 Hz, 1H), 7.71-7.77 (m, 2H), 7.60 (d, J = 7.6 Hz, 1H), 7.45 (d, J = 6.0 Hz, 1H), 2.78-2.92 (m, 2H), 2.14-2.22 (m, 2H), 1.92-2.04 (m, 2H). | 360.93 |
| 2K | 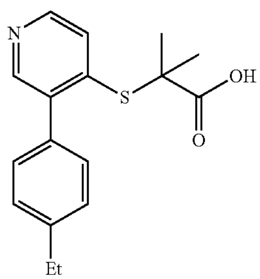 | 1.31 (t, J = 7.57 Hz, 3 H) 1.57 (s, 6 H) 2.74 (q, J = 7.53 Hz, 2 H) 7.28-7.36 (m, 4 H) 7.57 (d, J = 5.18 Hz, 1 H) 8.25 (br. s., 1 H) 8.34 (d, J = 4.35 Hz, 1 H) | 301 |
| 2L | 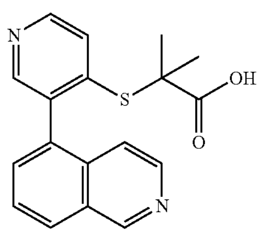 [SMILES: CC(C)(Sc1ccncc1-c1cccc2cnccc12)C(=O)O] | 1.44-1.56 (m, 6 H) 7.35-7.39 (m, 1 H) 7.73-7.79 (m, 2 H) 7.79-7.86 (m, 1 H) 8.25 (d, J = 7.05 Hz, 2 H) 8.42 (d, J = 6.01 Hz, 1 H) 8.45-8.50 (m, 1 H) 9.35 (s, 1 H) | 325 |
| 2M | 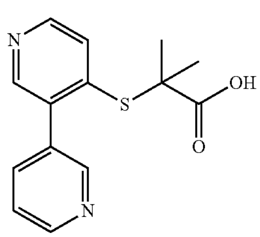 [SMILES: CC(C)(Sc1ccncc1-c1cccnc1)C(=O)O] | 1.58 (s, 6 H) 7.58 (dd, J = 7.57, 5.08 Hz, 1 H) 7.68 (d, J = 5.60 Hz, 1 H) 7.98 (dt, J = 7.88, 1.87 Hz, 1 H) 8.24 (s, 1 H) 8.36 (d, J = 5.39 Hz, 1 H) 8.56-8.65 (m, 2 H) | 275 |
| 2N | 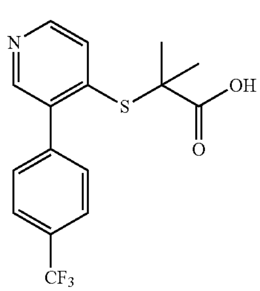 [SMILES: CC(C)(Sc1ccncc1-c1ccc(C(F)(F)F)cc1)C(=O)O] | 1.58 (s, 6 H) 7.60-7.70 (m, 3 H) 7.79 (d, J = 8.09 Hz, 2 H) 8.22 (s, 1 H) 8.35 (d, J = 5.60 Hz, 6 H) | 342 |

| Example | Structure | ¹H NMR δ ppm (400 MHz, DMSO-d₆) | MS (m/z) M + 1 |
|---------|-----------|-----------------------------------|----------------|
| 2O | 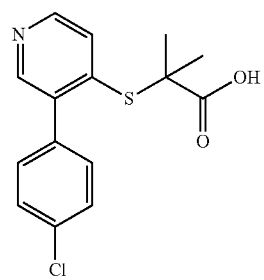 [SMILES: CC(C)(Sc1ccncc1-c1ccc(Cl)cc1)C(=O)O] | 1.42 (s, 6 H) 7.42 (d, J = 8.50 Hz, 2 H) 7.54 (d, J = 8.50 Hz, 2 H) 7.77 (d, J = 5.39 Hz, 1 H) 8.19 (s, 1 H) 8.31 (d, J = 5.39 Hz, 1 H) | 308 |
| 2P | 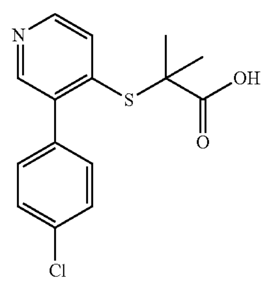 [SMILES: CC(C)(Sc1ccncc1-c1ccc(Cl)cc1)C(=O)O] | 1.57 (s, 6 H) 7.36-7.44 (m, 2 H) 7.45-7.54 (m, 2 H) 7.60 (d, J = 5.39 Hz, 1 H) 8.27 (s, 1 H) 8.37 (d, J = 5.39 Hz, 1 H) | 308 |
| 2Q | 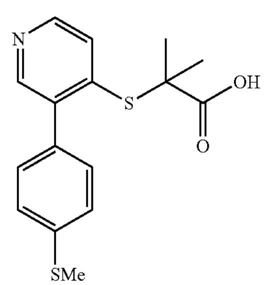 [SMILES: CSc1ccc(-c2cnccc2SC(C)(C)C(=O)O)cc1] | 1.57 (s, 6 H) 2.56 (s, 3 H) 7.30-7.40 (m, 4 H) 7.59 (d, J = 5.60 Hz, 1 H) 8.24 (s, 1 H) 8.33 (d, J = 5.39 Hz, 1 H) | 320 |
| 2R | 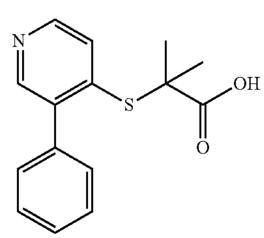 [SMILES: CC(C)(Sc1ccncc1-c1ccccc1)C(=O)O] | 1.56 (s, 6 H) 7.35-7.44 (m, 2 H) 7.44-7.52 (m, 3 H) 7.56 (d, J = 5.60 Hz, 1 H) 8.31 (s, 1 H) 8.39 (d, J = 5.60 Hz, 1 H) | 274 |
| 2S | 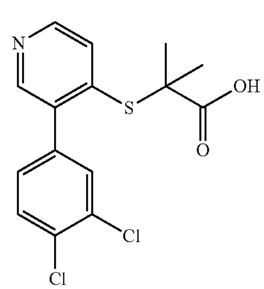 [SMILES: CC(C)(Sc1ccncc1-c1ccc(Cl)c(Cl)c1)C(=O)O] | 1.58 (s, 6 H) 7.37 (dd, J = 8.29, 2.07 Hz, 1 H) 7.57-7.67 (m, 3 H) 8.27 (s, 1 H) 8.38 (d, J = 5.60 Hz, 1 H) | 342 |

-continued

| Example | Structure | ¹H NMR δ ppm (400 MHz, DMSO-d₆) | MS (m/z) M + 1 |
|---------|-----------|----------------------------------|----------------|
| 2T | 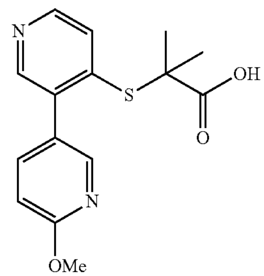 [SMILES: COc1ccc(-c2cnccc2SC(C)(C)C(=O)O)cn1] | 1.56 (s, 6 H) 4.00 (s, 3 H) 6.93 (dd, J = 8.50, 0.62 Hz, 1 H) 7.58 (d, J = 5.18 Hz, 1 H) 7.77 (dd, J = 8.71, 2.49 Hz, 1 H) 8.13-8.19 (m, 1 H) 8.37 (s, 1 H) 8.43 (d, J = 5.60 Hz, 1 H) | 305 |
| 2U | 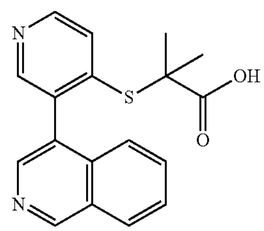 [SMILES: CC(C)(Sc1ccncc1-c1cncc2ccccc12)C(=O)O] | 1.51 (d, J = 8.71 Hz, 6 H) 7.48 (d, J = 7.67 Hz, 1 H) 7.68 (d, J = 5.60 Hz, 1 H) 7.78-7.83 (m, 2 H) 8.22-8.30 (m, 1 H) 8.37 (s, 1 H) 8.41 (s, 1 H) 8.57 (d, J = 5.39 Hz, 1 H) 9.38 (s, 1 H) | 325 |
| 2V | 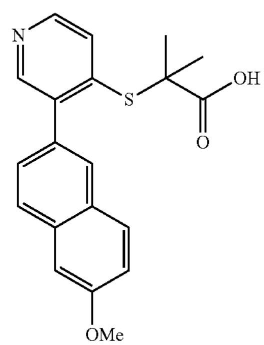 [SMILES: COc1ccc2cc(-c3cnccc3SC(C)(C)C(=O)O)ccc2c1] | 1.57 (s, 6 H) 3.94-4.00 (m, 3 H) 7.20 (dd, J = 9.02, 2.59 Hz, 1 H) 7.32 (d, J = 2.49 Hz, 1 H) 7.51 (dd, J = 8.40, 1.76 Hz, 1 H) 7.65 (d, J = 5.60 Hz, 1 H) 7.78-7.91 (m, 3 H) 8.28 (s, 1 H) 8.32 (d, J = 5.60 Hz, 1 H) | 354 |
| 2W | 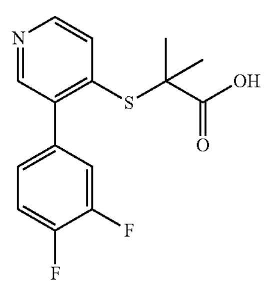 [SMILES: CC(C)(Sc1ccncc1-c1ccc(F)c(F)c1)C(=O)O] | 1.59 (s, 6 H) 7.24 (ddd, J = 6.27, 4.20, 1.97 Hz, 1 H) 7.32-7.46 (m, 2 H) 7.62 (d, J = 5.60 Hz, 1 H) 8.20 (s, 1 H) 8.32 (d, J = 5.18 Hz, 1 H) | 310 |
| 2X | 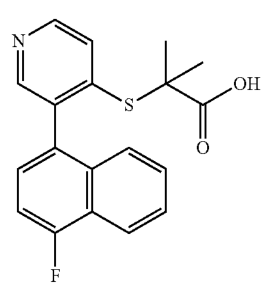 [SMILES: CC(C)(Sc1ccncc1-c1ccc(F)c2ccccc12)C(=O)O] | 1.46-1.57 (m, 6H) 7.31 (dd, J = 10.37, 7.88 Hz, 1 H) 7.35-7.46 (m, 2 H) 7.49-7.58 (m, 1 H) 7.59-7.68 (m, 1 H) 7.74 (d, J = 5.60 Hz, 1 H) 8.14-8.25 (m, 2 H) 8.43 (d, J = 5.39 Hz, 1 H) | 342 |

-continued

| Example | Structure | ¹H NMR δ ppm (400 MHz, DMSO-d₆) | MS (m/z) M + 1 |
|---|---|---|---|
| 2Y | 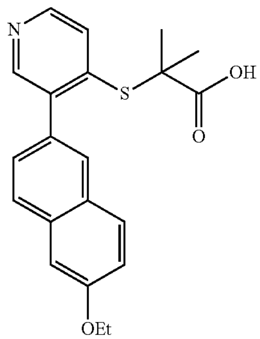 [SMILES: CCOc1ccc2cc(-c3cnccc3SC(C)(C)C(=O)O)ccc2c1] | 1.51 (t, J = 6.95 Hz, 3 H) 1.56 (s, 6 H) 4.22 (q, J = 6.98 Hz, 2 H) 7.21 (dd, J = 8.81, 2.38 Hz, 1 H) 7.31 (d, J = 2.49 Hz, 1 H) 7.48 (dd, J = 8.40, 1.76 Hz, 1 H) 7.60 (d, J = 5.39 Hz, 1 H) 7.80 (s, 1 H) 7.85 (t, J = 8.29 Hz, 2 H) 8.34-8.42 (m, 2 H) | 368 |
| 2Z | 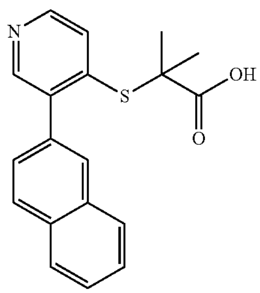 [SMILES: CC(C)(Sc1ccncc1-c1ccc2ccccc2c1)C(=O)O] | 1.58 (s, 6 H) 7.52-7.61 (m, 3 H) 7.68 (d, J = 5.60 Hz, 1 H) 7.88-7.99 (m, 4 H) 8.27 (s, 1 H) 8.32 (d, J = 5.60 Hz, 1 H) | 324 |
| 2AA | 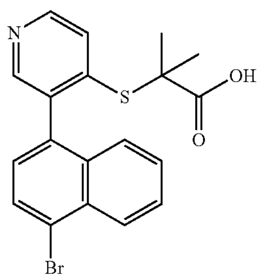 [SMILES: CC(C)(Sc1ccncc1-c1ccc(Br)c2ccccc12)C(=O)O] | 1.51 (d, J = 15.76 Hz, 6 H) 7.30 (d, J = 7.46 Hz, 1 H) 7.40 (d, J = 8.29 Hz, 1 H) 7.54 (td, J = 7.62, 1.14 Hz, 1 H) 7.64-7.72 (m, 2 H) 7.94 (d, J = 7.67 Hz, 1 H) 8.30 (s, 1 H) 8.35 (d, J = 8.50 Hz, 1 H) 8.50 (d, J = 5.60 Hz, 1 H) | 402, 404 |
| 2BB | 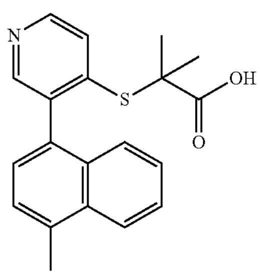 [SMILES: Cc1ccc(-c2cnccc2SC(C)(C)C(=O)O)c2ccccc12] | 1.50 (d, J = 17.41 Hz, 6 H) 2.78 (s, 3 H) 7.27 (d, J = 7.26 Hz, 1 H) 7.32-7.40 (m, 1 H) 7.40-7.48 (m, 2 H) 7.58 (t, J = 7.15 Hz, 1 H) 7.67 (d, J = 5.60 Hz, 1 H) 8.13 (d, J = 8.29 Hz, 1 H) 8.25 (s, 1 H) 8.45 (d, J = 5.60 Hz, 1 H) | 338 |
| 2CC | 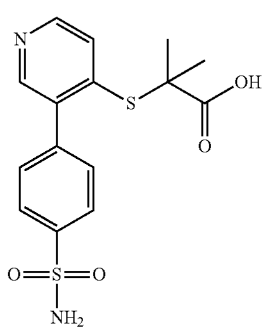 [SMILES: CC(C)(Sc1ccncc1-c1ccc(S(N)(=O)=O)cc1)C(=O)O] | 1.57 (s, 6 H) 7.57-7.67 (m, 3 H) 7.97-8.06 (m, 2 H) 8.28 (s, 1 H) 8.39 (d, J = 5.39 Hz, 1 H) | 353 |

-continued

| Example | Structure | ¹H NMR δ ppm (400 MHz, DMSO-d₆) | MS (m/z) M + 1 |
|---|---|---|---|
| 2DD | 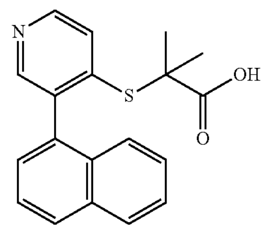 [SMILES: CC(C)(Sc1ccncc1-c1cccc2ccccc12)C(=O)O] | 1.41-1.52 (m, 6 H) 7.30-7.46 (m, 3 H) 7.45-7.60 (m, 2 H) 7.70 (d, J = 5.60 Hz, 1 H) 7.95 (t, J = 7.57 Hz, 2 H) 8.20 (s, 1 H) 8.40 (d, J = 5.60 Hz, 1 H) | 324 |
| 2EE | 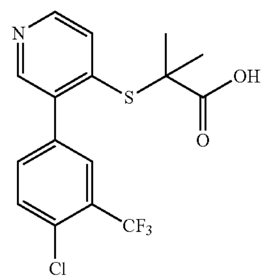 | 1.69 (s, 6 H) 7.70-7.78 (m, 1 H) 7.79-7.87 (m, 2 H) 7.91 (d, J = 2.07 Hz, 1 H) 8.52 (s, 1 H) 8.59 (d, J = 6.22 Hz, 1 H) | 376 |
| 2FF | 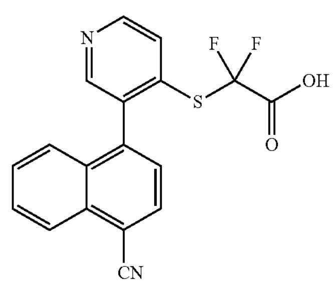 [SMILES: N#Cc1ccc(-c2cnccc2SC(F)(F)C(=O)O)c2ccccc12] | ¹H NMR (400 MHz, DMSO-d₆, 25° C.) 8.81 (d, J = 3.6 Hz, 1H), 8.66 (s, 1H), 8.33 (d, J = 7.6 Hz, 1H), 8.20 (d, J = 7.6 Hz, 1H), 7.85-7.98 (m, 2H), 7.79 (dd, J = 7.2, 7.2 Hz, 1H), 7.67 (d, J = 7.2, Hz, 1H), 7.48 (d, J = 7.2 Hz, 1H). | 356.88 |
| 2GG | 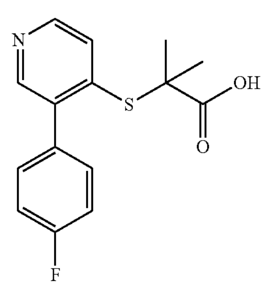 [SMILES: CC(C)(Sc1ccncc1-c1ccc(F)cc1)C(=O)O] | 1.48 (s, 6 H) 7.30-7.37 (m, 2 H) 7.39 (d, J = 5.18 Hz, 1 H) 7.42-7.49 (m, 2 H) 8.38 (s, 1 H) 8.50 (d, J = 5.39 Hz, 1 H) | 292 |
| 2HH | 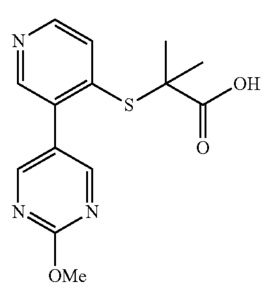 [SMILES: COc1ncc(-c2cnccc2SC(C)(C)C(=O)O)cn1] | 1.49 (s, 6 H) 3.18 (s, 3 H) 7.57 (d, J = 5.39 Hz, 1 H) 8.60 (s, 1 H) 8.64 (d, J = 5.60 Hz, 1 H) 8.72 (s, 2 H) | 306 |

-continued

| Example | Structure | ¹H NMR δ ppm (400 MHz, DMSO-d₆) | MS (m/z) M + 1 |
|---------|-----------|----------------------------------|----------------|
| 2II | 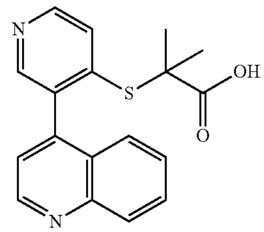 [SMILES: CC(C)(Sc1ccncc1-c1ccnc2ccccc12)C(=O)O] | 1.37 (d, J = 4.98 Hz, 6 H) 7.38-7.45 (m, 2 H) 7.59 (ddd, J = 8.29, 6.95, 1.14 Hz, 1 H) 7.82 (ddd, J = 8.34, 6.89, 1.35 Hz, 1 H) 7.91 (d, J = 5.39 Hz, 1 H) 8.13 (d, J = 7.88 Hz, 1 H) 8.24 (s, 1 H) 8.48 (d, J = 5.39 Hz, 1 H) 9.00 (d, J = 4.35 Hz, 1 H) | 325 |
| 2JJ | 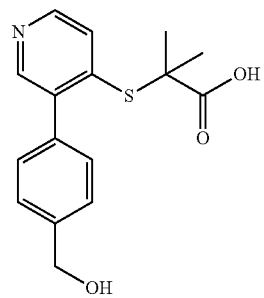 [SMILES: CC(C)(Sc1ccncc1-c1ccc(CO)cc1)C(=O)O] | 1.49 (s, 6 H) 4.59 (s, 2 H) 7.33-7.37 (m, 2 H) 7.38 (d, J = 5.39 Hz, 1 H) 7.40-7.46 (m, 2 H) 8.34 (s, 1 H) 8.47 (d, J = 5.39 Hz, 1 H) | 304 |
| 2KK | 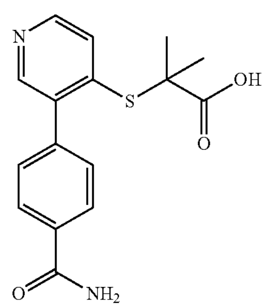 [SMILES: CC(C)(Sc1ccncc1-c1ccc(C(N)=O)cc1)C(=O)O] | 1.54 (s, 6 H) 7.48-7.57 (m, 4 H) 8.02 (d, J = 8.29 Hz, 2 H) 8.18 (br. s., 1 H) 8.50 (s, 1 H) 8.62 (d, J = 5.60 Hz, 1 H) | 317 |
| 2LL | 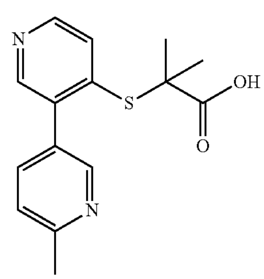 [SMILES: Cc1ccc(-c2cnccc2SC(C)(C)C(=O)O)cn1] | 1.47 (s, 6 H) 7.50 (d, J = 5.39 Hz, 1 H) 7.55 (d, J = 7.88 Hz, 1 H) 7.96 (d, J = 6.43 Hz, 1 H) 8.50 (s, 1 H) 8.54-8.61 (m, 2 H) | 289 |
| 2MM | 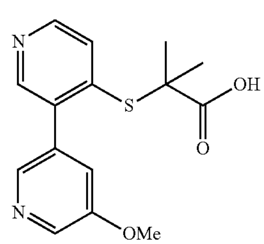 [SMILES: COc1cncc(-c2cnccc2SC(C)(C)C(=O)O)c1] | 1.59 (s, 6 H) 3.97 (s, 3 H) 7.72 (d, J = 6.01 Hz, 1 H) 7.84 (d, J = 1.66 Hz, 1 H) 8.43 (d, J = 1.66 Hz, 1 H) 8.57 (d, J = 2.70 Hz, 1 H) 8.71 (s, 1 H) 8.77 (d, J = 6.01 Hz, 1 H) | 305 |

-continued

| Example | Structure | ¹H NMR δ ppm (400 MHz, DMSO-d₆) | MS (m/z) M + 1 |
|---|---|---|---|
| 2NN | 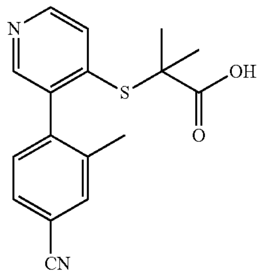 [SMILES: Cc1cc(C#N)ccc1-c1cnccc1SC(C)(C)C(=O)O] | 1.51 (d, J = 4.98 Hz, 6 H) 2.10 (s, 3 H) 7.35 (d, J = 7.88 Hz, 1 H) 7.43 (d, J = 5.39 Hz, 1 H) 7.78 (d, J = 7.88 Hz, 1 H) 7.87 (s, 1 H) 8.27 (s, 1 H) 8.55 (d, J = 4.77 Hz, 1 H) | 313 |
| 2OO | 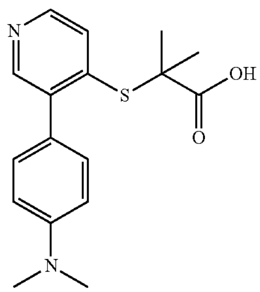 [SMILES: CN(C)c1ccc(-c2cnccc2SC(C)(C)C(=O)O)cc1] | 1.43 (s, 6 H) 2.97 (s, 6 H) 6.80 (d, J = 8.71 Hz, 2 H) 7.22 (d, J = 8.71 Hz, 2 H) 7.62 (d, J = 5.18 Hz, 1 H) 8.17 (s, 1 H) 8.25 (d, J = 5.39 Hz, 1 H) | 317 |
| 2PP | 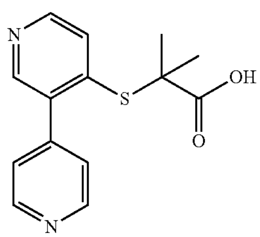 [SMILES: CC(C)(Sc1ccncc1-c1ccncc1)C(=O)O] | 1.47 (s, 6 H) 7.43-7.50 (m, 3 H) 8.45 (s, 1 H) 8.57 (d, J = 5.39 Hz, 1 H) 8.70 (d, J = 5.80 Hz, 2 H) | 275 |
| 2RR | 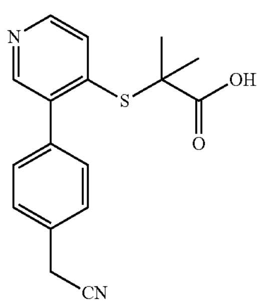 [SMILES: CC(C)(Sc1ccncc1-c1ccc(CC#N)cc1)C(=O)O] | 1.48 (s, 6 H) 4.15 (s, 2 H) 7.40 (d, J = 5.39 Hz, 1 H) 7.42-7.45 (m, 2 H) 7.45-7.50 (m, 2 H) 8.36 (s, 1 H) 8.49 (d, J = 5.39 Hz, 1 H) | 313 |
| 2SS | 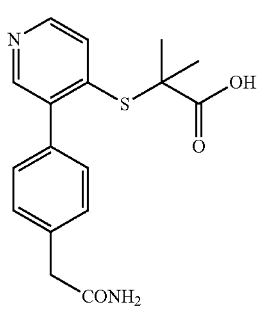 [SMILES: CC(C)(Sc1ccncc1-c1ccc(CC(N)=O)cc1)C(=O)O] | 1.50 (s, 6 H) 2.57 (s, 2 H) 6.98 (br. s., 1 H) 7.31-7.40 (m, 5 H) 7.59 (br. s., 1 H) 8.34 (s, 1 H) 8.47 (d, J = 5.39 Hz, 1 H) | 331 |

-continued

| Example | Structure | ¹H NMR δ ppm (400 MHz, DMSO-d₆) | MS (m/z) M + 1 |
|---------|-----------|-----------------------------------|----------------|
| 2TT | 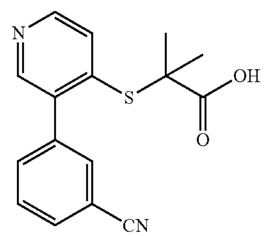 [SMILES: CC(C)(Sc1ccncc1-c1cccc(C#N)c1)C(=O)O] | 1.56 (s, 6 H) 7.61 (d, J = 5.39 Hz, 1 H) 7.66-7.72 (m, 1 H) 7.72-7.78 (m, 1 H) 7.80-7.88 (m, 2 H) 8.37 (s, 1 H) 8.46 (d, J = 5.18 Hz, 1 H) | 299 |
| 2UU | 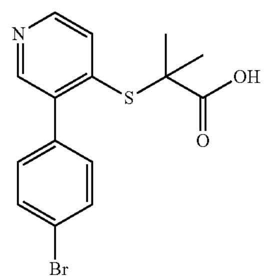 | 1.47 (s, 6 H) 7.37 (d, J = 8.50 Hz, 2 H) 7.43 (d, J = 5.39 Hz, 1 H) 7.70 (d, J = 8.50 Hz, 2 H) 8.37 (s, 1 H) 8.49 (d, J = 5.39 Hz, 1 H) | 352 |
| 2VV | 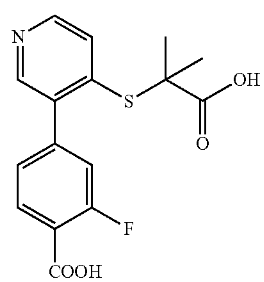 [SMILES: CC(C)(Sc1ccncc1-c1ccc(C(=O)O)c(F)c1)C(=O)O] | 1.49 (s, 6 H) 7.31 (dd, J = 7.88, 1.45 Hz, 1 H) 7.35-7.41 (m, 1 H) 7.43 (d, J = 5.39 Hz, 1 H) 7.71-7.79 (m, 2 H) 7.87 (br. s., 1 H) 8.42 (s, 1 H) 8.54 (d, J = 5.39 Hz, 1 H) | 335 |
| 2WW | 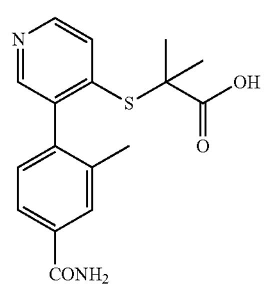 [SMILES: Cc1cc(C(N)=O)ccc1-c1cnccc1SC(C)(C)C(=O)O] | 1.51 (d, J = 5.80 Hz, 6 H) 2.10 (s, 3 H) 7.20 (d, J = 7.88 Hz, 1 H) 7.39 (d, J = 5.18 Hz, 1 H) 7.44 (s, 1 H) 7.77 (dd, J = 7.88, 1.24 Hz, 1 H) 7.84 (d, J = 7.88 Hz, 1 H) 8.05 (s, 5 H) 8.25 (br. s., 1 H) 8.51 (br. s., 1 H) | 331 |
| 2XX | 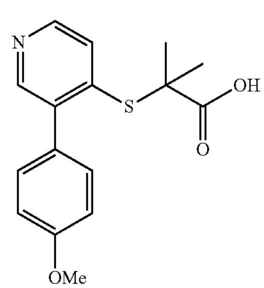 [SMILES: COc1ccc(-c2cnccc2SC(C)(C)C(=O)O)cc1] | 1.47 (s, 6 H) 7.05 (d, J = 8.71 Hz, 2 H) 7.33 (d, J = 8.71 Hz, 2 H) 7.40 (d, J = 5.39 Hz, 1 H) 8.31 (s, 1 H) 8.42 (d, J = 5.39 Hz, 1 H) | 304 |

-continued

| Example | Structure | $^1$H NMR δ ppm (400 MHz, DMSO-$d_6$) | MS (m/z) M + 1 |
|---|---|---|---|
| 2YY | 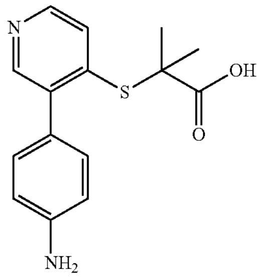 [SMILES: CC(C)(Sc1ccncc1-c1ccc(N)cc1)C(=O)O] | 1.43 (s, 6 H) 5.30 (br. s., 2 H) 6.63 (d, J = 8.50 Hz, 2 H) 7.04 (d, J = 8.29 Hz, 2 H) 7.67 (d, J = 5.39 Hz, 1 H) 8.11 (s, 1 H) 8.19 (d, J = 5.39 Hz, 6 H) | 289 |
| 2ZZ | 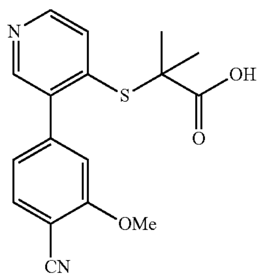 [SMILES: COc1cc(-c2cnccc2SC(C)(C)C(=O)O)ccc1C#N] | 1.49 (s, 6 H) 3.99 (s, 3 H) 7.16 (dd, J = 7.88, 1.45 Hz, 1 H) 7.30 (d, J = 1.04 Hz, 1 H) 7.44 (d, J = 5.39 Hz, 1 H) 7.84 (d, J = 7.88 Hz, 1 H) 8.48 (s, 1 H) 8.56 (d, J = 5.39 Hz, 1 H) | 329 |
| 2AAA | 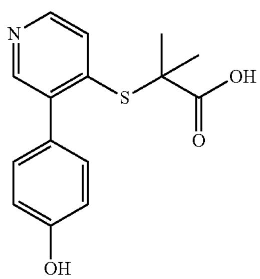 | 1.49 (s, 6 H) 6.87 (d, J = 8.50 Hz, 2 H) 7.21 (d, J = 8.50 Hz, 2 H) 7.33 (d, J = 5.39 Hz, 1 H) 8.32 (s, 1 H) 8.42 (d, J = 5.39 Hz, 1 H) 9.70 (s, 1 H) 13.14 (br. s., 1 H) | 290 |
| 2BBB | 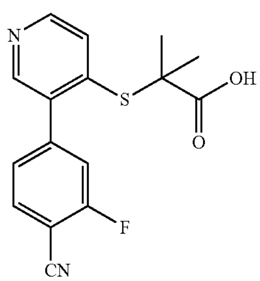 [SMILES: CC(C)(Sc1ccncc1-c1ccc(C#N)c(F)c1)C(=O)O] | 1.45 (s, 6 H) 7.46-7.55 (m, 2 H) 7.69 (dd, J = 10.26, 1.14 Hz, 1 H) 8.06 (t, J = 7.46 Hz, 1 H) 8.45 (s, 1 H) 8.56 (d, J = 5.18 Hz, 1 H) | 317 |
| 2CCC | 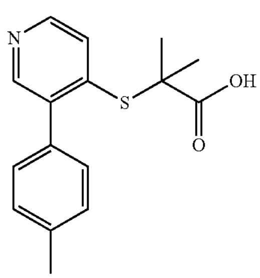 [SMILES: Cc1ccc(-c2cnccc2SC(C)(C)C(=O)O)cc1] | 1.48 (s, 6 H) 2.39 (s, 3 H) 7.25-7.33 (m, 4 H) 7.36 (d, J = 5.39 Hz, 1 H) 8.34 (s, 1 H) 8.46 (d, J = 5.39 Hz, 1 H) | 288 |

-continued

| Example | Structure | ¹H NMR δ ppm (400 MHz, DMSO-d₆) | MS (m/z) M + 1 |
|---|---|---|---|
| 2DDD | (pyridine-phenyl-NHCOMe with S-C(Me)₂-COOH) | 1.43 (s, 6 H) 2.10 (s, 3 H) 7.31 (d, J = 8.50 Hz, 2 H) 7.68 (d, J = 8.71 Hz, 3 H) 8.19 (s, 1 H) 8.29 (d, J = 5.39 Hz, 1 H) 10.22 (s, 1 H) | 331 |
| 2EEE | (pyridine-phenyl-SO₂Me with S-C(Me)₂-COOH) | 1.44 (s, 6 H) 3.33 (s, 3 H) 7.69 (d, J = 8.50 Hz, 2 H) 7.73 (d, J = 5.39 Hz, 1 H) 8.03 (d, J = 8.29 Hz, 2 H) 8.27 (s, 1 H) 8.40 (d, J = 5.39 Hz, 1 H) | 352 |
| 2FFF | (pyridine-(Cl,CN-phenyl) with S-C(Me)₂-COOH) | 1.46 (s, 6 H) 7.47 (d, J = 5.18 Hz, 1 H) 7.63 (dd, J = 7.98, 1.55 Hz, 1 H) 7.87 (d, J = 1.45 Hz, 1 H) 8.11 (d, J = 8.09 Hz, 1 H) 8.48 (s, 1 H) 8.59 (d, J = 5.18 Hz, 1 H) | 333 |
| 2GGG | (pyridine-phenyl-SH with S-C(Me)₂-COOH) | 1.48 (s, 6 H) 7.21-7.26 (m, 2 H) 7.35-7.41 (m, 2 H) 7.76 (d, J = 5.39 Hz, 1 H) 8.21 (s, 1 H) 8.28 (d, J = 5.39 Hz, 1 H) | 306 |
| 2HHH | (pyridine-(F,COOH-phenyl) with S-C(Me)₂-COOH) | 1.43 (s, 6 H) 7.48-7.54 (m, 2 H) 7.75-7.81 (m, 1 H) 7.88 (dd, J = 7.88, 1.24 Hz, 1 H) 8.43 (s, 1 H) 8.57 (d, J = 5.18 Hz, 1 H) | 336 |

-continued
| Example | Structure | $^1$H NMR δ ppm (400 MHz, DMSO-$d_6$) | MS (m/z) M + 1 |
|---|---|---|---|
| 2III | 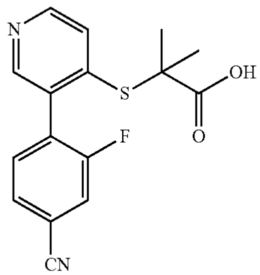 [SMILES: CC(C)(Sc1ccncc1-c1ccc(C#N)cc1F)C(=O)O] | 1.42 (s, 6 H) 7.58 (d, J = 5.39 Hz, 1 H) 7.64 (t, J = 7.57 Hz, 1 H) 7.85 (dd, J = 7.88, 1.24 Hz, 1 H) 8.00-8.07 (m, 1 H) 8.42 (s, 1 H) 8.57 (d, J = 4.98 Hz, 1 H) | 317 |
| 2JJJ | 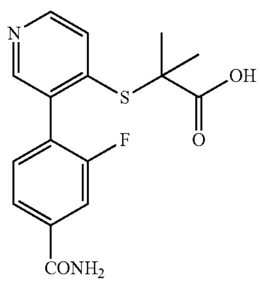 [SMILES: CC(C)(Sc1ccncc1-c1ccc(C(N)=O)cc1F)C(=O)O] | 1.44 (s, 6 H) 7.44-7.53 (m, 2 H) 7.64 (s, 1 H) 7.75-7.86 (m, 2 H) 8.18 (br. s., 1 H) 8.44 (s, 1 H) 8.58 (d, J = 5.39 Hz, 1 H) | 335 |
Example 3
Preparation of Compounds of Formula (I-C)
Compounds of formula (I-C) may be prepared according to the general scheme shown below:
Scheme I-C:
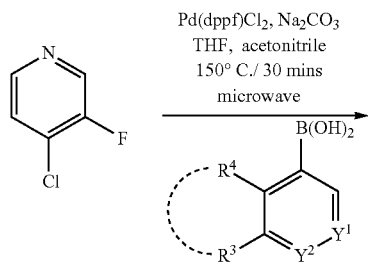
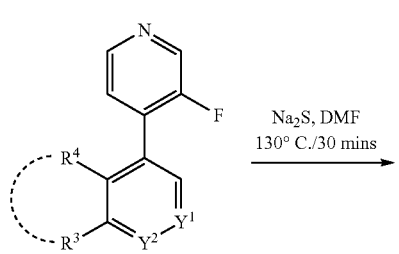
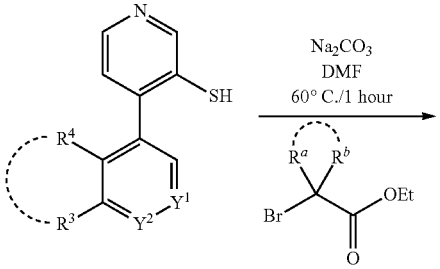
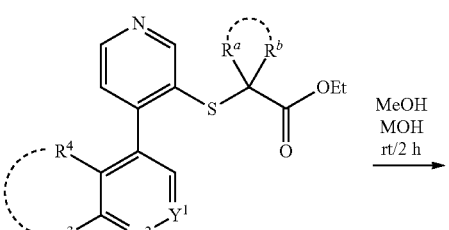
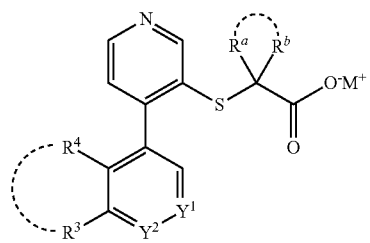

Example 3A

2-(4-(4-Cyanophenyl)pyridin-3-ylthio)-2-methylpropanoic acid

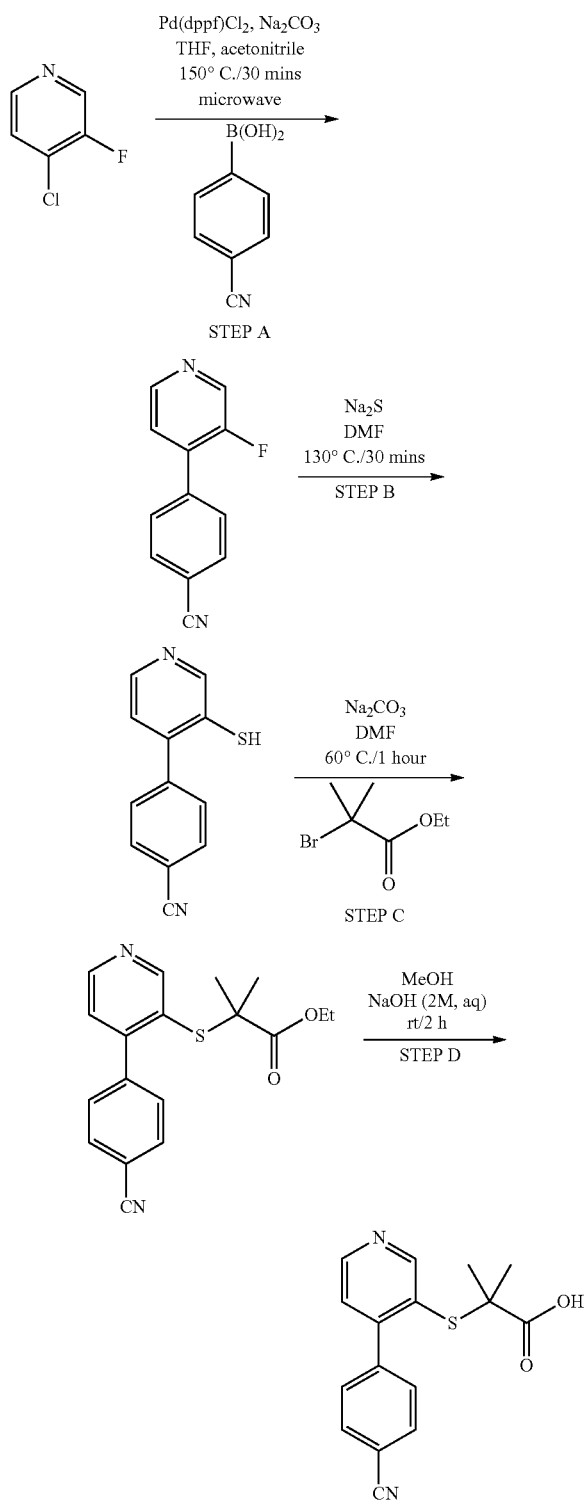

Step A: 4-(3-Fluoropyridin-4-yl)benzonitrile

4-Cyanophenylboronic acid (1.77 g, 12 mmol) and Pd(dppf)Cl$_2$ (400 mg, 5% mol) were weighed into a 20 mL microwave reaction vial. A solution of 4-chloro-3-fluoropyridine (1.31 g, 10 mmol) in THF (6 mL), acetonitrile (6 mL), and aqueous sodium carbonate solution (2M, 0.8 mL) was added. The resulting suspension was degassed by bubbling N$_2$ for 1 min. The mixture was then heated to 150° C. for 30 minutes under microwave irradiation. The mixture was loaded on to a 5 g ISCO loading cartridge and eluded with a gradient of 0-80% ethyl acetate in hexane on a 40 g ISCO column to yield ethyl 2-(4-(4-cyanophenyl)pyridin-3-ylthio)-2-methylpropanoate as a white powder (1.08 g, 54%).

Step B: 4-(3-Mercaptopyridin-4-yl)benzonitrile

A mixture of 4-(3-fluoropyridin-4-yl)benzonitrile (1.08 g, 5.4 mmol) and sodium sulfide (0.84 g, 10.8 mmol) in DMF (20 mL) was stirred at 130° C. for 0.5 hours. While the reaction was cooled in ice water bath, aqueous HCl (6N, 2.5 mL) was added drop wise with rigorous stirring. The resulting yellow paste was concentrated using rotary evaporation on a water bath (80° C.) to dryness. The resulting yellow solid was extracted with methanol (4×20 mL). The combined extracts were concentrated to dryness to give a yellow solid (1.1 g, 96%).

Step C: Ethyl 2-(4-(4-cyanophenyl)pyridin-3-ylthio)-2-methylpropanoate

A mixture of 4-(3-mercaptopyridin-4-yl)benzonitrile (1.1 g, 5.2 mmol), ethyl 2-bromoisobutyrate (2.0 g, 10.4 mmol), and sodium carbonate (1.6 g, 15.5 mmol) in DMF (20 mL) was stirred at 60° C. for 1 hour. The reaction mixture was partitioned between water (20 mL) and ethyl acetate (20 mL). The organic layer was washed with water (2×20 mL) and saturated sodium chloride solution (20 mL). The aqueous washes were back extracted with ethyl acetate (2×20 mL). The combined organic extracts were dried over sodium sulfate, concentrated, and purified by normal phase chromatography using a gradient of 0-25% ethyl acetate in hexane to yield ethyl 2-(3-bromopyridin-4-ylthio)-2-methylpropanoate as a pale yellow oil (0.25 g, 15%).

Step D: 2-(4-(4-Cyanophenyl)pyridin-3-ylthio)-2-methylpropanoic acid

Methanol (1 mL) and aqueous sodium hydroxide solution (2M, 1 mL) were added to ethyl 2-(4-(4-cyanophenyl)pyridin-3-ylthio)-2-methylpropanoate (0.25 g, 0.77 mmol) and stirred at ambient temperature for 2 hours. The volume was reduced (~1 mL) by rotary evaporation and the resulting residue treated with aqueous HCl (6N) with stirring to pH 6, resulting in formation of a white precipitate, which was isolated by filtration. The solid was washed with water (6×1 mL), air dried for 1 hour and dried under vacuum over P$_2$O$_5$ overnight to give a white powder (0.072 g, 32%).

$^1$H NMR (400 MHz, DMSO-d$_6$) δ ppm 1.17 (s, 6H) 7.50 (d, J=4.98 Hz, 1H) 7.67 (d, J=8.29 Hz, 2H) 7.97 (d, J=8.29 Hz, 2H) 8.69 (d, J=4.98 Hz, 1H) 8.73 (s, 1H) 12.65 (br, 1H).

MS (m/z), M+1, 299.

Examples 3B-3Z

The compounds in the table below are prepared according to the procedures described in example 3A.

| Example | Structure |
|---|---|
| 3B | 3-pyridyl-4-phenyl with S-C(CH3)2-COOH |
| 3C | 3-pyridyl-4-(3,4-dichlorophenyl) with S-C(CH3)2-COOH |
| 3D | 3-pyridyl-4-(4-ethylphenyl) with S-C(CH3)2-COOH |
| 3E | 3-pyridyl-4-(1-naphthyl) with S-C(CH3)2-COOH |
| 3F | 3-pyridyl-4-(2-naphthyl) with S-C(CH3)2-COOH |
| 3G | 3-pyridyl-4-(8-methylnaphth-1-yl) with S-C(CH3)2-COOH |
| 3H | 3-pyridyl-4-(2-pyridyl) with S-C(CH3)2-COOH |
| 3I | 3-pyridyl-4-(3-pyridyl) with S-C(CH3)2-COOH |
| 3J | 3-pyridyl-4-(4-pyridyl) with S-C(CH3)2-COOH |
| 3K | 3-pyridyl-4-(6-methoxypyridin-3-yl) with S-C(CH3)2-COOH |
| 3L | 3-pyridyl-4-(pyrimidin-5-yl) with S-C(CH3)2-COOH |

-continued

| Example | Structure |
|---------|-----------|
| 3M | 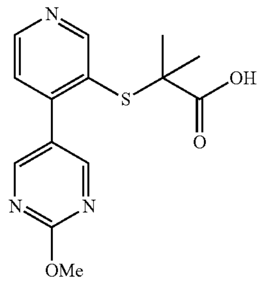 [SMILES: COc1ncc(-c2ccncc2SC(C)(C)C(=O)O)cn1] |
| 3O | 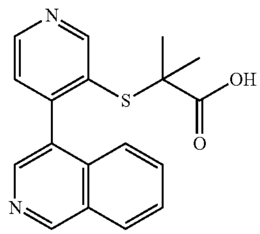 [SMILES: CC(C)(Sc1cnccc1-c1cncc2ccccc12)C(=O)O] |
| 3P | 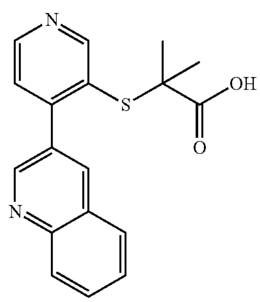 [SMILES: CC(C)(Sc1cnccc1-c1cnc2ccccc2c1)C(=O)O] |
| 3Q | 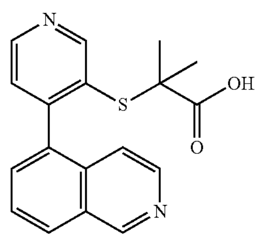 [SMILES: CC(C)(Sc1cnccc1-c1cccc2cnccc12)C(=O)O] |
| 3R | 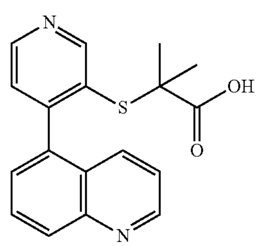 [SMILES: CC(C)(Sc1cnccc1-c1cccc2ncccc12)C(=O)O] |
| 3S | 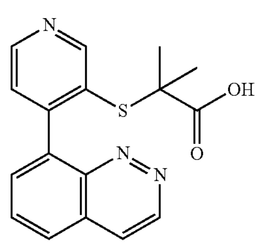 [SMILES: CC(C)(Sc1cnccc1-c1cccc2ccnnc12)C(=O)O] |

-continued

| Example | Structure |
|---------|-----------|
| 3T | 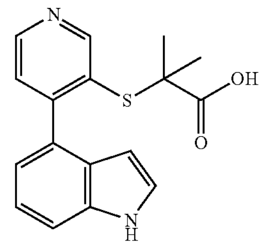 [SMILES: CC(C)(Sc1cnccc1-c1cccc2[nH]ccc12)C(=O)O] |
| 3U | 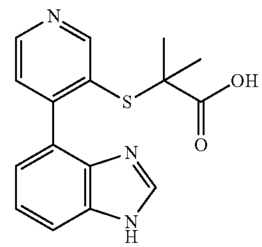 [SMILES: CC(C)(Sc1cnccc1-c1cccc2[nH]cnc12)C(=O)O] |
| 3V | 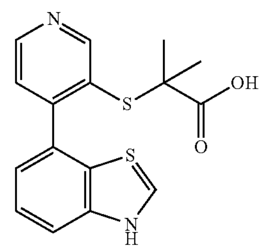 |
| 3W | 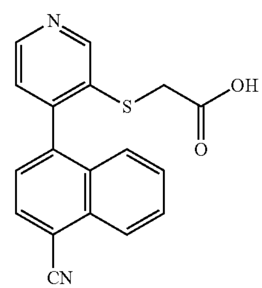 [SMILES: N#Cc1ccc(-c2ccncc2SCC(=O)O)c2ccccc12] |
| 3X | 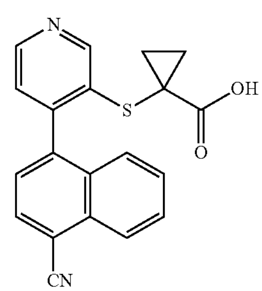 [SMILES: N#Cc1ccc(-c2ccncc2SC2(C(=O)O)CC2)c2ccccc12] |
| 3Y | 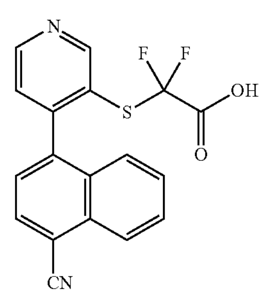 [SMILES: N#Cc1ccc(-c2ccncc2SC(F)(F)C(=O)O)c2ccccc12] |

-continued
| Example | Structure |
|---------|-----------|
| 3Z | 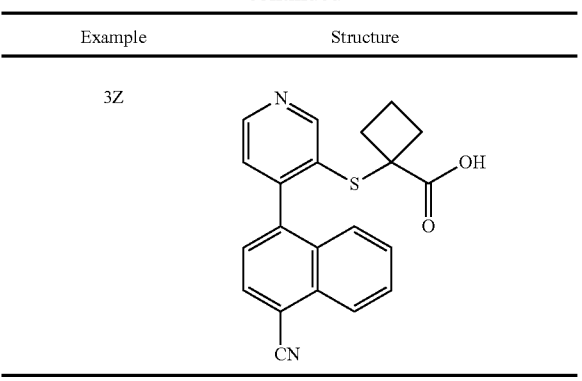 |
Example 4
Preparation of Compounds of Formula (I-D)
Compounds of formula (I-D) may be prepared according to the general schemes shown below:
Scheme I-D-b:
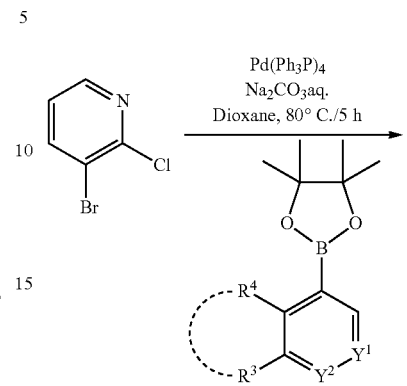
Scheme I-D-a:
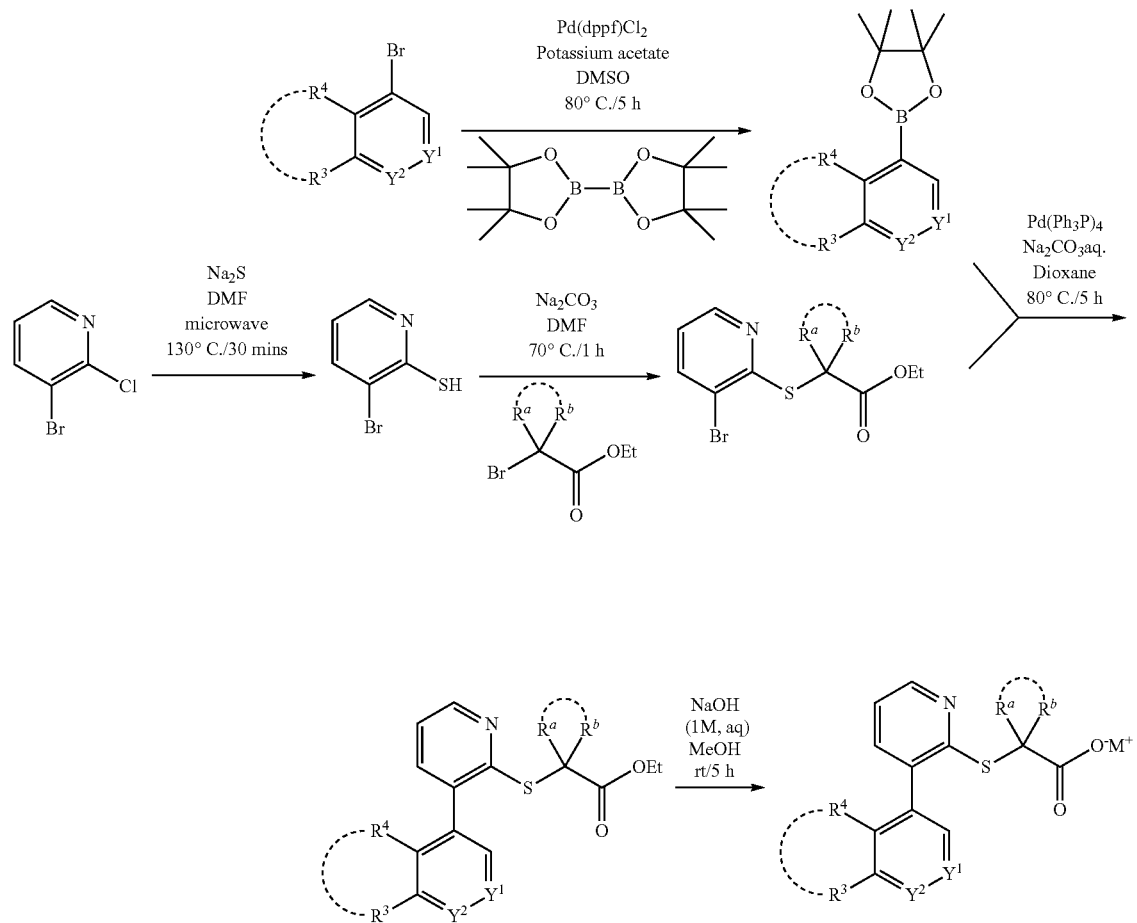

131
-continued
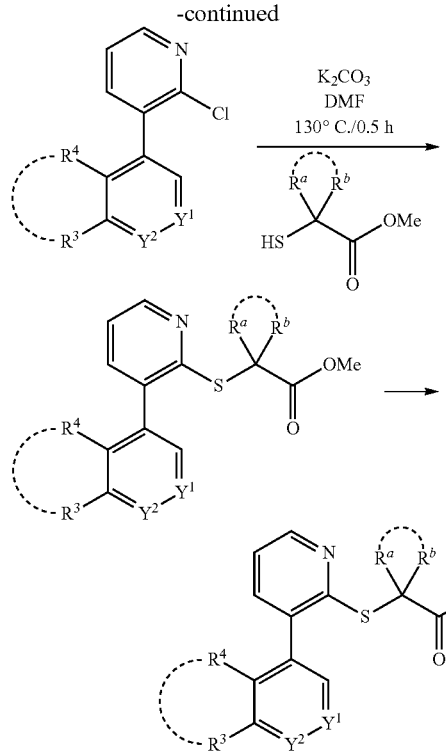
Scheme I-D-c:
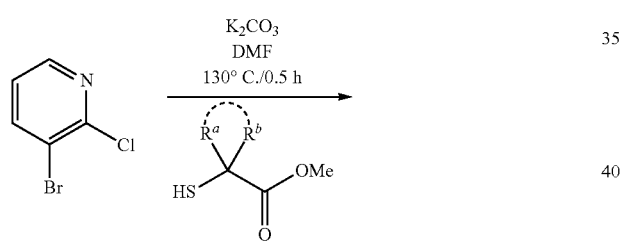
132
-continued
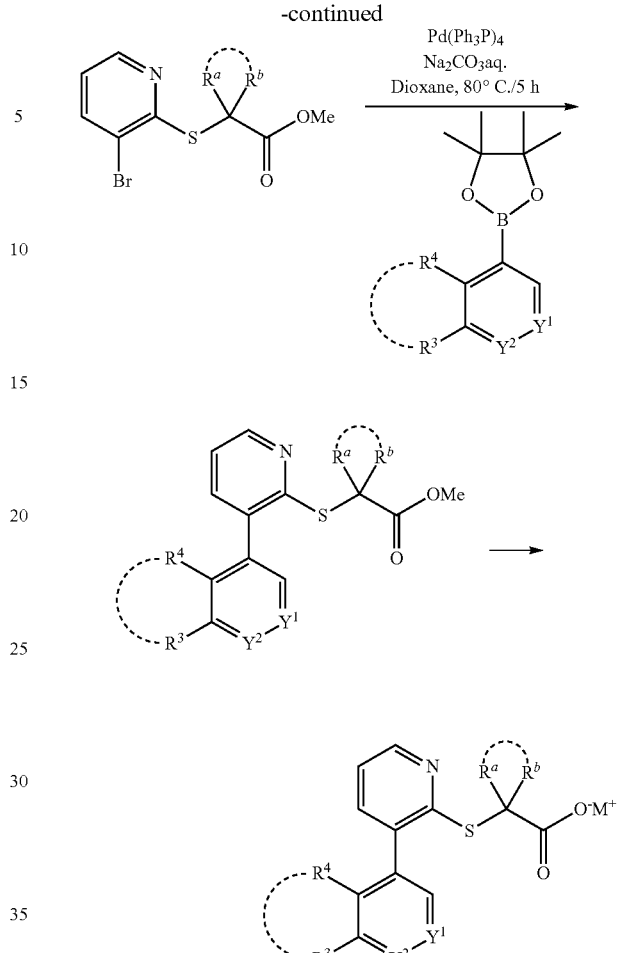
Example 4A
2-(3-(4-Cyanonaphthalen-1-yl)pyridin-2-ylthio)-2-methylpropanoic acid
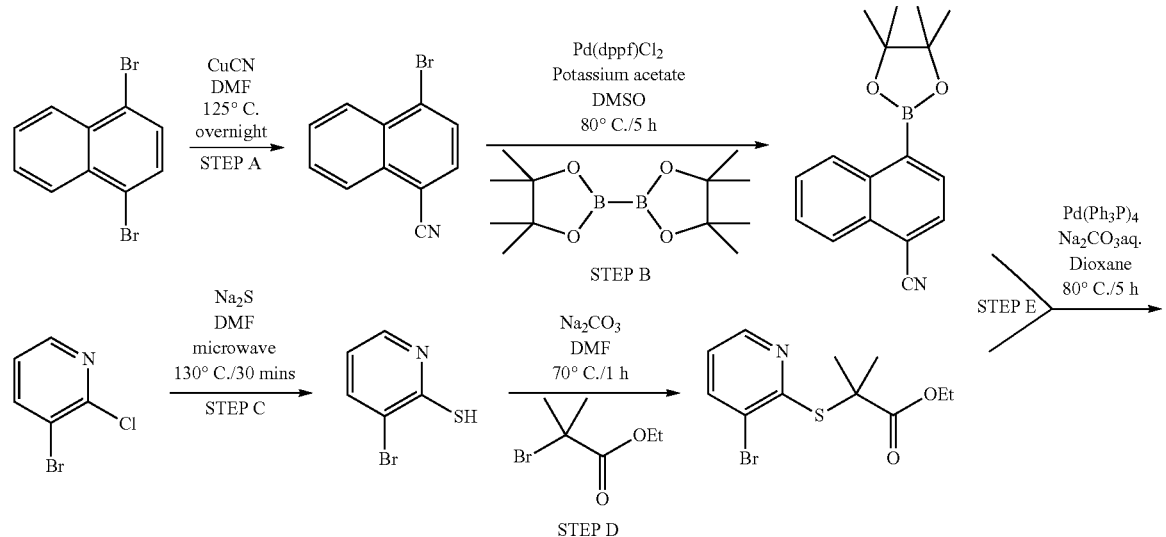

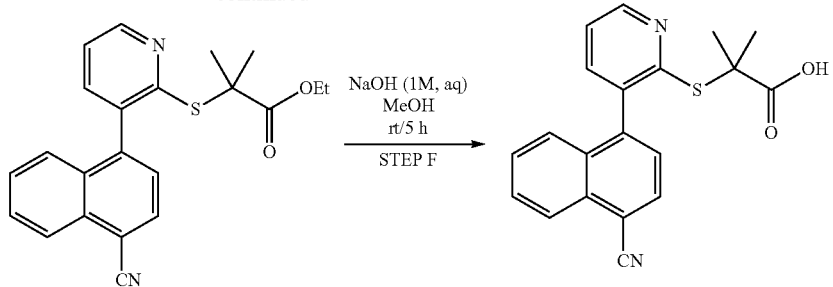

Step A: 4-Bromo-1-naphthonitrile

A mixture of 1,4-dibromonaphthalene (24.06 g, 84 mmol) and copper cyanide (6.02 g, 67 mmol) in DMF (85 mL) was heated to 125° C. overnight. The mixture was partially concentrated to remove DMF and the resulting residue washed with aqueous ammonium hydroxide and extracted with ethyl acetate. The organic layer was concentrated and purified by chromatography to yield 4-bromo-1-naphthonitrile (5.13 g, 26%).

Step B: 4-(4,4,5,5-Tetramethyl-1,3,2-dioxaborolan-2-yl)-1-naphthonitrile

A mixture of 4-bromo-1-naphthonitrile (4.58 g, 19.7 mmol), bis(pinacol)diboron (5.00 g, 19.7 mmol), Pd(dppf)Cl$_2$ (0.49 g, 0.6 mmol) and potassium acetate (5.78 g, 59.1 mmol) in DMSO was heated to 80° C. for 5 hours. The reaction mixture was washed with HCl aq. 1M, extracted with ethyl acetate and purified by chromatography to yield 4-(4,4,5,5-tetramethyl-1,3,2-dioxaborolan-2-yl)-1-naphthonitrile (2.00 g, 36%).

Step C: 3-bromopyridine-2-thiol

A mixture of 3-bromo-2-chloropyridine (0.769 g, 4 mmol) and sodium sulfide (0.336 g, 6 mmol) in DMF (3 mL) was heated under microwave irradiation at 130° C. for 0.5 hour. Water (50 mL) and ethyl acetate (20 mL) were added and the layers separated. The aqueous layer was acidified to pH 6 resulting in the formation of a precipitate, which was isolated by filtration and dried under vacuum to yield the product as a yellow solid (0.42 g, 55%).

Step D: Ethyl 2-(3-bromopyridin-2-ylthio)-2-methylpropanoate

A mixture of 3-bromopyridine-2-thiol (189 mg, 1 mmol), ethyl-2-bromoisobutyrate (390 mg, 2 mmol) and sodium carbonate (159 mg, 1.5 mmol) in DMF (2 mL) was heated to 70° C. for 1 hour. The reaction mixture was neutralized with HCl aq. 1M and extracted with ethyl acetate. The organic layer was dried over Mg$_2$SO$_4$, concentrated and purified by chromatography to yield ethyl 2-(3-bromopyridin-2-ylthio)-2-methylpropanoate (0.271 g, 89%).

Step E: Ethyl 2-(3-(4-cyanonaphthalen-1-yl)pyridin-2-ylthio)-2-methylpropanoate A mixture of ethyl 2-(3-bromopyridin-2-ylthio)-2-methylpropanoate (271 mg, 0.89 mmol), 4-(4,4,5,5-tetramethyl-1,3,2-dioxaborolan-2-yl)-1-naphthonitrile (248 mg, 0.89 mmol), palladium tetrakis triphenylphoshine (51 mg, 0.044 mmol) and aqueous sodium carbonate solution (2M, 1.5 mL, 3 mmol) in dioxane (3 mL) was degassed and heated to 80° C. for 5 hours. The mixture was washed with water and extracted with ethyl acetate. The organic layer was dried with Mg$_2$SO$_4$, concentrated and purified by chromatography to yield ethyl 2-(3-(4-cyanonaphthalen-1-yl)pyridin-2-ylthio)-2-methylpropanoate (0.121 g, 36%).

Step F: 2-(3-(4-cyanonaphthalen-1-yl)pyridin-2-ylthio)-2-methylpropanoic acid Ethyl 2-(3-(4-cyanonaphthalen-1-yl)pyridin-2-ylthio)-2-methylpropanoate (121 mg, 0.32 mmol) in a mixture of aqueous sodium hydroxide solution (1M, 2 mL) and methanol (5 mL) was stirred at room temperature for 5 hours. Methanol was partially removed and the resulting residue acidified causing precipitation of the product 2-(3-(4-cyanonaphthalen-1-yl)pyridin-2-ylthio)-2-methylpropanoic acid. Solid product was isolated by filtration and dried under vacuum (0.065 g, 0.187 mmol, 60%).

$^1$H NMR (400 MHz, DMSO-d$_6$) δ ppm 12.47 (s, 1H), 8.56 (d, J=4.8 Hz, 1H), 8.29 (d, J=7.2 Hz, 1H), 8.25 (d, J=8.4 Hz, 1H), 7.88 (dd, J=7.6, 7.6 Hz, 1H), 7.72 (dd, J=7.6, 7.6 Hz, 1H), 7.66 (d, J=7.2 Hz, 1H), 7.62 (d, J=8.4 Hz, 1H), 7.50 (d, J=8.8 Hz, 1H), 7.35 (dd, J=4.8, 7.6 Hz, 1H), 1.49 (s, 6H). MS (m/z), M+1, 349.08.

Examples 4B, 4C

The compounds in the table below were prepared according to the procedure described in example 4A.

| Example | Structure | $^1$H NMR (400 MHz, DMSO-d$_6$) δ ppm | MS (m/z), M + 1 |
| --- | --- | --- | --- |
| 4B | 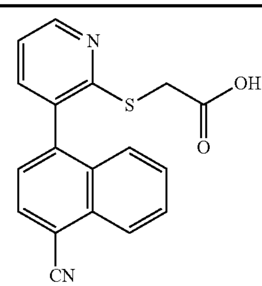 | 8.64 (d, J = 3.6 Hz, 1H), 8.41 (d, J = 8.4 Hz, 1H), 8.04 (d, J = 7.2 Hz, 1H), 7.81 (dd, J = 7.2, 7.2 Hz, 1H), 7.72 (d, J = 5.6 Hz, 1H), 7.65 (dd, J = 7.2, 7.2 Hz, 1H), 7.45-7.53 (m, 3H), 3.74 (d, J = 14.4 Hz, 1H), 3.66 (d, J = 14.4 Hz, 1H) | 321.07 |

-continued

| Example | Structure | ¹H NMR (400 MHz, DMSO-d₆) δ ppm | MS (m/z), M + 1 |
|---|---|---|---|
| 4C | [structure] | 12.80 (s, 1H), 8.54 (d, J = 4.8 Hz, 1H), 8.31 (d, J = 7.2 Hz, 1H), 8.26 (d, J = 8.4 Hz, 1H), 7.88 (dd, J = 7.6, 7.6 Hz, 1H), 7.71 (dd, J = 7.6, 7.6 Hz, 1H), 7.64 (d, J = 7.2 Hz, 2H), 7.55 (d, J = 8.4 Hz, 1H), 7.33 (dd, J = 4.8, 7.6 Hz, 1H), 2.65-2.75 (m, 2H), 2.05-2.15 (m, 2H), 1.90-2.01 (m, 2H) | 360.93 |

Examples 4D-4Z

The compounds in the table below are prepared according to the procedures described in example 4A.

| Example | Structure |
|---|---|
| 4D | [structure] |
| 4E | [structure] |
| 4F | [structure] |
| 4G | [structure] |
| 4H | [structure] |
| 4I | [structure] |
| 4J | [structure] |
| 4K | [structure] |

-continued

| Example | Structure |
|---------|-----------|
| 4L | 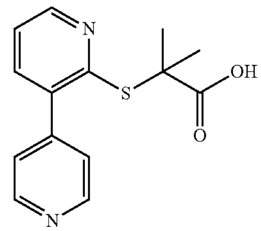 [SMILES: CC(C)(Sc1ncccc1-c1ccncc1)C(=O)O] |
| 4M | 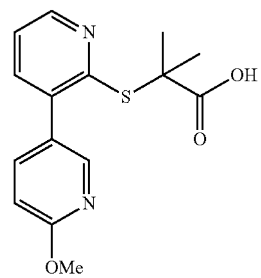 [SMILES: COc1ccc(-c2cccnc2SC(C)(C)C(=O)O)cn1] |
| 4N | 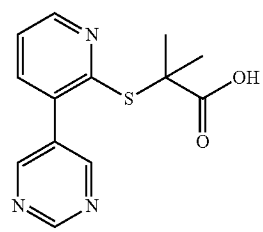 [SMILES: CC(C)(Sc1ncccc1-c1cncnc1)C(=O)O] |
| 4O | 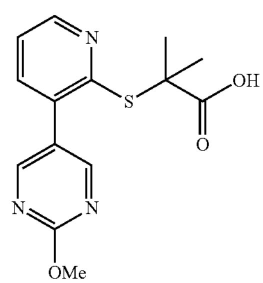 [SMILES: COc1ncc(-c2cccnc2SC(C)(C)C(=O)O)cn1] |
| 4Q | 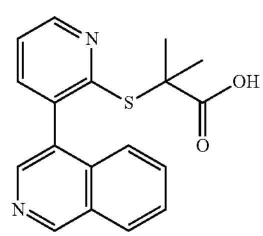 [SMILES: CC(C)(Sc1ncccc1-c1cncc2ccccc12)C(=O)O] |
| 4R | 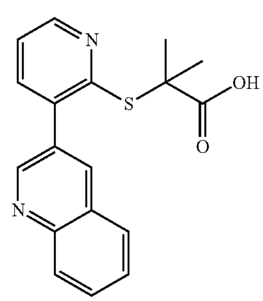 [SMILES: CC(C)(Sc1ncccc1-c1cnc2ccccc2c1)C(=O)O] |

-continued

| Example | Structure |
|---------|-----------|
| 4S | 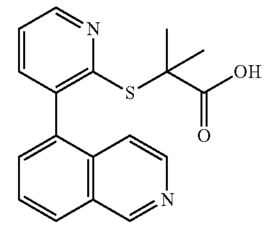 [SMILES: CC(C)(Sc1ncccc1-c1cccc2cnccc12)C(=O)O] |
| 4T | 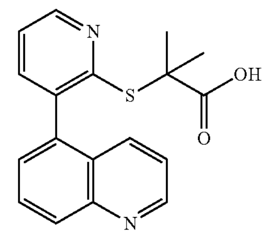 [SMILES: CC(C)(Sc1ncccc1-c1cccc2ncccc12)C(=O)O] |
| 4U | 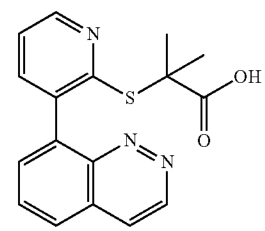 [SMILES: CC(C)(Sc1ncccc1-c1cccc2ccnnc12)C(=O)O] |
| 4V | 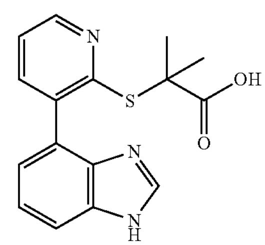 [SMILES: CC(C)(Sc1ncccc1-c1cccc2[nH]cnc12)C(=O)O] |
| 4W | 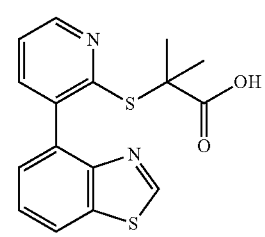 [SMILES: CC(C)(Sc1ncccc1-c1cccc2scnc12)C(=O)O] |
| 4X | 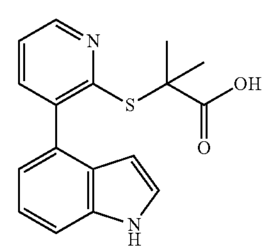 [SMILES: CC(C)(Sc1ncccc1-c1cccc2[nH]ccc12)C(=O)O] |

| Example | Structure |
|---|---|
| 4Y | 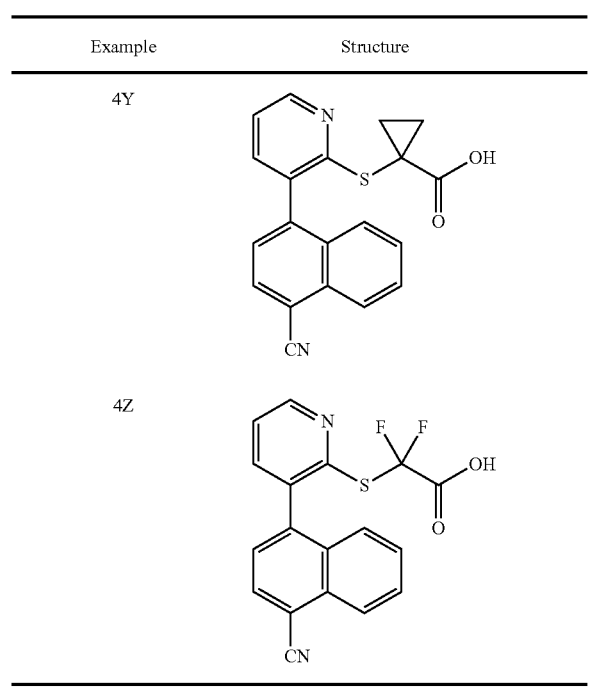 |
| 4Z | 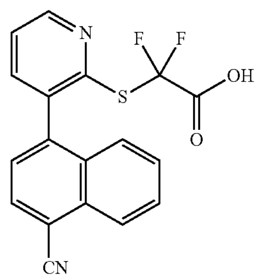 [SMILES: N#Cc1ccc(-c2cccnc2SC(F)(F)C(=O)O)c2ccccc12] |
Example 5
Preparation of Compounds of Formula (I-E)
Compounds of formula (I-E) may be prepared according to the general schemes shown below:
Scheme I-E-a:
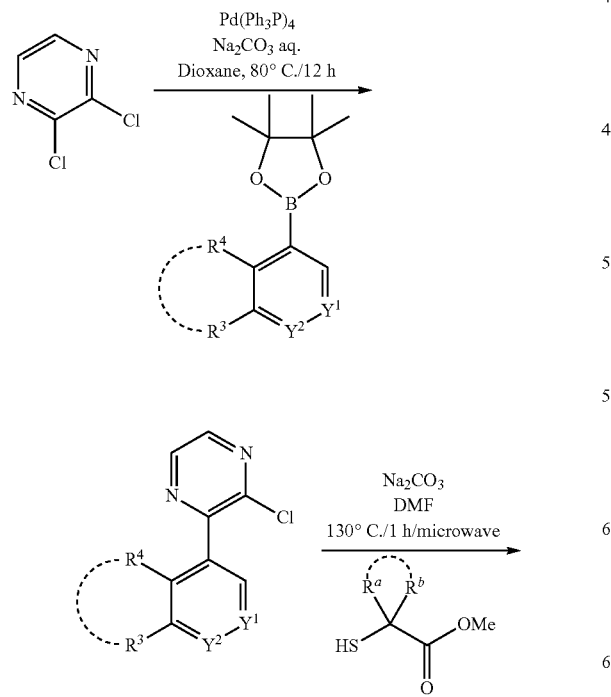
Scheme I-E-b:
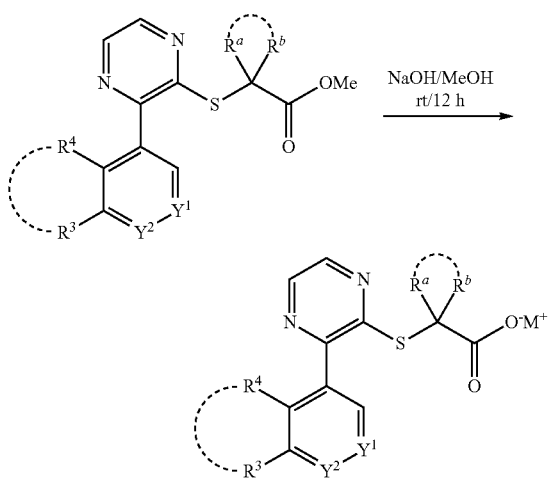
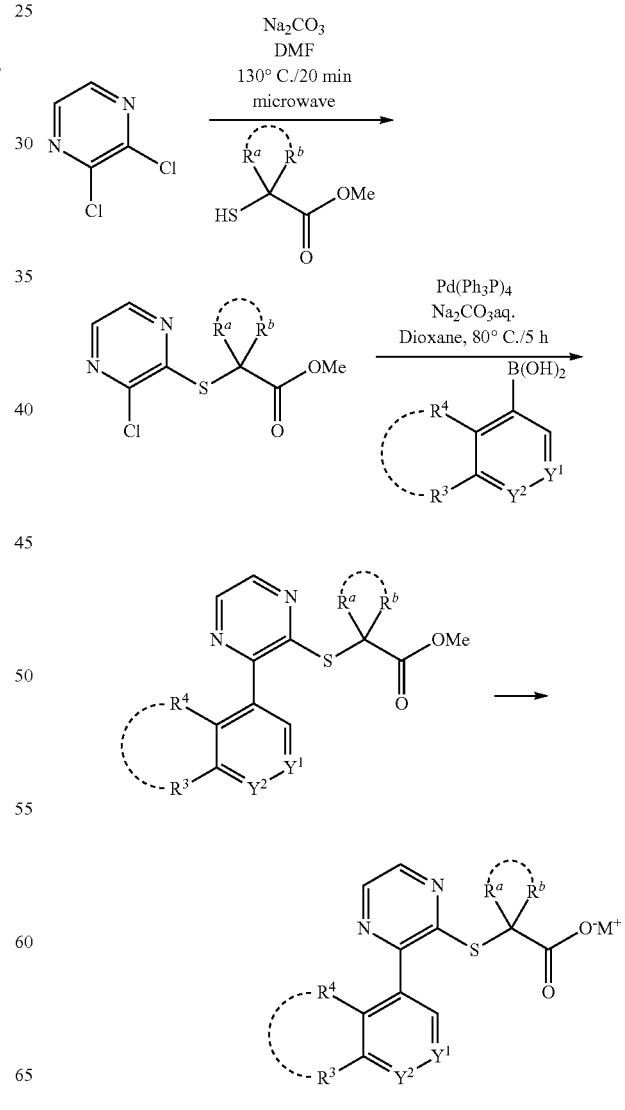

Example 5A

2-(3-(4-Cyanonaphthalen-1-yl)pyrazin-2-ylthio)acetic acid

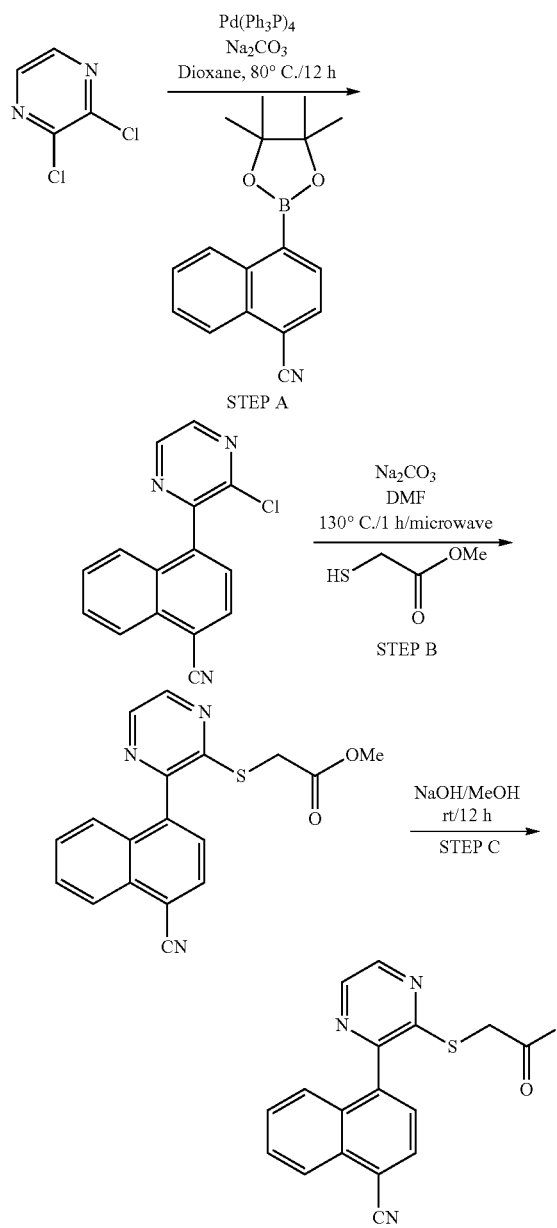

Step A: 4-(3-Chloropyrazin-2-yl)-1-naphthonitrile

A mixture of 2,3-dichloropyrazine (2.98 g, 2 mmol), 4-(4,4,5,5-tetramethyl-1,3,2-dioxaborolan-2-yl)-1-naphthonitrile (0.558 mmol, 2 mmol) palladium tetrakis triphenylphoshine (0.069 g, 0.06 mmol) and aqueous sodium carbonate solution (2M, 3 mL, 6 mmol) in dioxane (7 mL) was heated to 80° C. for 12 hours. The reaction mixture cooled to room temperature, washed with water, extracted with ethyl acetate and purified by chromatography to yield 4-(3-chloropyrazin-2-yl)-1-naphthonitrile (0.36 g, 68%).

Step B: Methyl 2-(3-(4-cyanonaphthalen-1-yl)pyrazin-2-ylthio)acetate

A mixture of 4-(3-chloropyrazin-2-yl)-1-naphthonitrile (0.16 g, 0.6 mmol), methyl thioglycolate (0.127 g, 1.2 mmol) and sodium carbonate (0.082 g, 0.78 mmol) in DMF (1 mL) was heated under microwave irradiation to 130° C. for 1 hour. The mixture was washed with water, extracted with ethyl acetate and purified by chromatography to yield methyl 2-(3-(4-cyanonaphthalen-1-yl)pyrazin-2-ylthio)acetate (0.127 g, 63%).

Step C: 2-(3-(4-Cyanonaphthalen-1-yl)pyrazin-2-ylthio)acetic acid

A mixture of methyl 2-(3-(4-cyanonaphthalen-1-yl)pyrazin-2-ylthio)acetate (0.125 g, 0.37 mmol), aqueous sodium hydroxide solution (1M, 0.5 mL) and methanol (1 mL) was stirred at room temperature for 12 hours. Methanol was removed and the mixture washed with water and extracted with ethyl acetate. The organic layer was dried over $MgSO_4$ and concentrated to dryness. Solid residue was recrystallized from ethyl acetate and hexanes to yield 2-(3-(4-cyanonaphthalen-1-yl)pyrazin-2-ylthio)acetic acid (0.102 g, 86%).

$^1$H NMR (400 MHz, DMSO-$d_6$, 25° C.) 12.60 (bs, OH), 8.70 (d, J=2.4 Hz, 1H), 8.60 (d, J=2.4 Hz, 1H), 8.36 (d, J=7.6 Hz, 1H), 8.29 (d, J=8.4 Hz, 1H), 7.90 (dd, J=7.6, 7.6 Hz, 1H), 7.80 (d, J=7.6 Hz, 1H), 7.71 (dd, J=7.6, 7.6 Hz, 1H), 7.56 (d, J=8.4 Hz, 1H), 3.95 (s, 2H).

MS (m/z), M+1=322.08

Examples 5B-5Z

The compounds in the table below are prepared according to the procedures described in example 5A.

| Example | Structure |
|---|---|
| 5A | (pyrazine-SC(CH3)2COOH with phenyl substituent) |
| 5B | (pyrazine-SC(CH3)2COOH with 3,4-dichlorophenyl substituent) |

-continued

| Example | Structure |
|---|---|
| 5C | 3-(4-ethylphenyl)pyrazin-2-yl thio-2-methylpropanoic acid |
| 5D | 3-(1H-benzimidazol-4-yl)pyrazin-2-yl thio-2-methylpropanoic acid |
| 5E | 3-(naphthalen-1-yl)pyrazin-2-yl thio-2-methylpropanoic acid |
| 5F | 3-(naphthalen-2-yl)pyrazin-2-yl thio-2-methylpropanoic acid |
| 5G | 3-(4-methylnaphthalen-1-yl)pyrazin-2-yl thio-2-methylpropanoic acid |
| 5H | 3-(1H-indol-4-yl)pyrazin-2-yl thio-2-methylpropanoic acid |

-continued

| Example | Structure |
|---|---|
| 5I | 3-(pyridin-2-yl)pyrazin-2-yl thio-2-methylpropanoic acid |
| 5J | 3-(pyridin-3-yl)pyrazin-2-yl thio-2-methylpropanoic acid |
| 5K | 3-(pyridin-4-yl)pyrazin-2-yl thio-2-methylpropanoic acid |
| 5L | 3-(benzothiazol-4-yl)pyrazin-2-yl thio-2-methylpropanoic acid |
| 5M | 3-(6-methoxypyridin-3-yl)pyrazin-2-yl thio-2-methylpropanoic acid |
| 5N | 3-(pyrimidin-5-yl)pyrazin-2-yl thio-2-methylpropanoic acid |

| Example | Structure |
|---------|-----------|
| 5O | 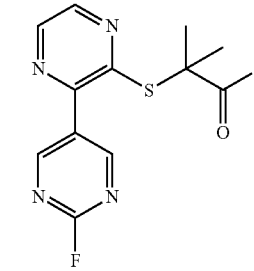 |
| 5Q | 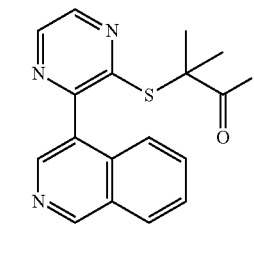 |
| 5R | 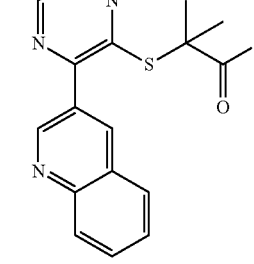 |
| 5S | 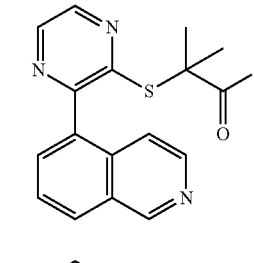 |
| 5T | 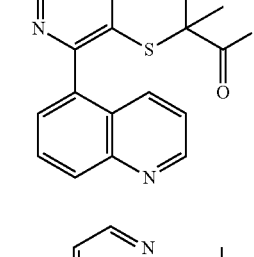 |
| 5U | 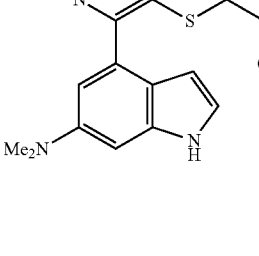 |
| Example | Structure |
|---------|-----------|
| 5V | |
| 5W | |
| 5X | |
| 5Y | |
| 5Z | |

Example 6
Preparation of Compounds of Formula (I-F)
Compounds of formula (I-F) may be prepared according to the general schemes shown below:
Scheme I-F-a:
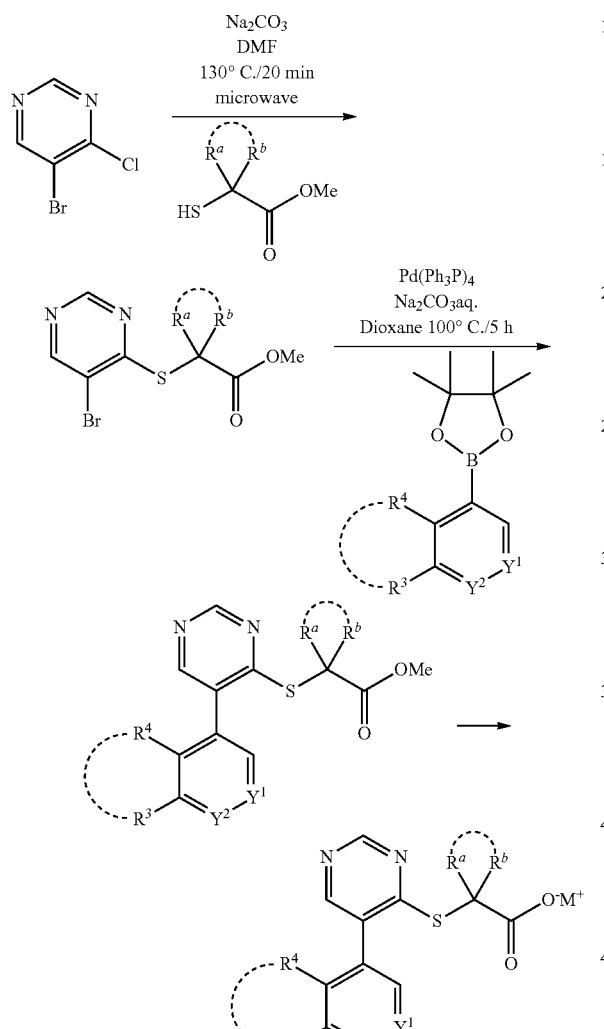
Scheme I-F-b:
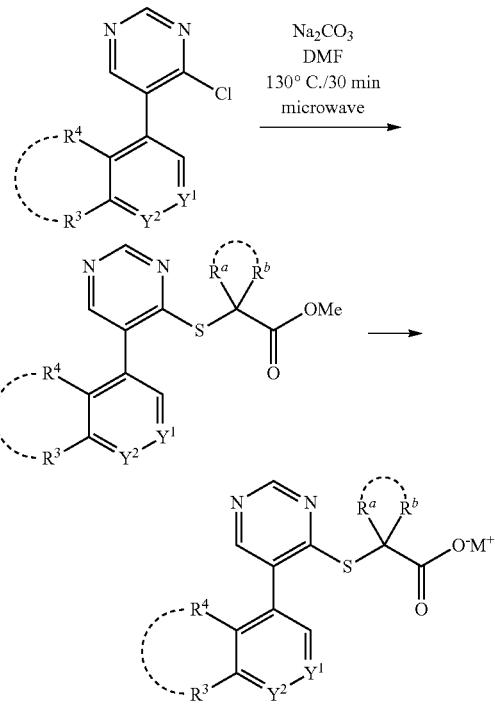
Example 6A
2-(5-(4-Cyanonaphthalen-1-yl)pyrimidin-4-ylthio)acetic acid
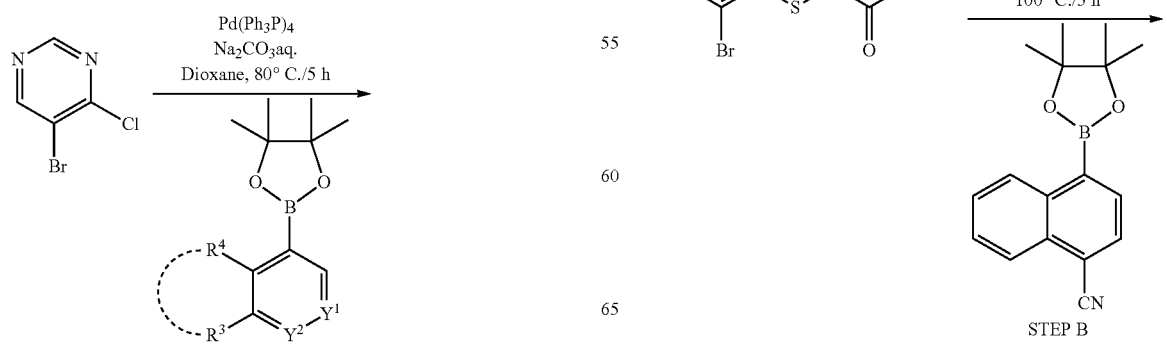

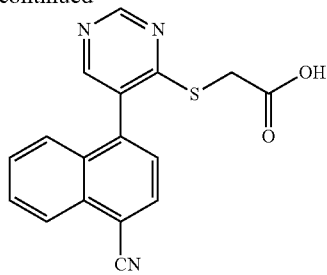

Step A: methyl 2-(5-bromopyrimidin-4-ylthio)acetate

A mixture of 4-chloro-5-bromopyrimidine (0.193 g, 1.0 mmol), methyl 2-mercaptoacetate (0.116 g, 1.1 mmol) and sodium carbonate (0.159 g, 1.5 mmol) in DMF (0.7 mL) was heated under microwave irradiation to 150° C. for 20 minutes. The mixture was washed with water, extracted with ethyl acetate and purified by chromatography to yield methyl 2-(5-bromopyrimidin-4-ylthio)acetate (0.22 g, 84%).

Step B: 2-(5-(4-cyanonaphthalen-1-yl)pyrimidin-4-ylthio)acetic acid

A mixture of methyl 2-(5-bromopyrimidin-4-ylthio)acetate (220 mg, 0.84 mmol), 4-(4,4,5,5-tetramethyl-1,3,2-dioxaborolan-2-yl)-1-naphthonitrile (237 mg, 0.85 mmol) palladium tetrakis triphenylphoshine (46 mg, 0.04 mmol) and aqueous sodium carbonate solution (2M, 1.5 mL, 3 mmol) in dioxane (3 mL) was heated to 100° C. for 5 hours. The reaction mixture was allowed to cool to room temperature and aqueous sodium hydroxide solution added (1M, 30 mL). The mixture was washed with ethyl acetate (2×20 mL), and the aqueous layer acidified to pH 4 resulting in formation of a precipitate which was isolated by filtration and dried under vacuum to yield 2-(5-(4-cyanonaphthalen-1-yl)pyrimidin-4-ylthio)acetic acid (143 mg, 53%).

$^1$H NMR (400 MHz, DMSO-$d_6$) 12.80 (bs, OH), 9.15 (s, 1H), 8.56 (s, 1H), 8.35 (d, J=7.2 Hz, 1H), 8.29 (d, J=8.4 Hz, 1H), 7.91 (dd, J=7.6, 7.6 Hz, 1H), 7.75 (dd, J=7.6, 7.6 Hz, 1H), 7.71 (d, J=7.6, Hz, 1H), 7.61 (d, J=8.4 Hz, 1H), 3.99 (s, 2H).

MS (m/z), M+1, 322.08

Example 6B

2-(5-(4-cyanonaphthalen-1-yl)pyrimidin-4-ylthio)-2-methylpropanoic acid 2-(5-(4-cyanonaphthalen-1-yl)pyrimidin-4-ylthio)-2-methylpropanoic acid was prepared according to the procedures described in example 6A, using methyl 2-mercapto-2-methylpropanoate in place of methyl 2-mercaptoacetate, in step A $^1$H NMR (400 MHz, DMSO-$d_6$) 12.70 (bs, OH), 9.07 (s, 1H), 8.53 (s, 1H), 8.33 (d, J=7.6 Hz, 1H), 8.27 (d, J=7.6 Hz, 1H), 7.91 (dd, J=7.6, 7.6 Hz, 1H), 7.75 (dd, J=7.6, 7.6 Hz, 1H), 7.71 (d, J=7.6, Hz, 1H), 7.56 (d, J=8.0 Hz, 1H), 3.99 (s, 2H).

MS (m/z), M+1, 350.08.

Examples 6C-6F

| Example | Structure | $^1$H NMR (400 MHz, DMSO-$d_6$) δ ppm | MS (m/z) M + 1 |
|---|---|---|---|
| 6C | 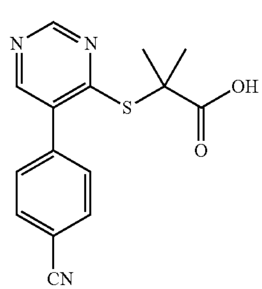 [SMILES: CC(C)(Sc1ncncc1-c1ccc(C#N)cc1)C(=O)O] | $^1$H NMR (400 MHz, CDCl$_3$, 25° C.) 8.94 (s, 1H), 8.39 (s, 1H), 7.82 (d, J = 8.4 Hz, 2H), 7.61 (d, J = 8.4 Hz, 2H), 1.75 (s, 6H). | 299.94 |

-continued

| Example | Structure | ¹H NMR (400 MHz, DMSO-d₆) δ ppm | MS (m/z) M + 1 |
|---|---|---|---|
| 6D | 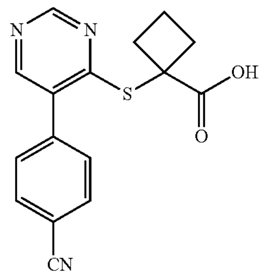 [SMILES: N#Cc1ccc(-c2cncnc2SC2(C(=O)O)CCC2)cc1] | ¹H NMR (400 MHz, CDCl₃, 25° C.) 11.4 (bs, COOH), 8.94 (s, 1H), 8.41 (s, 1H), 7.83 (d, J = 8.4 Hz, 2H), 7.61 (d, J = 8.4 Hz, 2H), 2.96-3.10 (m, 2H), 2.11-2.30 (m, 6H). | 311.95 |
| 6E | 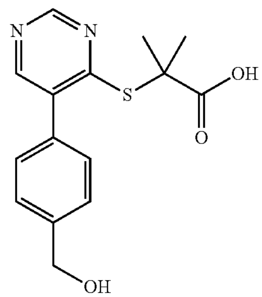 [SMILES: CC(C)(Sc1ncncc1-c1ccc(CO)cc1)C(=O)O] | ¹H NMR (400 MHz, DMSO-d₆, 25° C.) 12.58 (bs, COOH), 8.89 (s, 1H), 8.42 (s, 1H), 7.44-7.50 (m, 4H), 5.32 (t, J = 6.0 Hz, OH), 4.59 (d, J = 6.0 Hz, 2H), 1.62 (s, 6H). | 305.00 |
| 6F | 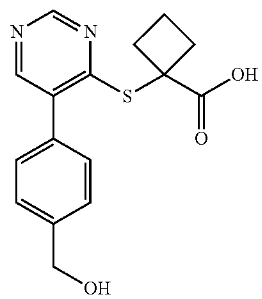 [SMILES: O=C(O)C1(Sc2ncncc2-c2ccc(CO)cc2)CCC1] | ¹H NMR (400 MHz, DMSO-d₆, 25° C.) 12.7 (bs, COOH), 8.86 (s, 1H), 8.42 (s, 1H), 7.5 (s, 4H), 5.34 (t, J = 6.0 Hz, OH), 4.60 (d, J = 6.0 Hz, 2H), 2.74-3.85 (m, 2H), 2.06-2.30 (m, 6H). | 317.01 |

Examples 6G-5Z

The compounds in the table below are prepared according to the procedures described in example 6A.

| Example | Structure |
|---|---|
| 6G | |
| 6H | 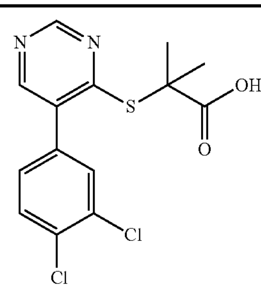 |
| 6I | 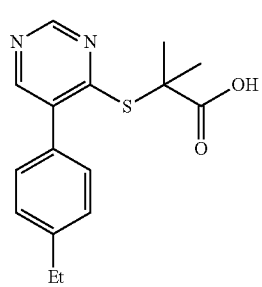 [SMILES: CCc1ccc(-c2cncnc2SC(C)(C)C(=O)O)cc1] |

-continued
| Example | Structure |
|---|---|
| 6G | 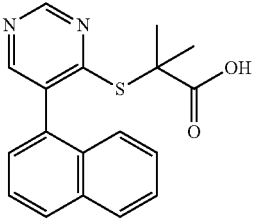 [SMILES: CC(C)(Sc1ncncc1-c1cccc2ccccc12)C(=O)O] |
| 6K | 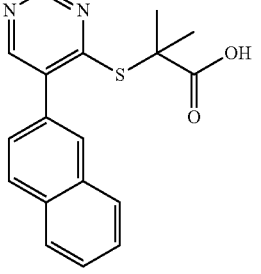 |
| 6L | 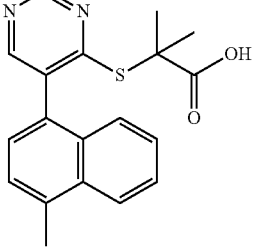 |
| 6M | 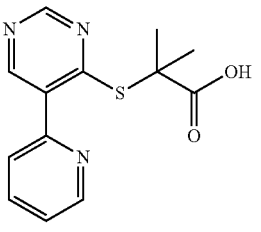 [SMILES: CC(C)(Sc1ncncc1-c1ccccn1)C(=O)O] |
| 6N | 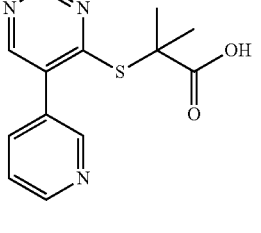 |
| 6O | 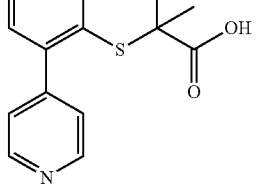 |
-continued
| Example | Structure |
|---|---|
| 6P | 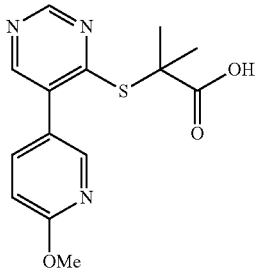 [SMILES: COc1ccc(-c2cncnc2SC(C)(C)C(=O)O)cn1] |
| 6Q | 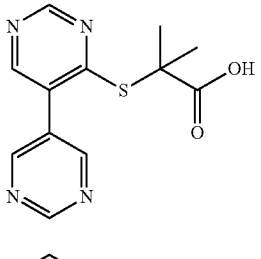 |
| 6R | 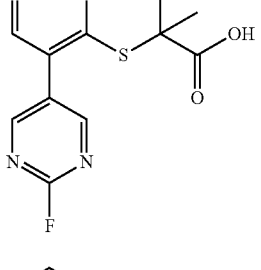 |
| 6T | 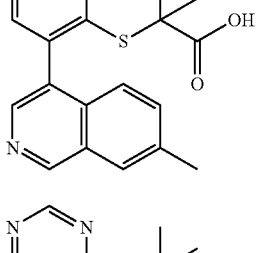 |
| 6U | 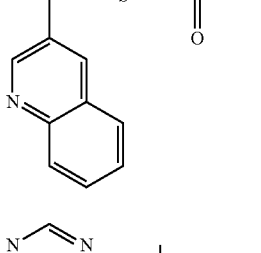 |
| 6V | 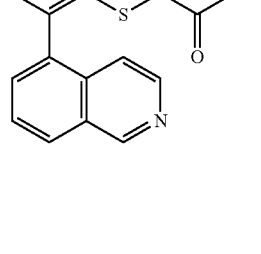 |

155
-continued
| Example | Structure |
|---|---|
| 6W | 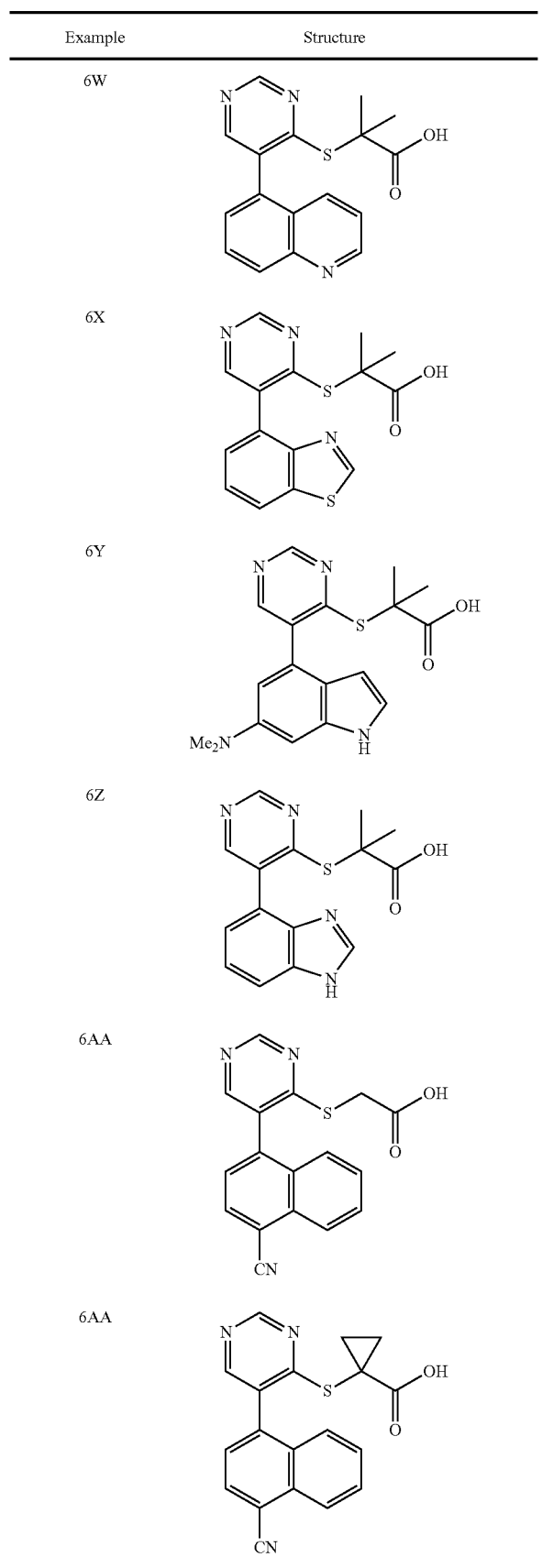 |
| 6X | 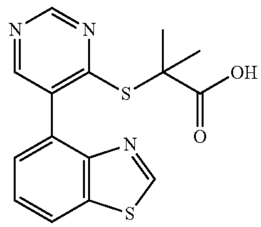 [SMILES: CC(C)(Sc1ncncc1-c1cccc2scnc12)C(=O)O] |
| 6Y | 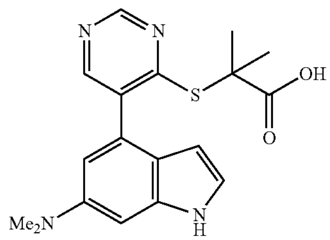 [SMILES: CN(C)c1cc(-c2cncnc2SC(C)(C)C(=O)O)c2cc[nH]c2c1] |
| 6Z | 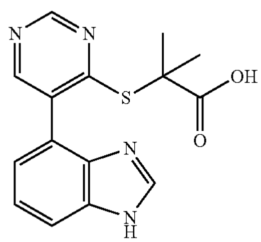 [SMILES: CC(C)(Sc1ncncc1-c1cccc2[nH]cnc12)C(=O)O] |
| 6AA | |
| 6AA | |
156
-continued
| Example | Structure |
|---|---|
| 6BB | 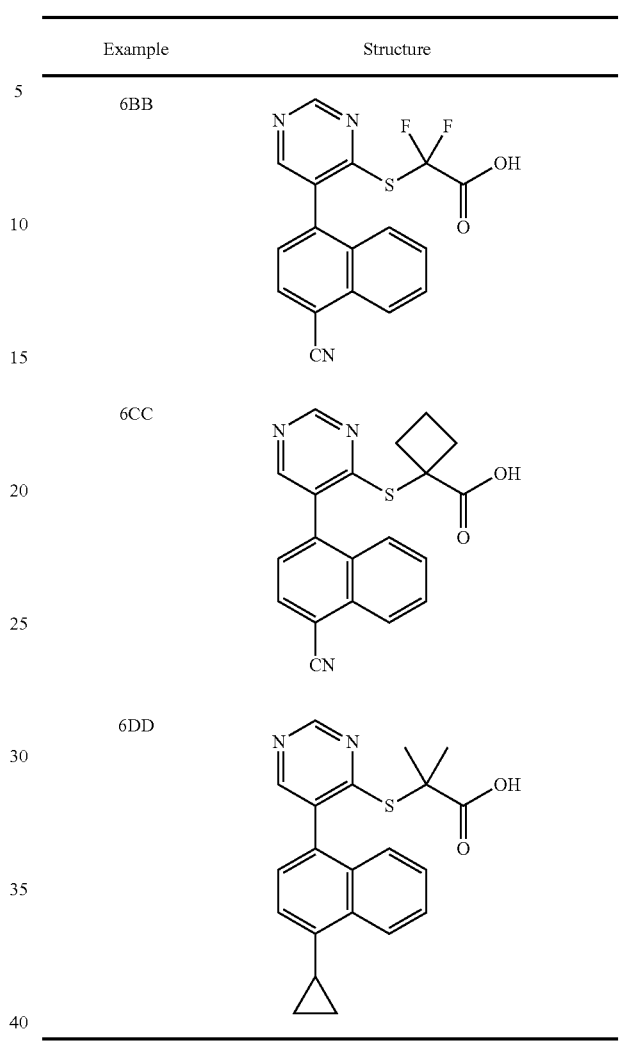 |
| 6CC | 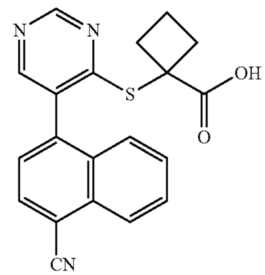 [SMILES: N#Cc1ccc(-c2cncnc2SC2(C(=O)O)CCC2)c2ccccc12] |
| 6DD | 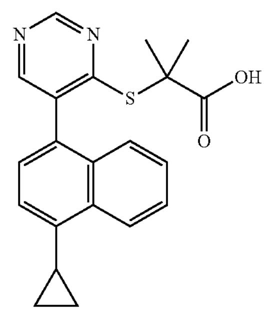 [SMILES: CC(C)(Sc1ncncc1-c1ccc(C2CC2)c2ccccc12)C(=O)O] |
Example 7
Preparation of Compounds of Formula (I-G)
Compounds of formula (I-G) may be prepared according to the general schemes shown below:
Scheme I-G-a:
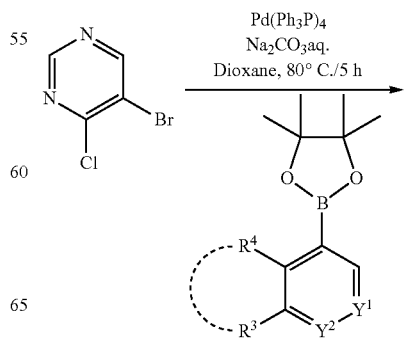

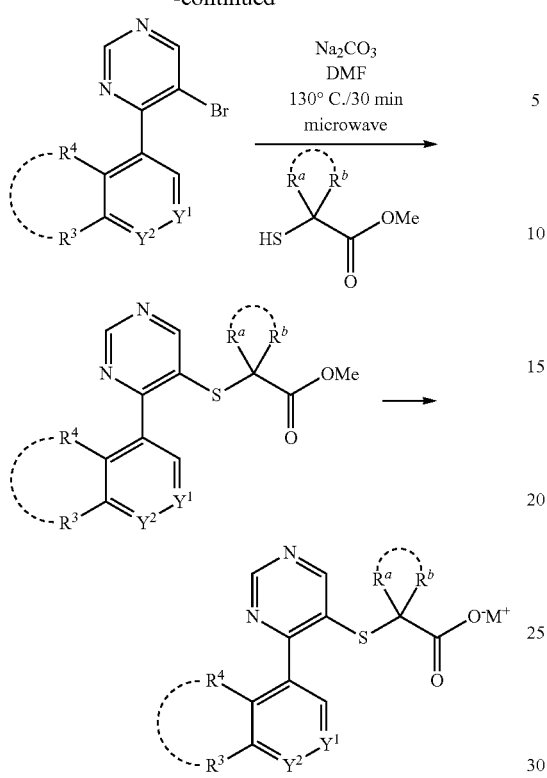
Scheme I-G-b:
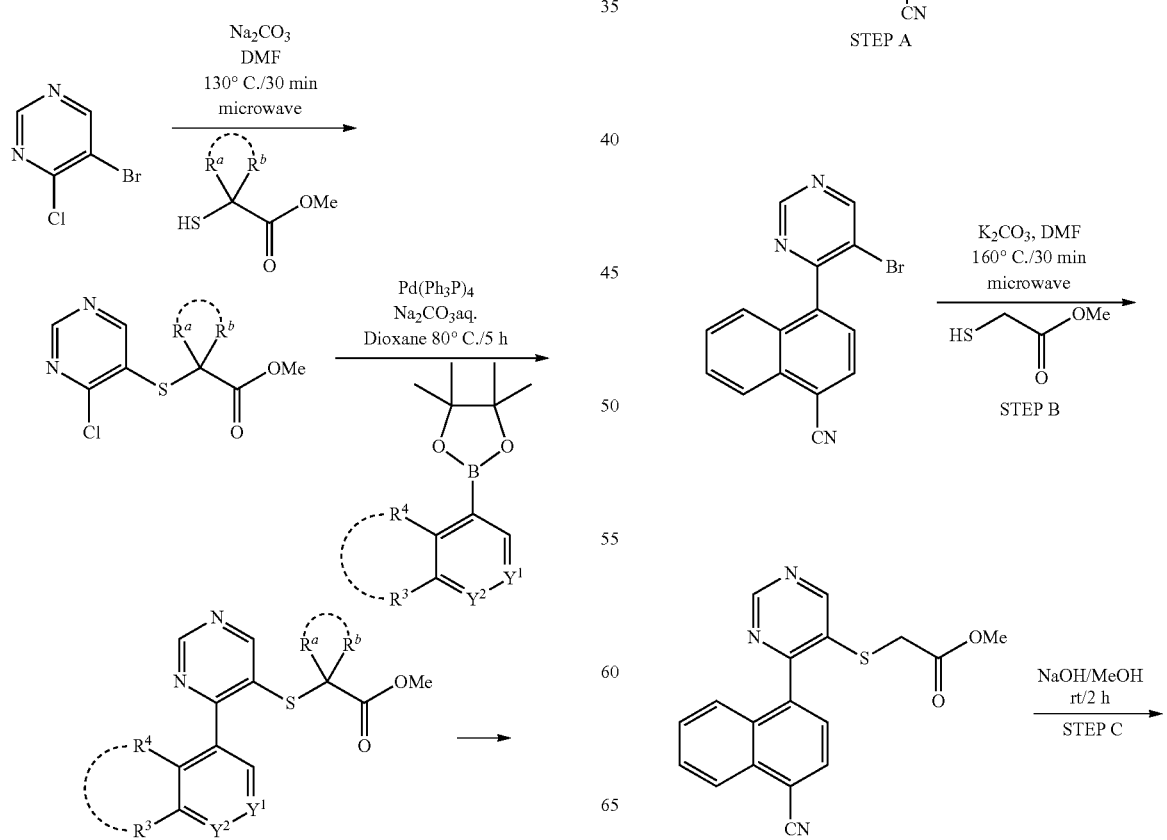
Example 7A
2-(4-(4-Cyanonaphthalen-1-yl)pyrimidin-5-ylthio)acetic acid
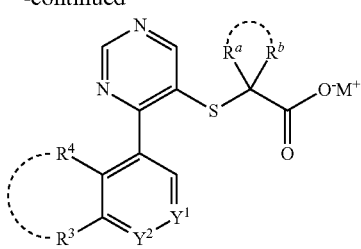
STEP A
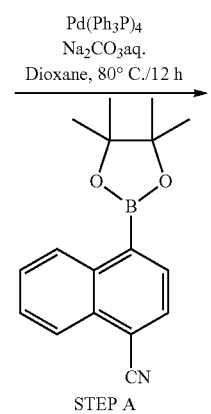
STEP B
STEP C -continued

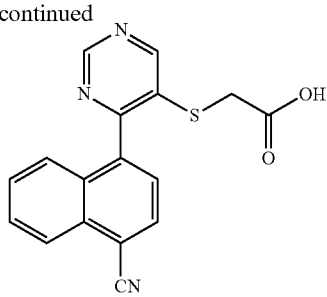

Step A: 4-(5-Bromopyrimidin-4-yl)-1-naphthonitrile

A mixture of 4-chloro-5-bromopyrimidine (193 mg, 1 mmol), 4-(4,4,5,5-tetramethyl-1,3,2-dioxaborolan-2-yl)-1-naphthonitrile (279 mg, 1 mmol) palladium tetrakis triphenylphoshine (0.023 g, 0.02 mmol) and aqueous sodium carbonate solution (2M, 1.5 mL, 3 mmol) in dioxane (3 mL) was heated to 80° C. for 12 hours. The reaction mixture cooled to room temperature, washed with water, extracted with ethyl acetate and purified by chromatography to yield 4-(5-bromopyrimidin-4-yl)-1-naphthonitrile (214 mg, 69%).

Step B: Methyl 2-(4-(4-cyanonaphthalen-1-yl)pyrimidin-5-ylthio)acetate

A mixture of 4-(5-bromopyrimidin-4-yl)-1-naphthonitrile (45 mg, 0.14 mmol), methyl thioglycolate (74 mg, 0.7 mmol) and potassium carbonate (27 mg, 0.2 mmol) in DMF (0.6 mL) was heated under microwave irradiation to 160° C. for 0.5 hour. The mixture was washed with water, extracted with ethyl acetate and purified by chromatography to yield methyl 2-(4-(4-cyanonaphthalen-1-yl)pyrimidin-5-ylthio)acetate (22 mg, 47%).

Step C: 2-(4-(4-Cyanonaphthalen-1-yl)pyrimidin-5-ylthio)acetic acid

A mixture of methyl 2-(4-(4-cyanonaphthalen-1-yl)pyrimidin-5-ylthio)acetate (22 mg, 0.065 mmol), aqueous sodium hydroxide solution (1M, 0.5 mL) and methanol (1 mL) was stirred at room temperature for 2 hours. Methanol was removed and aqueous sodium hydroxide solution (1M, 1 mL) and ethyl acetate (3 mL) were added. The aqueous layer was removed, acidified and extracted with ethyl acetate. The second organic layer was concentrated to dryness to yield 2-(4-(4-cyanonaphthalen-1-yl)pyrimidin-5-ylthio)acetic acid (19 mg, 91%).

$^1$H NMR (400 MHz, CDCl$_3$, 25° C.) 9.26 (s, 1H), 9.03 (s, 1H), 8.71 (bs, 1H), 8.39 (d, J=8.0 Hz, 1H), 8.50 (d, J=8.4 Hz, 1H), 7.79 (dd, J=7.2, 7.2 Hz, 1H), 7.55-7.66 (m, 2H), 7.61 (d, J=8.4 Hz, 1H), 3.99 (s, 2H). MS (m/z), M+1=322.08

Examples 7B-7Z

The compounds in the table below are prepared according to the procedures described in example 7A.

| Example | Structure |
|---|---|
| 7B | 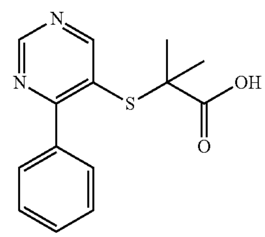 [SMILES: CC(C)(Sc1cncnc1-c1ccccc1)C(=O)O] |
| 7C | 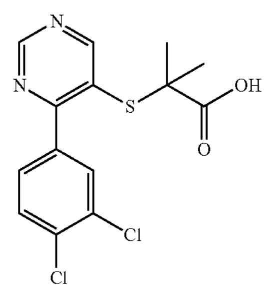 [SMILES: CC(C)(Sc1cncnc1-c1ccc(Cl)c(Cl)c1)C(=O)O] |
| 7D | 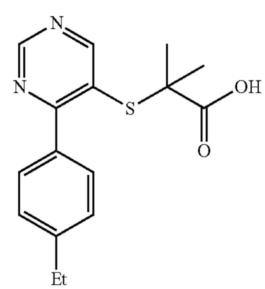 [SMILES: CCc1ccc(-c2ncncc2SC(C)(C)C(=O)O)cc1] |
| 7E | 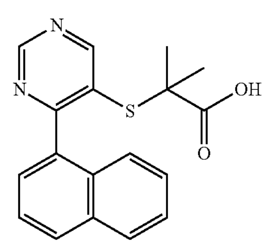 [SMILES: CC(C)(Sc1cncnc1-c1cccc2ccccc12)C(=O)O] |
| 7F | 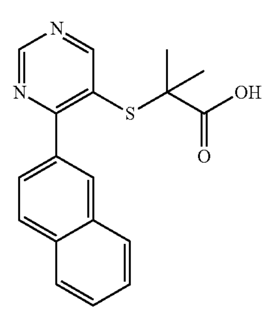 [SMILES: CC(C)(Sc1cncnc1-c1ccc2ccccc2c1)C(=O)O] |

| Example | Structure |
|---|---|
| 7G | 4-(pyridin-2-yl)pyrimidin-5-yl sulfanyl 2-methylpropanoic acid |
| 7H | 4-(pyrimidin-3-yl... ) — 4-(pyridin-3-yl)pyrimidin-5-yl derivative |
| 7I | 4-(pyridin-4-yl)pyrimidin-5-yl derivative |
| 7J | 4-(6-methoxypyridin-3-yl)pyrimidin-5-yl derivative |
| 7K | 4-(pyrimidin-5-yl)pyrimidin-5-yl derivative |
| 7L | 4-(2-fluoropyrimidin-5-yl)pyrimidin-5-yl derivative |

| Example | Structure |
|---|---|
| 7N | 4-(7-methylisoquinolin-5-yl)pyrimidin-5-yl derivative |
| 7O | 4-(quinolin-3-yl)pyrimidin-5-yl derivative |
| 7P | 4-(isoquinolin-5-yl)pyrimidin-5-yl derivative |
| 7Q | 4-(quinolin-5-yl)pyrimidin-5-yl derivative |
| 7R | 4-(cinnolin-8-yl)pyrimidin-5-yl derivative |
| 7S | 4-(6-(dimethylamino)-1H-indol-4-yl)pyrimidin-5-yl derivative |

| Example | Structure |
|---|---|
| 7T | 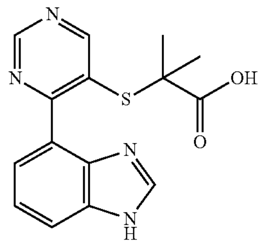 [SMILES: CC(C)(Sc1cncnc1-c1cccc2[nH]cnc12)C(=O)O] |
| 7U | 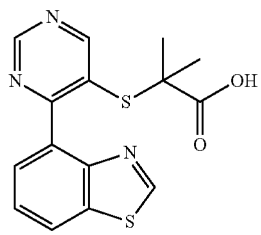 [SMILES: CC(C)(Sc1cncnc1-c1cccc2scnc12)C(=O)O] |
| 7V | 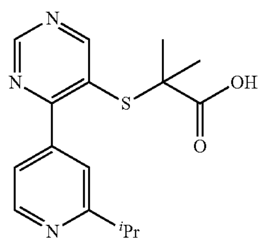 [SMILES: CC(C)c1cc(-c2ncncc2SC(C)(C)C(=O)O)ccn1] |
| 7W | 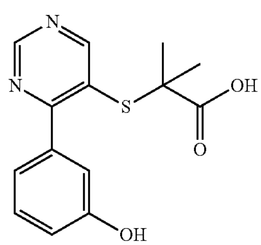 [SMILES: CC(C)(Sc1cncnc1-c1cccc(O)c1)C(=O)O] |
| 7X | 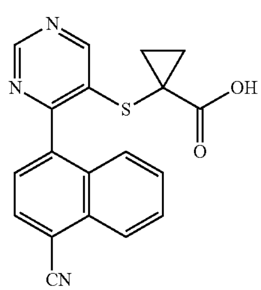 [SMILES: N#Cc1ccc(-c2ncncc2SC2(C(=O)O)CC2)c2ccccc12] |
| 7Y | 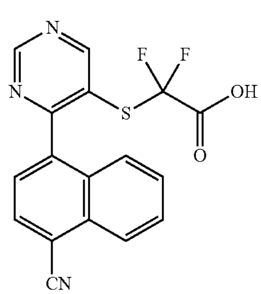 [SMILES: N#Cc1ccc(-c2ncncc2SC(F)(F)C(=O)O)c2ccccc12] |

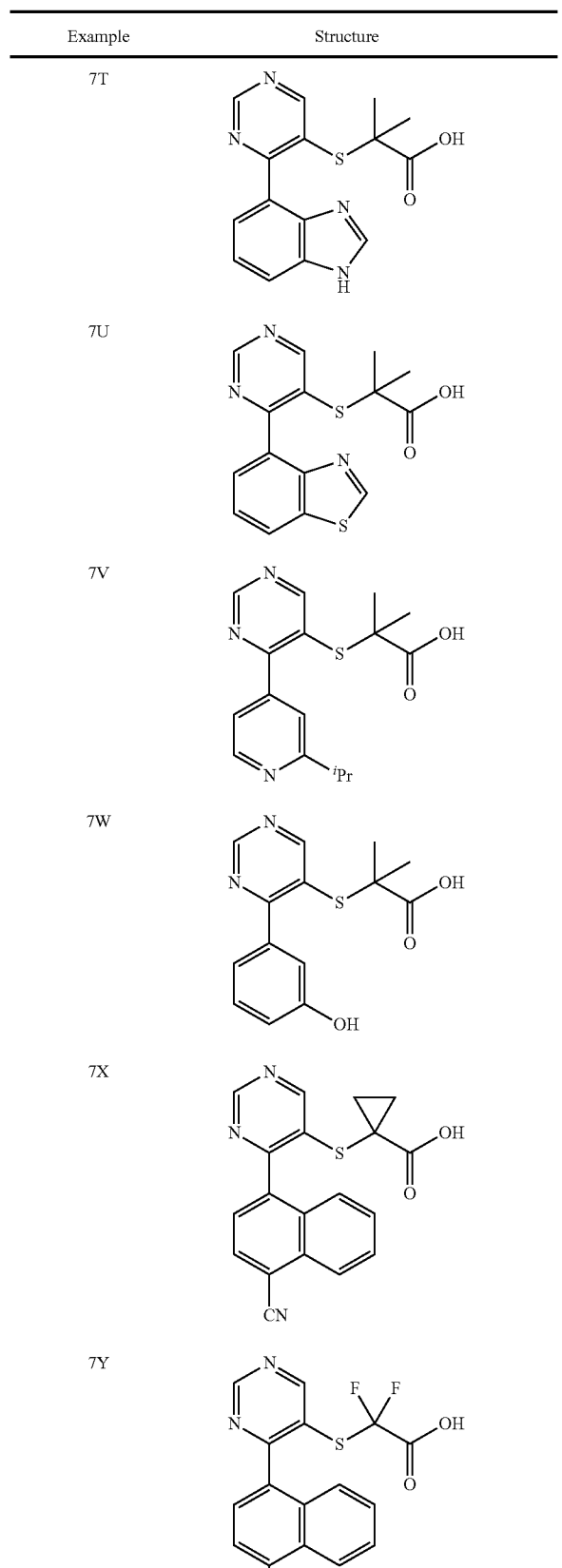

| Example | Structure |
|---|---|
| 7Z | 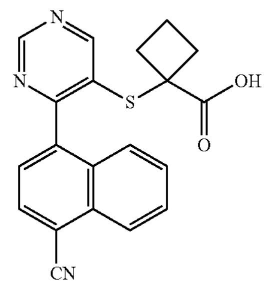 [SMILES: N#Cc1ccc(-c2ncncc2SC2(C(=O)O)CCC2)c2ccccc12] |

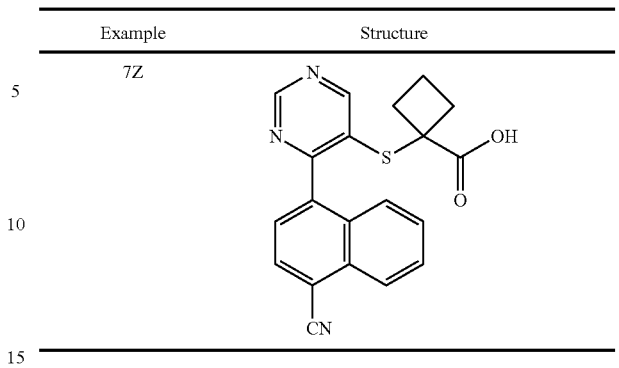

II. Biological Evaluation

Example 8

Evaluation with URAT1-Model Assay

HEK293 human embryonic kidney cells (ATCC# CRL-1573) were propagated in EMEM tissue culture medium as described by ATCC in an atmosphere of 5% $CO_2$ and 95% air. Transfections of HEK293 cells with a model URAT1 construct was performed using L2000 transfection reagent (Invitrogen) as described by the manufacturer. After 24 h the transfected cells were split into 10 cm tissue culture plates and grown for 1 day after which the medium was replaced with fresh growth medium containing G418 (Gibco) at 0.5 mg/ml final concentration. Drug-resistant colonies were selected after approximately 8 days and then tested for $^{14}$C-uric acid transport activity. The HEK293/URAT1-model cells are plated on Poly-D-Lysine Coated 96-well Plates at a density of 125,000 cells per well.

Cells were grown overnight (20-26 hours) at 37° C. in an incubator. Plates were allowed to come to room temperature and media was washed out with one wash of 250 μl of Wash Buffer (125 mM Na Gluconate, 10 mM Hepes ph 7.3). Compound or vehicle is added in assay buffer with $^{14}$C-uric acid for a final concentration of 12504 Uric Acid with a specific activity of 54 mCi/mmol. Assay Buffer is 125 mM Sodium Gluconate, 4.8 mM Potassium Gluconate, 1.2 mM Potassium phosphate, monobasic, 1.2 mM magnesium sulfate, 1.3 mM Ca Gluconate, 5.6 mM Glucose, 25 mM HEPES, pH 7.3. Plates were incubated at room temperature for 10 minutes then washed 3 times with 50 μl Wash Buffer and 3 times with 250 μl Wash Buffer. Microscint 20 Scintillation Fluid was added and plates were incubated overnight at room temperature to equilibrate. Plates are then read on the TopCount Plate Reader and an EC50 value generated. (See Enomoto et al, Nature, 2002, 417, 447-451 and Anzai et al, J. Biol. Chem., 2004, 279, 45942-45950.)

Compounds as described herein were tested according to the protocol described above against URAT-1 model; the results are shown in the table below wherein:

A represents an $EC_{50}$ value in the range of ≦10 μM to >0.5 μM;

B represents an $EC_{50}$ value in the range of ≦0.5 μM to >0.05 μM; and

C represents an $EC_{50}$ value in the range of ≦0.05 μM to >0.001 μM.

| Example | Structure | URAT1 EC50 Activity Ranking |
|---|---|---|
| 1A | 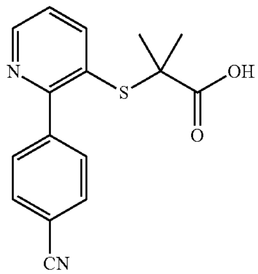 [SMILES: CC(C)(Sc1cccnc1-c1ccc(C#N)cc1)C(=O)O] | B |
| 2A | 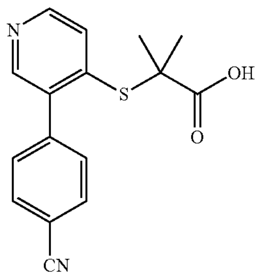 [SMILES: CC(C)(Sc1ccncc1-c1ccc(C#N)cc1)C(=O)O] | C |
| 4C | 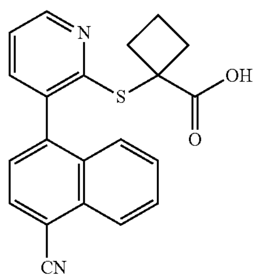 [SMILES: N#Cc1ccc(-c2cccnc2SC2(C(=O)O)CCC2)c2ccccc12] | B |
| 6B | 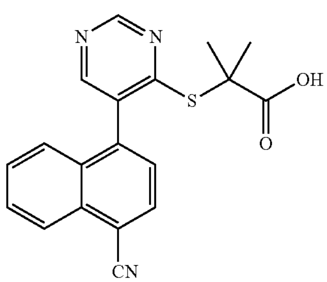 [SMILES: CC(C)(Sc1ncncc1-c1ccc(C#N)c2ccccc12)C(=O)O] | A |
| 2H | 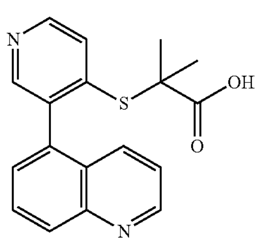 [SMILES: CC(C)(Sc1ccncc1-c1cccc2ncccc12)C(=O)O] | B |
| 2I | | A |
| 2J | | C |
| 2K | | B |
| 2M | | A |
| 2N | | B |

| Example | Structure | URAT1 EC50 Activity Ranking |
|---|---|---|
| 2O | 3-(4-chlorophenyl)pyridin-4-yl S-C(CH3)2-COOH | C |
| 2P | 3-(4-chlorophenyl)pyridin-4-yl S-C(CH3)2-COOH | C |
| 2Q | 3-(4-methylthiophenyl)pyridin-4-yl S-C(CH3)2-COOH | B |
| 2R | 3-phenylpyridin-4-yl S-C(CH3)2-COOH | A |
| 2S | 3-(3,4-dichlorophenyl)pyridin-4-yl S-C(CH3)2-COOH | B |
| 2T | 3-(6-methoxypyridin-3-yl)pyridin-4-yl S-C(CH3)2-COOH | B |
| 2U | 3-(isoquinolin-4-yl)pyridin-4-yl S-C(CH3)2-COOH | B |
| 2V | 3-(6-methoxynaphthalen-2-yl)pyridin-4-yl S-C(CH3)2-COOH | A |
| 2X | 3-(4-fluoronaphthalen-1-yl)pyridin-4-yl S-C(CH3)2-COOH | C |
| 2Y | 3-(6-ethoxynaphthalen-2-yl)pyridin-4-yl S-C(CH3)2-COOH | A |

-continued

| Example | Structure | URAT1 EC50 Activity Ranking |
|---|---|---|
| 2BB | pyridine-S-C(CH3)2-COOH with 4-methylnaphthalen-1-yl | B |
| 2CC | pyridine-S-C(CH3)2-COOH with 4-(aminosulfonyl)phenyl | B |
| 2DD | pyridine-S-C(CH3)2-COOH with naphthalen-1-yl | B |
| 2EE | pyridine-S-C(CH3)2-COOH with 4-chloro-3-(trifluoromethyl)phenyl | B |
| 2FF | pyridine-S-CF2-COOH with 4-cyanonaphthalen-1-yl | A |

-continued

| Example | Structure | URAT1 EC50 Activity Ranking |
|---|---|---|
| 2GG | pyridine-S-C(CH3)2-COOH with 4-fluorophenyl | B |
| 2HH | pyridine-S-C(CH3)2-COOH with 2-methoxypyrimidin-5-yl | A |
| 2II | pyridine-S-C(CH3)2-COOH with quinolin-4-yl | B |
| 2JJ | pyridine-S-C(CH3)2-COOH with 4-(hydroxymethyl)phenyl | C |
| 2KK | pyridine-S-C(CH3)2-COOH with 4-carbamoylphenyl | B |

-continued

| Example | Structure | URAT1 EC50 Activity Ranking |
|---|---|---|
| 2LL | 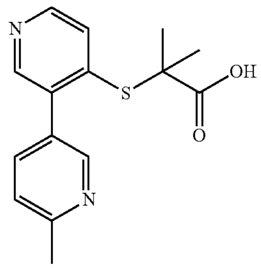 [SMILES: Cc1ccc(-c2cnccc2SC(C)(C)C(=O)O)cn1] | A |
| 2MM | 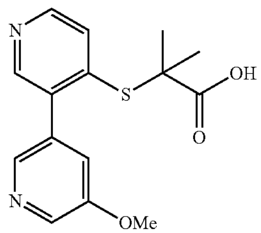 [SMILES: COc1cncc(-c2cnccc2SC(C)(C)C(=O)O)c1] | B |
| 2NN | 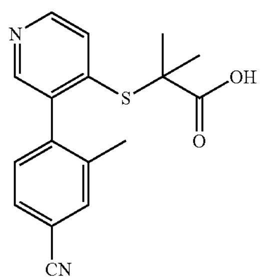 [SMILES: Cc1cc(C#N)ccc1-c1cnccc1SC(C)(C)C(=O)O] | C |
| 2PP | 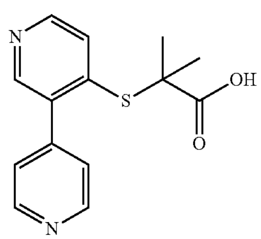 [SMILES: CC(C)(Sc1ccncc1-c1ccncc1)C(=O)O] | C |
| 2TT | 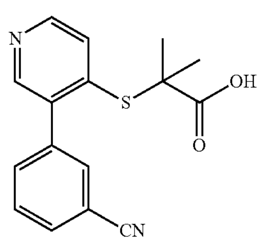 [SMILES: CC(C)(Sc1ccncc1-c1cccc(C#N)c1)C(=O)O] | B |
| 2UU | 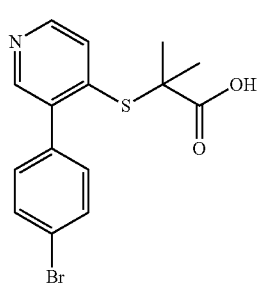 | C |

-continued

| Example | Structure | URAT1 EC50 Activity Ranking |
|---|---|---|
| 2VV | 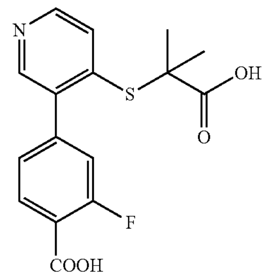 [SMILES: CC(C)(Sc1ccncc1-c1ccc(C(=O)O)c(F)c1)C(=O)O] | A |
| 2WW | 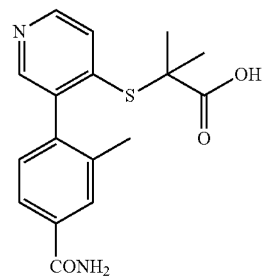 [SMILES: Cc1cc(C(N)=O)ccc1-c1cnccc1SC(C)(C)C(=O)O] | B |
| 2XX | 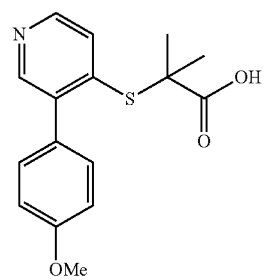 [SMILES: COc1ccc(-c2cnccc2SC(C)(C)C(=O)O)cc1] | B |
| 2YY | 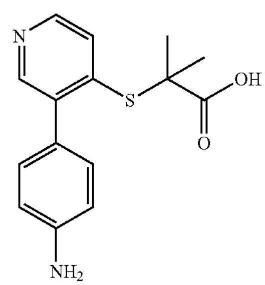 | A |
| 2ZZ | 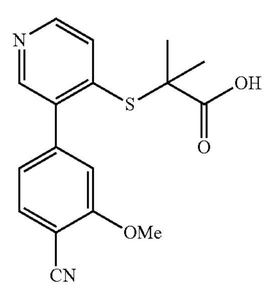 [SMILES: COc1cc(-c2cnccc2SC(C)(C)C(=O)O)ccc1C#N] | B |

| Example | Structure | URAT1 EC50 Activity Ranking |
|---|---|---|
| 2AAA | 3-(4-hydroxyphenyl)pyridin-4-yl sulfanyl isobutyric acid | C |
| 2BBB | 3-(4-cyano-3-fluorophenyl)pyridin-4-yl sulfanyl isobutyric acid | B |
| 2CCC | 3-(4-methylphenyl)pyridin-4-yl sulfanyl isobutyric acid | B |
| 2DDD | 3-(4-acetamidophenyl)pyridin-4-yl sulfanyl isobutyric acid | B |
| 2EEE | 3-(4-methanesulfonylphenyl)pyridin-4-yl sulfanyl isobutyric acid | B |
| 2FFF | 3-(3-chloro-4-cyanophenyl)pyridin-4-yl sulfanyl isobutyric acid | C |
| 3A | 4-(4-cyanophenyl)pyridin-3-yl sulfanyl isobutyric acid | A |
| 4A | 3-(4-cyanonaphthalen-1-yl)pyridin-2-yl sulfanyl isobutyric acid | B |
| 4B | 3-(4-cyanonaphthalen-1-yl)pyridin-2-yl sulfanyl acetic acid | A |
| 5A | 3-(4-cyanonaphthalen-1-yl)pyrazin-2-yl sulfanyl acetic acid | A |

-continued

| Example | Structure | URAT1 EC50 Activity Ranking |
|---|---|---|
| 6A | 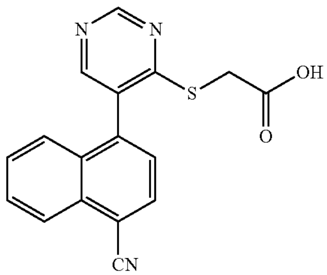 [SMILES: N#Cc1ccc(-c2cncnc2SCC(=O)O)c2ccccc12] | A |
| 7A | 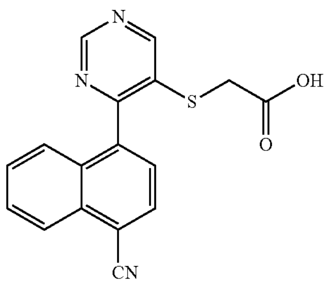 [SMILES: N#Cc1ccc(-c2ncncc2SCC(=O)O)c2ccccc12] | A |
| 2B | 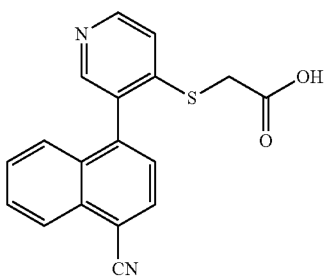 [SMILES: N#Cc1ccc(-c2cnccc2SCC(=O)O)c2ccccc12] | A |
| 2C | 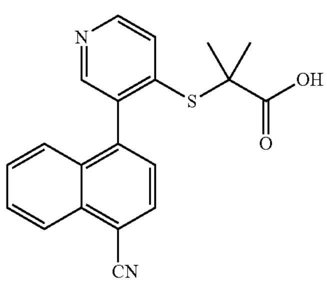 [SMILES: CC(C)(Sc1ccncc1-c1ccc(C#N)c2ccccc12)C(=O)O] | C |
| 2D | 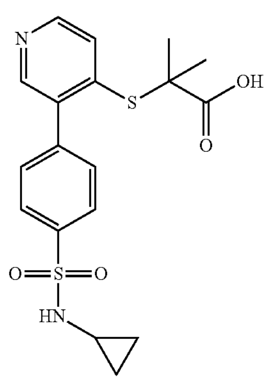 [SMILES: CC(C)(Sc1ccncc1-c1ccc(S(=O)(=O)NC2CC2)cc1)C(=O)O] | B |

-continued

| Example | Structure | URAT1 EC50 Activity Ranking |
|---|---|---|
| 2E | 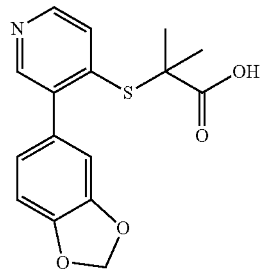 [SMILES: CC(C)(Sc1ccncc1-c1ccc2c(c1)OCO2)C(=O)O] | A |
| 2F | 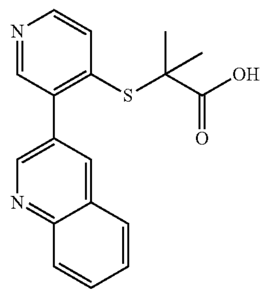 [SMILES: CC(C)(Sc1ccncc1-c1cnc2ccccc2c1)C(=O)O] | B |
| 2G | 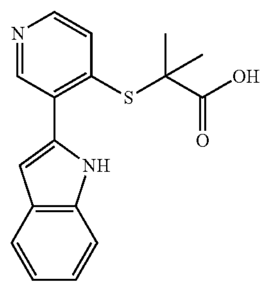 [SMILES: CC(C)(Sc1ccncc1-c1cc2ccccc2[nH]1)C(=O)O] | A |
| 2L | 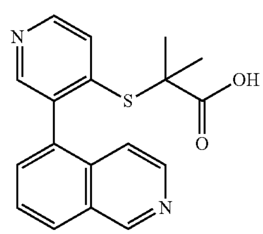 [SMILES: CC(C)(Sc1ccncc1-c1cccc2cnccc12)C(=O)O] | A |
| 2W | 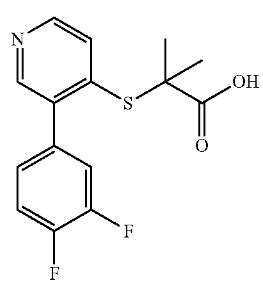 [SMILES: CC(C)(Sc1ccncc1-c1ccc(F)c(F)c1)C(=O)O] | B |

| Example | Structure | URAT1 EC50 Activity Ranking |
|---|---|---|
| 2Z | pyridine-naphthalene-S-C(CH3)2-COOH | A |
| 2AA | pyridine-(4-bromonaphthalene)-S-C(CH3)2-COOH | B |
| 2OO | pyridine-(4-dimethylaminophenyl)-S-C(CH3)2-COOH | A |
| 2QQ | pyridine-(1-methylpyrazol-4-yl)-S-C(CH3)2-COOH | A |
| 2RR | pyridine-(4-cyanomethylphenyl)-S-C(CH3)2-COOH | A |
| 2SS | pyridine-(4-carbamoylmethylphenyl)-S-C(CH3)2-COOH | A |
| 2GGG | pyridine-(4-mercaptophenyl)-S-C(CH3)2-COOH | B |
| 2HHH | pyridine-(2-fluoro-4-carboxyphenyl)-S-C(CH3)2-COOH | A |
| 2III | pyridine-(2-fluoro-4-cyanophenyl)-S-C(CH3)2-COOH | C |
| 2JJJ | pyridine-(2-fluoro-4-carbamoylphenyl)-S-C(CH3)2-COOH | B |

The examples and embodiments described herein are for illustrative purposes only and various modifications or changes suggested to individuals skilled in the art are to be included within the spirit and purview of this application and scope of the appended claims.

What is claimed is:

1. A compound of formula:

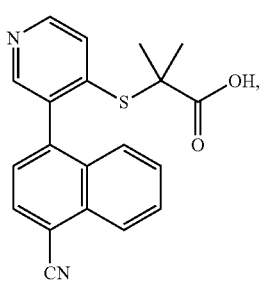 [SMILES: CC(C)(Sc1ccncc1-c1ccc(C#N)c2ccccc12)C(=O)O]

or a pharmaceutically acceptable salt or solvate thereof.

2. A pharmaceutical composition comprising a compound of formula:

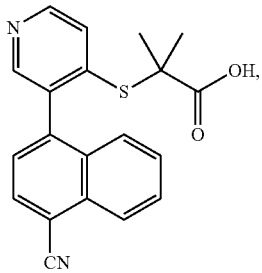 [SMILES: CC(C)(Sc1ccncc1-c1ccc(C#N)c2ccccc12)C(=O)O]

or a pharmaceutically acceptable salt or solvate thereof; and a pharmaceutically acceptable carrier.

3. The pharmaceutical composition of claim 2, together with a xanthine oxidase inhibitor.

4. The pharmaceutical composition of claim 3, wherein the xanthine oxidase inhibitor is allopurinol.

5. The pharmaceutical composition of claim 3, wherein the xanthine oxidase inhibitor is febuxostat.

6. A compound having the structure:

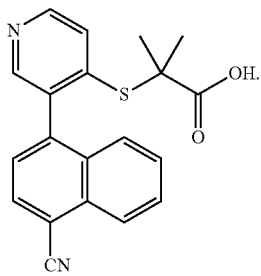 [SMILES: CC(C)(Sc1ccncc1-c1ccc(C#N)c2ccccc12)C(=O)O]

7. A pharmaceutical composition comprising a compound having the structure:

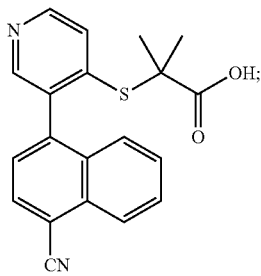

and a pharmaceutically acceptable carrier.

8. The pharmaceutical composition of claim 7, together with a xanthine oxidase inhibitor and a pharmaceutically acceptable carrier.

9. The pharmaceutical composition of claim 8, wherein the xanthine oxidase inhibitor is allopurinol.

10. The pharmaceutical composition of claim 8, wherein the xanthine oxidase inhibitor is febuxostat.

* * * * *